(12) United States Patent
Bauer et al.

(10) Patent No.: US 10,493,271 B2
(45) Date of Patent: Dec. 3, 2019

(54) IMPLANTABLE MEDICAL DEVICES, SYSTEMS, AND METHODS FOR SELECTION OF OPTIMAL DIAPHRAGMATIC STIMULATION PARAMETERS TO AFFECT PRESSURES WITHIN THE INTRATHORACIC CAVITY

(71) Applicant: VisCardia, Inc., Beaverton, OR (US)

(72) Inventors: Peter T. Bauer, Portland, OR (US); Edward Chinchoy, Studio City, CA (US); Jay Snell, Los Angeles, CA (US); Patricia A. Arand, McMinnville, OR (US)

(73) Assignee: VisCardia, Inc., Beaverton, OR (US)

( * ) Notice: Subject to any disclaimer, the term of this patent is extended or adjusted under 35 U.S.C. 154(b) by 7 days.

(21) Appl. No.: 15/498,316

(22) Filed: Apr. 26, 2017

(65) Prior Publication Data
US 2017/0312508 A1    Nov. 2, 2017

Related U.S. Application Data

(60) Provisional application No. 62/329,918, filed on Apr. 29, 2016.

(51) Int. Cl.
*A61N 1/00*    (2006.01)
*A61N 1/36*    (2006.01)
(Continued)

(52) U.S. Cl.
CPC ............ *A61N 1/3601* (2013.01); *A61B 5/021* (2013.01); *A61B 5/0215* (2013.01); *A61B 5/03* (2013.01);
(Continued)

(58) Field of Classification Search
CPC ...... A61N 1/3601; A61N 1/05; A61N 1/3627; A61N 1/37217; A61N 1/36585;
(Continued)

(56) References Cited

U.S. PATENT DOCUMENTS 4,411,268 A    10/1983    Cox
5,098,442 A    3/1992    Grandjean
(Continued)

FOREIGN PATENT DOCUMENTS

CA    1256507    6/1989
EP    1588735 A1    10/2005
(Continued)

OTHER PUBLICATIONS

Matuschak et al. "Hemodynamic effects of synchronous high-frequency jet ventilation during acute hypovolemia." J Appl Physiol. 61(1): 44-53 (Jul. 1986).
(Continued)

*Primary Examiner* — Lindsey G Wehrheim
(74) *Attorney, Agent, or Firm* — Loza & Loza, LLP; David S. Sarisky

(57) ABSTRACT

A controller delivers electrical stimulation therapy to a diaphragm through the one or more electrodes, and obtains a signal indicative of a pressure within an intrathoracic cavity from a pressure measurement source. The electrical stimulation therapy is defined by stimulation parameters. The controller obtains at least one additional signal indicative of a pressure within an intrathoracic cavity by changing at least one of the stimulation parameters, and delivering an electrical stimulation therapy to the diaphragm in accordance with the changed one of the plurality of stimulation parameters. The controller repeats the process of obtaining additional signals indicative of pressure based on a changing stimulation parameter by scanning through a range of values
(Continued)

for the changing stimulation parameter. The controller derives a measure of interest from each of the obtained signals, and selects as an optimal stimulation therapy, the electrical stimulation therapy that results in a most acceptable measure of interest.

39 Claims, 24 Drawing Sheets

(51) Int. Cl.
| | |
|---|---|
| *A61N 1/05* | (2006.01) |
| *A61B 5/021* | (2006.01) |
| *A61B 5/0452* | (2006.01) |
| *A61B 5/0456* | (2006.01) |
| *A61B 5/08* | (2006.01) |
| *A61B 5/113* | (2006.01) |
| *A61B 7/04* | (2006.01) |
| *A61B 17/00* | (2006.01) |
| *A61N 1/372* | (2006.01) |
| *A61B 5/0215* | (2006.01) |
| *A61B 5/03* | (2006.01) |
| *A61B 5/00* | (2006.01) |
| *A61B 5/042* | (2006.01) |
| *A61N 1/362* | (2006.01) |
| *A61B 5/04* | (2006.01) |
| *A61B 5/11* | (2006.01) |
| *A61N 1/365* | (2006.01) |

(52) U.S. Cl.
CPC ............ *A61B 5/042* (2013.01); *A61B 5/0452* (2013.01); *A61B 5/0456* (2013.01); *A61B 5/0816* (2013.01); *A61B 5/113* (2013.01); *A61B 5/4836* (2013.01); *A61B 5/686* (2013.01); *A61B 7/04* (2013.01); *A61B 17/00234* (2013.01); *A61N 1/05* (2013.01); *A61N 1/3627* (2013.01); *A61N 1/37217* (2013.01); *A61B 5/04012* (2013.01); *A61B 5/1102* (2013.01); *A61B 2562/0204* (2013.01); *A61B 2562/0219* (2013.01); *A61N 1/36585* (2013.01)

(58) Field of Classification Search
CPC ......... A61B 5/021; A61B 5/0215; A61B 5/03; A61B 5/042; A61B 5/0452; A61B 5/0456; A61B 5/0816; A61B 5/113; A61B 5/4836; A61B 5/686; A61B 7/04; A61B 17/00234; A61B 5/04012; A61B 5/1102; A61B 2562/0204; A61B 2562/0219
See application file for complete search history.

(56) References Cited

U.S. PATENT DOCUMENTS

| | | | |
|---|---|---|---|
| 5,188,098 A | 2/1993 | Hoffman et al. | |
| 5,300,094 A | 4/1994 | Kallok | |
| 5,358,519 A | 10/1994 | Grandjean | |
| 5,392,780 A | 2/1995 | Ogino et al. | |
| 5,632,716 A | 5/1997 | Bui | |
| 5,693,000 A | 12/1997 | Crosby | |
| 5,758,654 A | 6/1998 | Burton-Krahn et al. | |
| 6,415,183 B1 | 7/2002 | Scheiner | |
| 6,979,297 B2 | 12/2005 | Andresen et al. | |
| 7,039,538 B2 | 5/2006 | Baker, Jr. | |
| 7,072,708 B1 | 7/2006 | Andresen et al. | |
| 7,074,195 B2 | 7/2006 | Nelson et al. | |
| 7,096,060 B2 | 8/2006 | Arand et al. | |
| 7,096,064 B2 | 8/2006 | Deno et al. | |
| 7,113,820 B2 | 9/2006 | Schlegel et al. | |
| 7,171,269 B1 | 1/2007 | Addison et al. | |
| 7,174,203 B2 | 2/2007 | Arand et al. | |
| 7,225,021 B1 | 5/2007 | Park et al. | |
| 7,248,923 B2 | 7/2007 | Maile et al. | |
| 7,277,757 B2 | 10/2007 | Casavant | |
| 7,302,290 B2 | 11/2007 | Bauer | |
| 7,357,775 B1 | 4/2008 | Koh | |
| 7,424,321 B2 | 9/2008 | Wariar et al. | |
| 7,435,221 B1 | 10/2008 | Bhami et al. | |
| 7,437,699 B2 | 10/2008 | Morita et al. | |
| 7,467,012 B1 | 12/2008 | Park et al. | |
| 7,559,903 B2 | 7/2009 | Moussavi et al. | |
| 7,668,589 B2 | 2/2010 | Bauer | |
| 7,725,181 B1 | 5/2010 | Bornzin et al. | |
| 7,819,814 B2 | 10/2010 | Gavirely et al. | |
| 7,979,128 B2 | 7/2011 | Tehrani et al. | |
| 7,994,655 B2 | 8/2011 | Bauer et al. | |
| 8,065,002 B2 | 11/2011 | Arand et al. | |
| 8,105,241 B2 | 1/2012 | Nelson et al. | |
| 8,137,283 B2 | 3/2012 | Syeda-Mahmood et al. | |
| 8,140,164 B2 | 3/2012 | Tehrani et al. | |
| 8,185,190 B2 | 5/2012 | Bauer | |
| 8,200,336 B2 | 6/2012 | Tehrani | |
| 8,233,987 B2 | 7/2012 | Gelfand | |
| 8,244,358 B2 | 8/2012 | Tehrani et al. | |
| 8,244,359 B2 | 8/2012 | Gelfand | |
| 8,265,759 B2 | 9/2012 | Tehrani et al. | |
| 8,348,852 B2 | 1/2013 | Bauer et al. | |
| 8,409,108 B2 | 4/2013 | Bauer et al. | |
| 8,412,323 B2 | 4/2013 | Bauer | |
| 8,433,412 B1 | 4/2013 | Westlund | |
| 8,548,588 B1 | 10/2013 | Bauer | |
| 8,577,448 B2 | 11/2013 | Bauer et al. | |
| 8,706,236 B2 | 4/2014 | Ignagni | |
| 8,909,341 B2 | 12/2014 | Gelfand | |
| 2002/0103521 A1 | 8/2002 | Swoyer et al. | |
| 2002/0188329 A1 | 12/2002 | Struble | |
| 2003/0187337 A1 | 10/2003 | Tarassenko et al. | |
| 2004/0088015 A1 | 5/2004 | Casavant | |
| 2004/0127792 A1 | 7/2004 | Siejko et al. | |
| 2004/0230105 A1 | 11/2004 | Geva et al. | |
| 2005/0027323 A1 | 2/2005 | Mulligan et al. | |
| 2005/0043644 A1 | 2/2005 | Stahmann et al. | |
| 2005/0065563 A1 | 3/2005 | Scheiner | |
| 2005/0080348 A1 | 4/2005 | Stahmann et al. | |
| 2005/0085865 A1 | 4/2005 | Tehrani | |
| 2005/0085869 A1* | 4/2005 | Tehrani | A61N 1/3601 607/42 |
| 2005/0090870 A1 | 4/2005 | Hine | |
| 2005/0222515 A1 | 10/2005 | Polyshchuk et al. | |
| 2006/0079942 A1 | 4/2006 | Deno et al. | |
| 2006/0122661 A1 | 6/2006 | Mandell | |
| 2006/0122662 A1 | 6/2006 | Tehrani et al. | |
| 2006/0155202 A1 | 7/2006 | Arand et al. | |
| 2007/0021795 A1 | 1/2007 | Tehrani | |
| 2007/0038137 A1 | 2/2007 | Arand et al. | |
| 2007/0055151 A1 | 3/2007 | Shertukde et al. | |
| 2007/0191725 A1 | 8/2007 | Nelson | |
| 2008/0021510 A1 | 1/2008 | Mi et al. | |
| 2008/0125820 A1 | 5/2008 | Stahmann et al. | |
| 2008/0167695 A1 | 7/2008 | Tehrani | |
| 2008/0177191 A1 | 7/2008 | Patangay et al. | |
| 2008/0188904 A1 | 8/2008 | Tehrani et al. | |
| 2008/0215106 A1 | 9/2008 | Chang et al. | |
| 2008/0255465 A1 | 10/2008 | Nelson | |
| 2008/0288010 A1 | 11/2008 | Tehrani | |
| 2008/0288015 A1 | 11/2008 | Tehrani et al. | |
| 2009/0024176 A1 | 1/2009 | Yun et al. | |
| 2009/0112107 A1 | 4/2009 | Nelson et al. | |
| 2009/0122108 A1 | 4/2009 | Nelson et al. | |
| 2009/0165559 A1 | 7/2009 | Lec | |
| 2009/0192561 A1 | 7/2009 | Bauer | |
| 2009/0296388 A1 | 12/2009 | Wu et al. | |
| 2010/0094148 A1 | 4/2010 | Bauer et al. | |
| 2010/0331903 A1 | 12/2010 | Zhang et al. | |
| 2011/0015702 A1 | 1/2011 | Ternes et al. | |
| 2011/0230932 A1 | 9/2011 | Tehrani | |
| 2011/0288609 A1 | 11/2011 | Tehrani et al. | |
| 2012/0296388 A1 | 11/2012 | Zhang | |

(56) References Cited

U.S. PATENT DOCUMENTS

| | | |
|---|---|---|
| 2013/0030498 A1 | 1/2013 | Karamanoglu |
| 2014/0114371 A1 | 4/2014 | Westlund |
| 2014/0172040 A1 | 6/2014 | Bauer |
| 2017/0143973 A1 | 5/2017 | Tehrani |

FOREIGN PATENT DOCUMENTS

| | | |
|---|---|---|
| JP | 2010537716 A | 12/2010 |
| WO | 2009029172 A1 | 3/2009 |
| WO | 2016033245 A1 | 3/2016 |

OTHER PUBLICATIONS

Pinsky et al. "Hemodynamic effects of cardiac cycle-specific increases in intrathoracic pressure." J Appl Physiol. 60(2):604-12 (Feb. 1986).

Pinsky et al. "Augmentation of cardiac function by elevation of intrathoracic pressure."J Appl Physiol. 54(4):950-55 (Apr. 1983).

Pinsky, et al., "Determinants of cardiac augmentation by elevations in intrathoracic pressure." J Appl Physiol. 58(4):1189-98 (May 1985).

Roos, Markus, et al; Improved cardiac performance through pacing-induced diaphragmatic stimulation: a novel electrophysiological approach in heart failure management? European Society of Cardiology. Clinical Research. Pacing and Cardiac Resynchronization Therapy. Europace (2009) 11, 191-199. Lucerne, Switzerland (Dec. 8, 2008).

Zuber, Michel, et al; Detection and Hemodynamic Significance of Cardiac Pacemaker—Induced Phrenic Nerve Stimulation. Department of Cardiology, Kantonsspital, Luzern, Switzerland. 2010 Wiley Periodicals, Inc. Lucerne, Switzerland (Aug. 13, 2009).

PCT Patent Application No. PCT/US2013/075489. International Search Report & Written Opinion (dated Mar. 11, 2014).

PCT Patent Application No. PCT/US2013/075489. International Preliminary Report on Patentability (dated Jul. 2, 2015).

PCT/US2017/029905. International Search Report & Written Opinion (dated Aug. 8, 2017).

PCT/US2017/029939 International Search Report & Written Opinion (dated Aug. 10, 2017).

PCT/US2017/029924. International Search Report & Written Opinion (dated Oct. 2, 2017).

PCT/US2017/029924. Written Opinion of the International Preliminary Examining Authority (dated Apr. 6, 2018).

PCT/US2017/029939. Written Opinion of the International Preliminary Examining Authority (dated Apr. 6, 2018).

Beeler et al. "Improvement of cardiac function with device-based diaphragmatic stimulation in chronic heart failure patients: the randomized, open-label, crossover Epiphrenic II Pilot Trial." European Journal of Heart Failure (2014) 16. pp. 342-349. European Society of Cardiology.

PCT/US2017/051021. International Search Report & Written Opinion (dated Dec. 12, 2017).

PCT/US2017/029924. International Preliminary Report on Patentability (dated Aug. 10, 2018).

PCT/US2017/051021. Written Opinion (dated Aug. 24, 2018).

PCT/US2017/029939. International Preliminary Report on Patentability (dated Oct. 12, 2018).

PCT/US2017/051021. International Preliminary Report on Patentability (dated Jan. 3, 2019).

JP Patent Appln. No. 2015-549544. Office Action (dated Sep. 21, 2017).

EP Patent Appln. No. Office Action (dated Sep. 29, 2017).

U.S. Appl. No. 15/498,352. Office Action (dated Apr. 17, 2019).

* cited by examiner

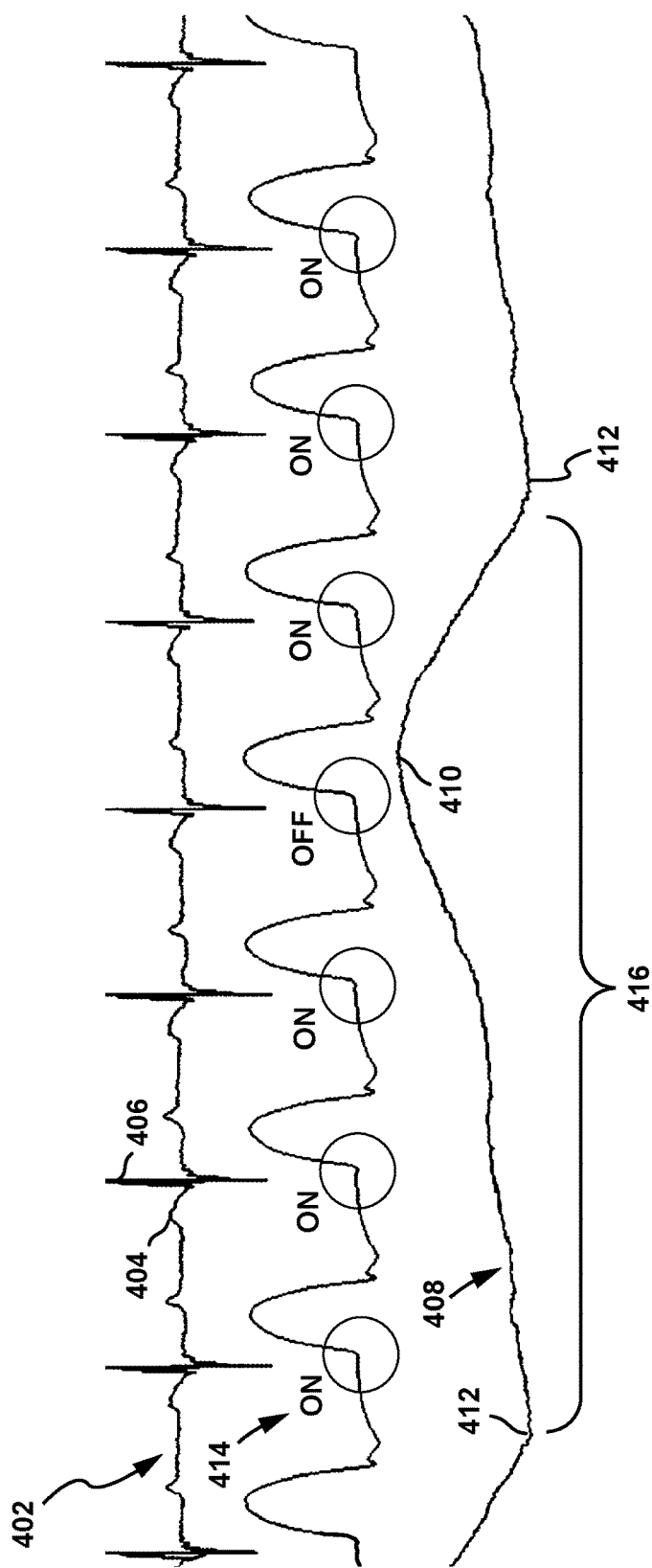

Delay period 1

Delay period 2

Delay period 3

Delay period 4

Delay period 5

Delay period 6

IMPLANTABLE MEDICAL DEVICES, SYSTEMS, AND METHODS FOR SELECTION OF OPTIMAL DIAPHRAGMATIC STIMULATION PARAMETERS TO AFFECT PRESSURES WITHIN THE INTRATHORACIC CAVITY

CROSS-REFERENCE TO RELATED APPLICATION

This application claims the benefit of U.S. Provisional Application Ser. No. 62/329,918, entitled "Implantable Medical Device and Methods for Mediating Thoracic Cavity Pressure to Affect Cardiac Function, and Associated Delivery Tools and Implant Methods" and filed on Apr. 29, 2016, which is expressly incorporated by reference herein in its entirety.

BACKGROUND

Field

The present disclosure relates generally to devices and method for affecting cardiac function, and more particularly, to implantable medical devices and methods that affect pressures within the intrathoracic cavity through diaphragmatic stimulation to thereby affect cardiovascular performance.

Background

The diaphragm is a dome shaped skeletal muscle structure separating the thoracic and abdominal cavities. It is the major muscular organ responsible for mechanical respiratory motion by deflecting downwards upon contraction during inspiration. The phrenic nerve innervates the diaphragm and acts as the primary method of nervous excitation to signal contraction. The external and internal intercostal muscles also elevate the ribs increasing the anterior-posterior diameter of the thoracic cavity. During inspiration, the movement of the diaphragm results in expansion and negative pressure within the thoracic cavity as the diaphragm and intercostal muscles increase the size of the thorax. The expanding thorax causes the intrathoracic pressure to decrease below atmospheric pressure and air moves into the lungs. During exhalation, the inspiratory muscles relax, and the elastic recoil of the lung tissues, combined with a rise in intrathoracic pressure, causes air to move out of the lungs.

Changes in intrathoracic pressure from diaphragmatic contraction and thoracic expansion may be transmitted to the intrathoracic structures namely the heart, pericardium, great arteries and veins. Spontaneous inspiration produces a negative pleural pressure affecting cardiovascular performance including atrial filling (preload) and resistance to ventricular emptying (afterload). This affect can be observed in cardiovascular hemodynamic parameters during normal function when diaphragmatic contractions is of sufficient duration, intensity and expansiveness to cause inspiration, and used in clinical practice during Vasalva and Mueller maneuvers where patients forcefully inspire or expire using diaphragmatic muscles against a closed glottis causing a rapid change in thoracic pressures. These maneuvers result in pronounced rapid acute changes to intrathoracic pressure, which changes in turn alter pressure gradients associated with the cardiac chambers and vessels to affect cardiac functions, including cardiac filling and output.

The effects of intrathoracic pressure on cardiac systemic performance are complex. Hiccups, which result from rapid partial diaphragmatic contractions causing rapid decreases to intrathoracic pressure, have been previously used to characterize their effects of cardiac and systemic performance. Studies of both animal and human subjects demonstrated changes to hemodynamic parameters including overall ventricular diastolic and systolic pressures, cardiac output and changes to systemic measures including aortic distention and vascular resistance. These studies also demonstrated that rapid intrathoracic pressure effect changes are highly sensitive to timing relative to the cardiac cycle, with different effects observed if the hiccups occur during ventricular diastolic, systole, or during the diastole-systole transition.

SUMMARY

In one embodiment, diaphragmatic stimulation therapy delivered to a patient through an implantable medical device is optimized by scanning through variations of electrical stimulation therapy, obtaining physiological measures resulting from these variations, and evaluating the measures to identify an optimal stimulation therapy. Optimization may be performed periodically, such as once a day, and may be performed entirely by the implantable medical device, or by the implantable medical device in conjunction with an external processor.

In this embodiment, an apparatus for determining an optimal stimulation therapy to a diaphragm of a patient for affecting cardiac performance, includes one or more electrodes configured for placement on or near the diaphragm, and a pressure measurement source configured to provide a signal indicative of a pressure within an intrathoracic cavity of the patient. The pressure measurement source may be a pressure sensor or a motion sensor, e.g., accelerometer or acoustic transducer, configured to be associated with the intrathoracic cavity, or with a cardiovascular structure within the intrathoracic cavity. The apparatus also includes a controller that delivers an electrical stimulation therapy to the diaphragm through the one or more electrodes, and obtains the signal indicative of a pressure within an intrathoracic cavity of the patient from the pressure measurement source, resulting from the delivered electrical stimulation. The electrical stimulation therapy is typically delivered in regular periodic synchrony or near synchrony with a cardiac event that occurs on a heart-beat by heart-beat basis, such as a normal intrinsic ventricular depolarization. These beat-by-beat cardiac events may be referred to herein as "cyclic cardiac events." The electrical stimulation therapy delivered by the controller is defined by stimulation parameters, including a timing parameter and pulse parameters.

The controller is configured to obtain at least one additional signal indicative of a pressure within an intrathoracic cavity of the patient by changing at least one of the plurality of stimulation parameters, and delivering an electrical stimulation therapy to the diaphragm of the patient in accordance with the changed one of the plurality of stimulation parameters. The controller may repeat the process of obtaining additional signals indicative of pressure based on a changing stimulation parameter by scanning through a range of possible values for the changing stimulation parameter. Once a number of signals indicative of pressure within the intrathoracic cavity are obtained, the controller then derives a measure of interest from each of the obtained signals, and selects as the optimal stimulation therapy, the electrical stimulation therapy that results in a most acceptable measure of interest. A most acceptable measure of interest may correspond to the measure of interest having a greatest deviation from a baseline value, or it may correspond to the measure of interest that falls within a threshold range of acceptable measures of interest.

In another embodiment, diaphragmatic stimulation therapy delivered to a patient through an implantable medical device for the purpose of affecting a non-respiratory pressure within an intrathoracic cavity of a patient, may be adjusted or optimized in real-time or near real-time by obtaining physiological measures resulting from the delivery of electrical stimulation to the diaphragm, evaluating the measures against baseline values, and adjusting the electrical stimulation therapy based on the evaluation outcomes.

In this embodiment, an apparatus for affecting a pressure within an intrathoracic cavity of a patient includes one or more electrodes configured for placement on or near a diaphragm of the patient, and a pressure measurement source configured to provide a signal indicative of a pressure within an intrathoracic cavity of the patient. The pressure measurement source may be a pressure sensor that provides a signal indicative of the pressure corresponding one of intrathoracic pressure, right atrial pressure, right ventricular pressure, left ventricular pressure, aortic pressure, and pulmonary artery pressure. The pressure measurement source may also be a motion sensor that provides a signal indicative of the pressure corresponds corresponding to one of movement of the diaphragm or heart sounds.

The apparatus also includes a controller that detects a cyclic cardiac event of the patient based on a signal obtained from the one or more electrodes, and delivers an electrical stimulation therapy to a diaphragm of the patient through the one or more electrodes. The delivery of the electrical stimulation therapy is timed to the detection of the cyclic cardiac event, and the electrical stimulation therapy is defined by a plurality of stimulation parameters. The controller monitors, in real time or near real time, a pressure associated with the intrathoracic cavity based on the signal provided by the pressure measurement source, to determine whether an adjustment of one or more of the plurality of stimulation parameters is warranted, and adjusts, in real time or near real time, one or more of the stimulation parameters based on the monitoring. For example, the controller may compare a pressure measure against a baseline measure and adjust one or more stimulation parameter to achieve a desired intrathoracic pressure at a point in the patient's hemodynamic cycle. The controller may also detect a respiration cycle event from a signal representing one of movement of the diaphragm or heart sounds, and withhold delivery of a stimulation pulse timed to be delivered at or near a time of the respiration cycle event.

In another embodiment, diaphragmatic stimulation therapy delivered to a patient through an implantable medical device for the purpose of affecting a non-respiratory pressure within an intrathoracic cavity of a patient, may be modified based on respiration events.

In this embodiment, an apparatus for affecting a pressure within an intrathoracic cavity of a patient includes one or more electrodes configured for placement on or near a diaphragm of the patient, and a pressure measurement source configured to provide a signal indicative of a pressure within an intrathoracic cavity of the patient. The pressure measurement source may be a motion sensor that provides a signal indicative of the pressure corresponds corresponding to one of movement of the diaphragm or heart sounds.

The apparatus also includes a controller that delivers an electrical stimulation therapy to a diaphragm of the patient through the one or more electrodes in synchrony or near synchrony with an occurrence of a cyclic cardiac event. The cyclic cardiac event may be, for example, a ventricular depolarization. The controller monitors a pressure associated with the intrathoracic cavity based on the signal provided by the pressure measurement source, to detect for an occurrence of a respiration event. For example, the controller may detect changes or patterns in intrathoracic pressure with which different stages of respiration, e.g., end inspiration, may be associated. The controller withholds delivery of an electrical stimulation that is timed to be delivered at or near the occurrence of the respiration event.

In another embodiment, an implantable medical device for delivering stimulation therapy to a diaphragm of a patient may include a lead coupled to a controller. The lead places and secures a sensor assembly, including one or more electrodes, on the surface of the diaphragm, while preserving the hermetic integrity of the intrathoracic cavity.

A lead configured as such, includes a sensor assembly, a connector, and a lead body. The sensor assembly is at a distal end of the lead, and includes a housing having a first end surface and a second end surface opposite the first end surface. The first end surface is the surface of the sensor assembly that is intended to contact the diaphragm. The sensor assembly further includes a sensor structure associated with the first end surface and at least one fixation structure also associated with the first end surface. The sensor structure includes at least one sensor, while the fixation structure is configured to preserve the hermetic integrity of the intrathoracic cavity. For example, the fixation structure may extend through the diaphragm and transition to a state that forms a seal between the fixation structure and tissue of the diaphragm. Alternatively, the fixation structure may surround the sensor assembly and form a seal between itself and the surface of the diaphragm. The connector is at a proximal end of the lead and has at least one conductor pin. The lead body extends between the sensor assembly and the connector, and includes at least one conductor that electrically couples the at least one sensor to the at least one conductor pin.

BRIEF DESCRIPTION OF THE DRAWINGS

Various aspects of devices and methods that affect pressures within the intrathoracic cavity through diaphragmatic stimulation will now be presented in the detailed description by way of example, and not by way of limitation, referring to the accompanying drawings, wherein:

FIG. 4A are waveforms representing—from top to bottom—a cardiac electrical activity signal, a cardiac pressure signal, and an intrathoracic pressure signal.

DETAILED DESCRIPTION

Figure 1:
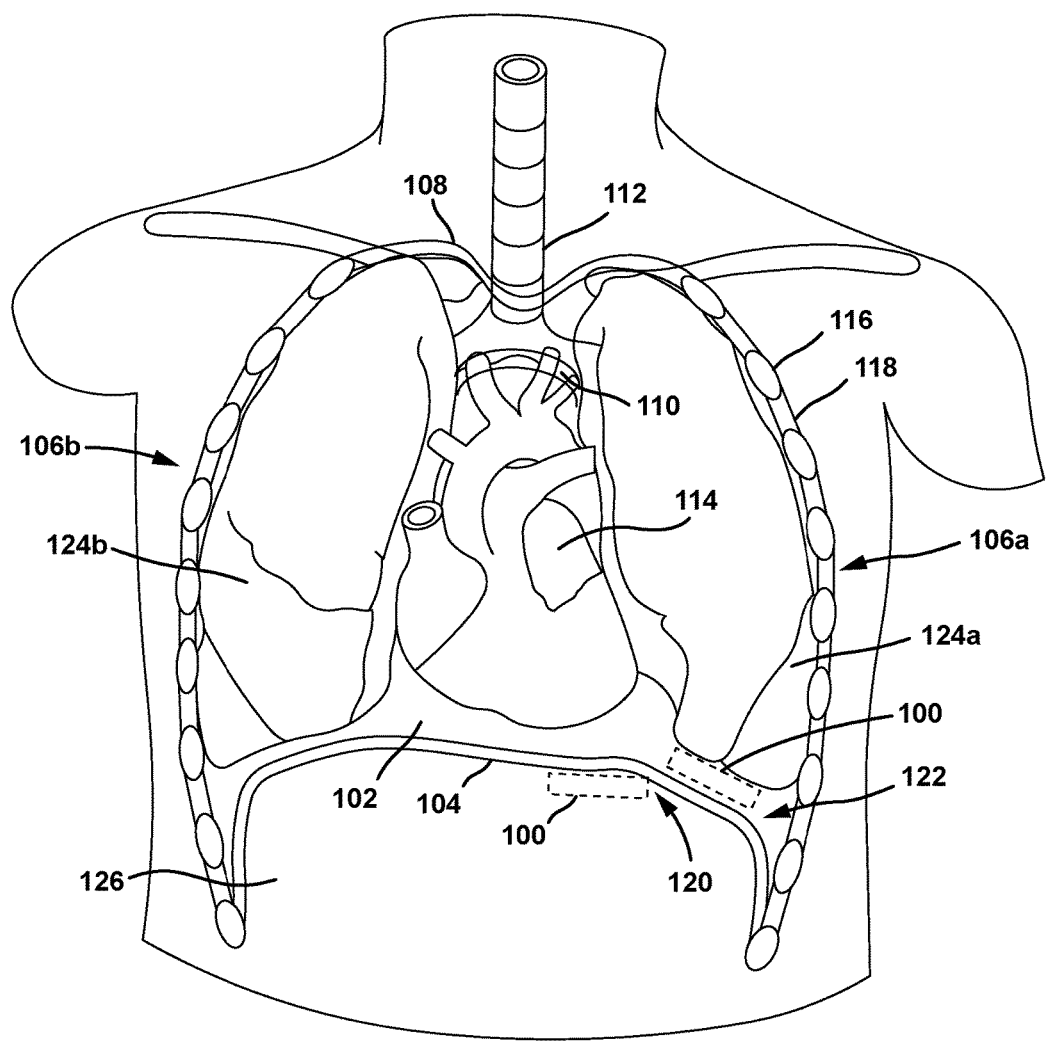
FIG. 1 is an illustration of an implantable medical device shown in two alternate location relative to the thoracic cavity of a patient.

Disclosed herein are implantable medical devices and that provide therapy, in the form of diaphragmatic stimulation, that affects pressures within the intrathoracic cavity to thereby affect cardiovascular performance. Also disclosed are methods for optimizing such therapy for individual patients through diaphragmatic stimulation parameter adjustments, where adjustments are made based on measures of pressures within the intrathoracic cavity.

Electrical stimulation to the diaphragm induces partial, asymptomatic diaphragmatic contractions, which in turn induces changes in intrathoracic pressures. Appropriately timed and configured diaphragmatic stimulation may improve cardiovascular performance and cardiac function, to thereby manage heart failure. For example, diaphragmatic stimulation synchronized with, or otherwise timed to an occurrence of a cyclic cardiac event, such as ventricular systole may accelerate negative intrathoracic cavity pressure (suction) during left ventricular filling to increase filling volume, and then accelerate positive intrathoracic cavity pressure (compression) to augment systolic contractile forces generated by the left ventricle.

Because the management of heart failure is complex and physicians need to optimize numerous various and interdependent physiologic effects between the heart and vessels, an objective of the therapy disclosed herein is to utilize evoked diaphragmatic contractions to optimize the operating intrathoracic pressure conditions on the heart and vessels for improving the patient's overall condition. These include: the blood volume to one or more chambers of the cardiovascular system within the thoracic cavity, end diastolic pressure (preload) that causes changes to systolic output (starling), that mediates intracardiac blood flow (diastolic coronary perfusion) and operating mechanics (efficiency), or for decreasing the compliance of the vessels responsible for cardiac filling (vena cava and right atrium) or for altering the compliance of cardiac vessels to better match the operational ability of the heart (impedance matching or optimization). These indirect physiologic mechanisms will augment the direct physiologic mechanism of mechanically augmenting the mechanical forces of the heart and decreasing the vascular resistance to cardiac output.

Implantable Medical Devices for Diaphragmatic Stimulation

The implantable medical devices may be embodied in a variety of forms, such as disclosed in U.S. patent Application Publication No, 2017/0021166, titled Systems, Devices, and Methods for Improving Hemodynamic Performance Through Asymptomatic Diaphragm Stimulation, the disclosure of which is hereby incorporated by reference. For example, the implantable medical device may be in the form of a single, unitary structure having no removable component parts. Alternatively, the implantable medical device may be formed of multiple component parts that interface either through a mechanical connection or through wireless communication.

FIG. 1 is an illustration of an implantable medical device (IMD) 100, in the form of a single, unitary structure, implanted in the region of a patient's thoracic cavity 102 on or near the patient's diaphragm 104. The IMD 100 may be placed, through conventional laparoscopy, at a selected surface region of the diaphragm 104 on the inferior side of the diaphragm at a location referred to as an inferior implant location 120. Alternatively, the IMD 100 may be placed, through conventional thoracotomy, at a selected surface region of the diaphragm 104 on the superior side of diaphragm 104 at a location referred to as a superior implant location 122. For example, the IMD 100 may be positioned between the superior surface of diaphragm 104 and the underside of the patient's left lung 124a.

The thoracic cavity 102, also referred to as the intrathoracic cavity and the mediastinum, is a hermetically sealed cavity formed by various connected structures. These structures include the diaphragm 104, the thoracic sidewalls 106a, 106b, and layered walls 108, 110, near the trachea 112 and the heart 114.

The diaphragm 104 is a dome-shaped skeletal muscle structure located below the lungs 124a, 124b that separates the thoracic cavity 102 from the abdominal cavity 126. The diaphragm 104 defines the lower end of the thoracic cavity 102 and is the major muscular organ responsible for mechanical respiratory motion. The thoracic sidewalls 106a, 106b are formed of ribs 116 and membrane 118 filing the space between the ribs, and define the thoracic sidewalls 106a, 106b of the thoracic cavity 102. The layered walls 108, 110 are formed of various membranes and vessels which lay over each other to form a seal at the top of the thoracic cavity 102.

Mechanical respiratory motion includes an inspiration or inhalation phase and an expiration or exhalation phase. As previously mentioned, the diaphragm 104 is the major muscular organ responsible for mechanical respiratory motion. The phrenic nerve (not shown) innervates the diaphragm 104 and sends signals to the diaphragm to control inspiration and expiration. These signals act as the primary mechanism for initiating contraction of the diaphragm through nervous excitation. Since nervous endings responsible for pain sensation are absent within the diaphragm, a confine of therapy outputs are those which provide the desired hemodynamic effects to the cardiovascular system while simultaneously minimizing the likelihood of field stimulation of pain nerves contained within other nearby innervated thoracic cavity musculature.

Figure 2A:
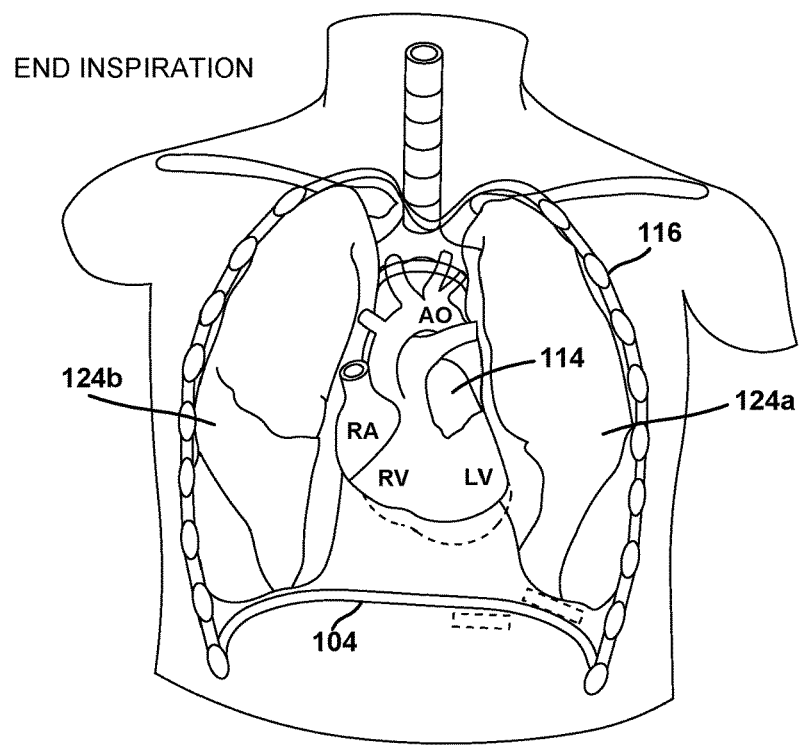
FIG. 2A is an illustration of the thoracic cavity at end inspiration.

FIG. 2A is an illustration of the thoracic cavity at end inspiration. During inspiration, the diaphragm 104 contracts, e.g., flattens out, and deflects downward, in a direction away from the lungs 124a, 124b. Concurrent with downward deflection of the diaphragm during inspiration, the external and internal intercostal muscles around the lungs 124a, 124b elevate the ribs 116, thereby increasing the anterior-posterior diameter of the thoracic cavity 102. During inspiration, the movement of the diaphragm 104 results in expansion and negative pressure within the thoracic cavity 102 as the diaphragm and intercostal muscles increase the size of the thorax. The expanding thorax causes the pressure within the open space of thoracic cavity 102, i.e., the intrathoracic pressure, to decrease below atmospheric pressure. The pressure decrease causes external air to move into the lungs 124a, 124b.

Figure 2B:
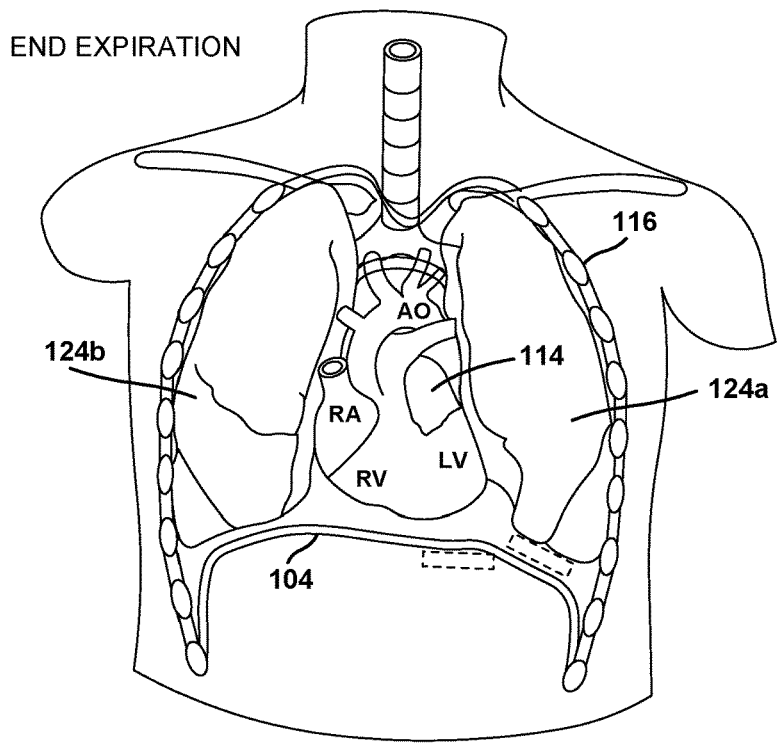
FIG. 2B is an illustration of the thoracic cavity at end expiration.

FIG. 2B is an illustration of the thoracic cavity at end expiration. During expiration, the diaphragm 104 expands, e.g., assumes a dome shape, and deflects upward, in the direction of the lungs 124a, 124b. During expiration, the diaphragm 104, together with the external and internal intercostal muscles around the lungs 124a, 124b relax. The diaphragm 104 expands, e.g., resumes a dome shape, and the ribs 116 de-elevate, thereby reducing the anterior-posterior diameter of the thoracic cavity 102, and causing the intrathoracic pressure to increase above atmospheric pressure. The increase in intrathoracic pressure in combination with the elastic recoil of lung tissues, causes air to move out of the lungs.

Changes in the pressure within the open space of the thoracic cavity 102, i.e., the intrathoracic pressure, due to diaphragm contraction and thoracic cavity expansion, and diaphragm expansion and thoracic cavity contraction bring about changes in other pressures within the intrathoracic cavity, including pressures associated with intrathoracic structures like the heart 114, pericardium, great arteries and veins. For example, changes in cardiovascular pressures, such as right atrial (RA) pressure, right ventricular (RV) pressure, left ventricular (LV) pressure, and aortic (AO) pressure result from changes in intrathoracic pressure.

In accordance with presently disclosed embodiments of IMDs and therapy methods, intrathoracic pressure is manipulated through controlled delivery of diaphragmatic stimulation by the IMD, to bring about desirable changes in other pressures within the intrathoracic cavity to improve cardiac function. As previously described, through delivery of appropriate stimulation therapy to the diaphragm by the IMD, partial, asymptomatic contractions of the diaphragm are induced in synchrony or near synchrony with cardiac events. Timing the occurrences of these partial, asymptomatic contractions relative to cardiac events results in changes in intrathoracic pressure, which in turn, increases and/or decreases pressures associated with the heart, pericardium, great arteries and veins to thereby improve hemodynamic function of the heart.

Signals indicative of pressures within the intrathoracic cavity, including intrathoracic pressure itself, and other pressures, such as cardiovascular pressures, may be monitored and used as a feedback mechanism to adjust diaphragmatic stimulation therapy. To this end, one or more parameters that define diaphragmatic stimulation therapy may be changed to obtain a desired increase and/or decrease in pressures associated with the heart, pericardium, great arteries and veins. For example, in the case of electrical stimulation therapy, one or more of the timing at which an electrical stimulation pulse is delivered, a pulse waveform type, a pulse amplitude, a pulse duration, and a pulse polarity, may be adjusted or changed.

Other signals indicative of pressures within the intrathoracic cavity, such as heart sounds, may also be monitored and used as a feedback mechanism to adjust diaphragmatic stimulation therapy. For example, heart sound signals may be used to determine timings between occurrences of cardiac events. One or more parameters that define diaphragmatic stimulation therapy may be changed to obtain a desired increase and/or decrease in these timings.

Signals indicative of pressures within the intrathoracic cavity may also be monitored to detect respiration events, such as end inspiration. Detections of such events may serve as a triggering event that alters diaphragmatic stimulation therapy for a time associated with the event. For example, upon detection of end inspiration, stimulation therapy may be altered, for example, by either withholding delivery of stimulation therapy at the time of end inspiration, or changing one or more parameters of the stimulation therapy delivered at the time of end inspiration. Altering the stimulation therapy in such instances is beneficial in that it delivers the minimal amount of energy required to obtain the desired hemodynamic benefit, thereby decreasing the likelihood of inducing patient symptoms including pain while simultaneously extending device battery longevity.

Figure 3:
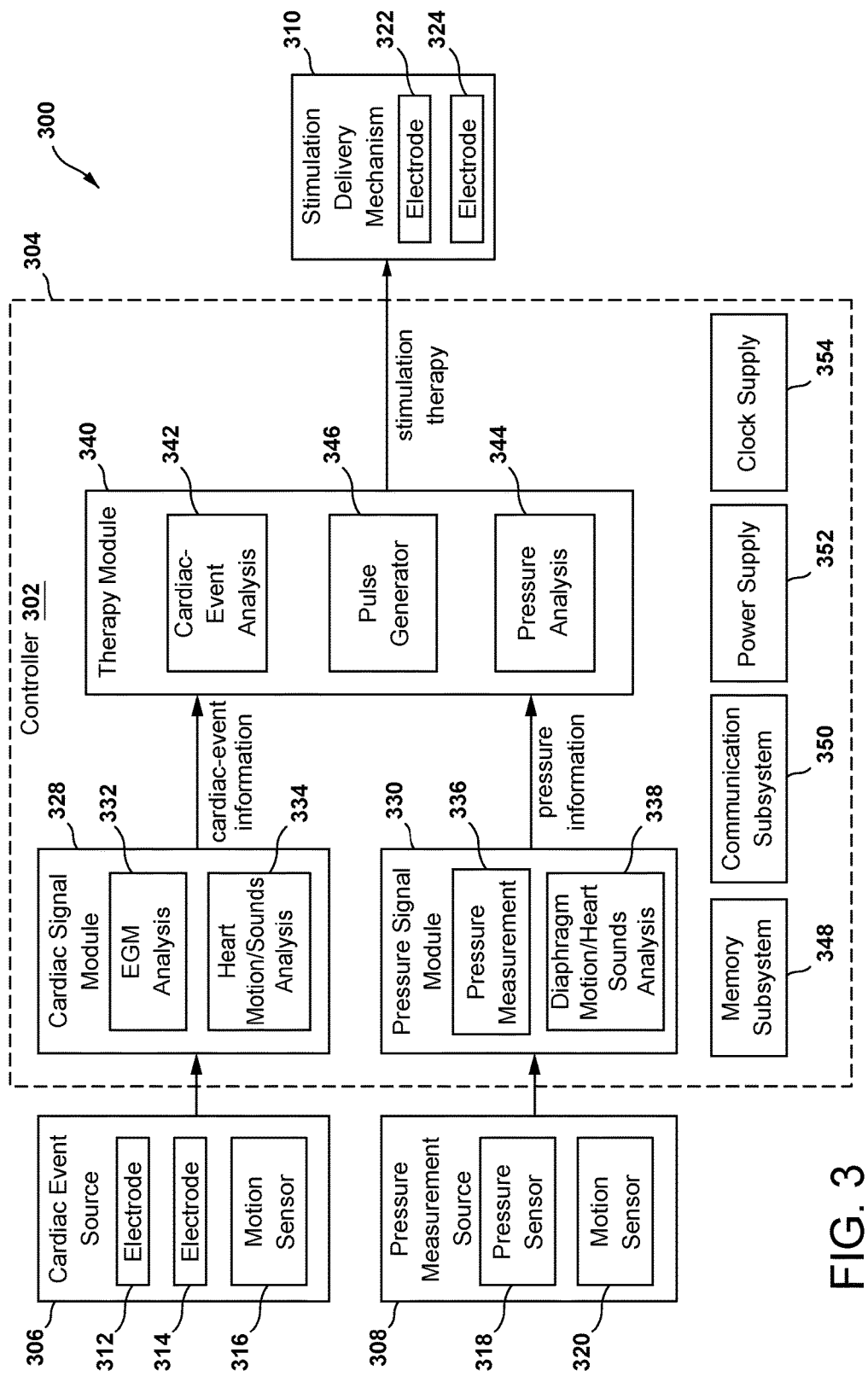
FIG. 3 is a block diagram of an implantable medical device configured to affect pressures within the intrathoracic cavity through delivery of diaphragmatic stimulation.

FIG. 3 is a block diagram of an IMD 300 configured to affect pressures within the intrathoracic cavity through delivery of diaphragmatic stimulation. The IMD 300 includes a controller 302 within a housing 304, a cardiac event source 306, a pressure measurement source 308, and a stimulation delivery mechanism 310, each of which may be coupled for interaction with the controller, either through a wired connection or through a wireless connection. The controller 302 includes a cardiac signal module 328, a pressure signal module 330, a therapy module 340, and various other modules.

The cardiac event source 306 is configured to provide signals to the controller 302 that represent cardiac events.

For example, the cardiac event source 306 may be one or more electrodes 312, 314 configured to be positioned on or near a diaphragm to sense electrical signals representative of cardiac events and to provide the signals to the controller 302. Alternatively, the one or more electrodes 312, 314 may be configured to be positioned in, on, or adjacent to an intrathoracic structure, e.g. heart, pericardium, great artery and vein, within the intrathoracic cavity. In this case, the one or more electrodes 312, 314 may be associated with a device configured to be implanted remote from the controller 302 and to provide signals sensed by the electrodes to the controller through a wireless communication link.

The cardiac event source 306 may also be a motion sensor 316 configured to be positioned on or near a diaphragm to sense motion of the heart or to sense heart sounds, and to output electrical signals representative of such motion. Alternatively, the motion sensor 316 may be configured to be positioned in, on, or adjacent to an intrathoracic structure, e.g. heart, pericardium, great artery and vein, within the intrathoracic cavity. In this case, the motion sensor 316 may be associated with a device configured to be implanted remote from the controller 302 and to provide signals sensed by the motion sensor to the controller through a wireless communication link. In either case, the motion sensor 316 may be, for example, an accelerometer (such as a multi-axial e.g., three-dimensional, accelerometer) that provides signal related to heart movement, or an acoustic transducer that provides signal related to heart sounds.

The pressure measurement source 308 is configured to provide signals to the controller 302 that represent one or more pressures within the intrathoracic cavity. "Pressures within the intrathoracic cavity" may include an intrathoracic pressure obtained directly through a pressure sensor placed in the open space of the intrathoracic cavity and outside of any intrathoracic structures, e.g. heart, pericardium, great arteries and veins, within the cavity. "Pressures within the intrathoracic cavity" may also include a measure of intrathoracic pressure obtained indirectly, for example, through an accelerometer placed outside of the intrathoracic cavity that provides a measure indicative of, or correlated with, intrathoracic pressure. "Pressures within the intrathoracic cavity" may also include pressures associated with intrathoracic structures like the heart, pericardium, great arteries and veins. For example, these "pressures within the intrathoracic cavity" may include right atrial pressure, right ventricular pressure, left ventricular pressure, and aortic pressure.

The pressure measurement source 308 may be one or more pressure sensors 318 configured to be positioned in the open space of the intrathoracic cavity, or in, on, or adjacent an intrathoracic structure, e.g. heart, pericardium, great artery and vein, within the cavity, and configured to output electrical signals representative of pressure. To these ends, the one or more pressure sensors 318 may be directly coupled to the controller 302, or alternatively, associated with a device configured to be implanted remote from the controller 302 and to provide signals sensed by the one or more pressure sensors to the controller through a wireless communication link.

Direct coupling between the one or more pressure sensors 318 and the controller 302 may be appropriate when the IMD 300 is implanted on the superior side of the patient's diaphragm at a superior implant location 122, such as shown in FIG. 1. When implanted in this location, pressure sensors 318 directly coupled to the controller 302 would be placed in the open space of the thoracic cavity 102. Remote coupling between the one or more pressure sensors 318 and the controller 302 may be appropriate when the IMD 300 is implanted on the inferior side of the patient's diaphragm at an inferior implant location 120, such as shown in FIG. 1. When implanted in this location, one or more pressure sensors 318 separately implanted in the intrathoracic cavity and remotely coupled to the controller 302 may provide pressure signals. For example, the pressure sensor 318 may be included in a device configured to be implanted: 1) in the right atrium to obtain right-atrial pressure signals, 2) in the right ventricle to obtain right ventricular pressures, 3) in the right ventricle to obtain surrogates of pulmonary artery pressure, or 4) within the pulmonary artery itself.

The pressure measurement source 308 may also be a motion sensor 320 configured to provides signals indicative of, or that correlate to, intrathoracic pressure. For example, the motion sensor 320 may be an accelerometer configured to be positioned on or near a diaphragm to sense motion of the diaphragm, and to output electrical signals representative of such motion to the controller 302. As will be described further below, fluctuations in these electrical signals correlate to changes in intrathoracic pressure associated with respiration cycles. The motion sensor 320 may also be an accelerometer or acoustic transducer configured to be positioned within the patient to sense sounds associated with cardiac function, and to output electrical signals representative of such sounds. As will be described further below, fluctuations in these electrical signals correlate to changes in intrathoracic pressure associated with respiration cycles. Alternatively, the motion sensor 320 may be an impedance/conductance sensor in the form of a pair of electrodes configured to be positioned in or on the diaphragm, and to output electrical signals representative of impedance or conductance of diaphragm tissue. Fluctuations in impedance or conductance correlate to changes in expansion and contraction of the diaphragm, which in turn correlate to changes in intrathoracic pressure associated with respiration cycles.

The stimulation delivery mechanism 310 is configured to apply stimulation to the diaphragm to cause a partial contraction of the diaphragm. A partial contraction typically entails a very short (only a few tens of milliseconds) pulse-like, biphasic (singular-caudal followed by singular-cranial) asymptomatic motion of the diaphragm. The stimulation is characterized by a set of stimulation parameters that induce a partial contraction of the diaphragm that does not affect respiration. More specifically, the stimulation is configured such that the diaphragm does not contract to a level that induces inspiration. The stimulation delivery mechanism 310 may be one or more electrodes 322, 324 configured to be positioned on or near a diaphragm to deliver electrical stimulation pulses to the diaphragm.

Considering the controller 302 in more detail, the cardiac signal module 328 of the controller receives signals from the cardiac event source 306 and is configured to process the signals to detect cardiac events of interest. For example, as will be described further below, the cardiac signal module 328 may be configured to detect one or more of an electrical cardiac event, such as a ventricular depolarization represented by an R-wave, and 2) a mechanical cardiac event, such as a ventricular contraction represented by an S1 sound. Information corresponding to detected cardiac events is provided to the therapy module 340, which in turn processes the cardiac-event information to determine or adjust one or more parameters of a stimulation therapy.

With respect to electrical cardiac events, the cardiac signal module 328 may include an electrogram (EGM) analysis module 332 adapted to receive electrical signals from the electrodes 312, 314 and to process the electrical signals to detect cardiac events of interest. For example, referring to FIG. 4A, the EGM analysis module 332 may be configured to process a cardiac electrical activity signal 402, e.g., an EGM signal, to detect cardiac events 404, 406 corresponding to atrial events 404, such as P waves, or ventricular events 406, such as R waves, QRS complexes, or T waves.

Regarding mechanical cardiac events, the cardiac signal module 328 may include a heart motion/sounds analysis module 334 for analyzing mechanical motion of the heart. The heart motion/sounds analysis module 334 is adapted to receive signals from the motion sensor 316 and to detect a cardiac event of interest. As previously mentioned, the motion sensor 316 may be, for example, an accelerometer or acoustic transducer, configured to sense a variety of mechanical and sound activities, such as diaphragm motion and heart sounds. Heart sound signals obtained through the accelerometer may be processed by the heart motion/sounds analysis module 334 to detect cardiac events. For example, referring to FIG. 4B, the heart sound signals 420, 422 exhibit recurring sound events 424, 426 that correspond in time with recurring cardiac contractions 428, such as those included in the EGM signal 440. More specifically, the onset of sound events 424, 426 coincide with ventricular contractions 428.

The pressure signal module 330 of the controller 302 receives signals from the pressure measurement source 308 and is configured to process the signals for purposes of detecting a pressure event of interest or deriving a pressure measure of interest. For example, regarding measures of interest, the pressure signal module 330 may process signals from a pressure sensor 318 to determine pressure measurements under different therapy conditions, e.g., with diaphragmatic stimulation on, and with diaphragmatic stimulation off, or under different stimulation settings. The pressure signal module 330 may also process signals from a pressure sensor 318 to determine pressure measurements at different times, e.g., at or near delivery of a stimulation pulse, and at or near an occurrence of a particular cardiac event. Regarding events of interest, the pressure signal module 330 may process signals from a motion sensor 320 to detect respiration cycles and to identify one or more events of interest within the cycle, such as end inspiration. Information corresponding to detected events of interest and measures of interest, collectively referred to as pressure information, is provided to the therapy module 340. The therapy module 340, in turn, processes the pressure information to determine whether an adjustment to one or more parameters of a stimulation therapy is warranted.

Regarding the processing of signals from a pressure sensor 318, the pressure signal module 330 may include a pressure measurement module 336 for analyzing pressures within the intrathoracic cavity. The pressure measurement module 336 is adapted to receive signals from the pressure sensor 318. As previously described, the pressure sensor 318 may be a configured to be placed in the open space of the intrathoracic cavity and outside of any intrathoracic structures, e.g. heart, pericardium, great arteries and veins, within the cavity—to thereby provide a signal representing intrathoracic pressure. Alternatively, the pressure sensor 318 may be configured to be placed in, on, or adjacent an intrathoracic structure, e.g. heart, pericardium, great artery and vein, within the cavity. For example, the pressure sensor 318 may be configured to be placed in, on, or adjacent to one of the right atrium, the right ventricle, the left ventricle, the aorta, and the pulmonary artery—to thereby provide a corresponding signal presenting right atrial pressure, right ventricular pressure, left ventricular pressure, aortic pressure, or pulmonary artery pressure.

The pressure measurement module 336 is further adapted to process signals obtained from the pressure sensor 318 to derive pressure measures of interest. Referring to FIG. 4C (which illustrates various waveforms representing different pressures within the intrathoracic cavity under conditions of no diaphragmatic stimulation 450 and diaphragmatic stimulation 452), data defining a waveform may be processed to obtain a pressure measurement at or near a fiducial point (indicated by an asterisk) that is associated with a cardiac event. For example, the fiducial point may coincide with the cardiac event or it may be a time offset from the cardiac event. The cardiac event may relate to a ventricular depolarization, and may be a Q wave onset 454 or an R wave 456.

Continuing with FIG. 4C, a waveform representing the intrathoracic pressure 458 may be processes to obtain a pressure at the fiducial point (indicated by an asterisk) that coincides with a R wave 456. This pressure measurement derived from the intrathoracic pressure waveform 458 may correspond to the amplitude of the waveform at the peak 460, where the amplitude may correlate to a pressure measurement in millimeters of mercury (mmHG). Alternatively, the pressure measurement may correspond to the area under the intrathoracic pressure waveform 458 on either side of the peak 460, bound by the dashed horizontal line.

The pressure measurement is provided to the therapy module 340, where it is further processed to determine if stimulation therapy may be improved to provide a more desirable outcome. For example, as will be described below referring to FIG. 5A, different measures of intrathoracic pressure may be obtained for different stimulation therapies, each defined by a different set of stimulation parameter values, to determine which set of stimulation parameters provides the best measure of intrathoracic pressure. In another example, as will be described further below referring to FIG. 6B, the measure of intrathoracic pressure may be compared to a predetermine threshold value, to determine if one or more of the stimulation parameters should be adjusted in an attempt to obtain, or at least more closely approach, the threshold value.

Continuing with FIG. 4C, data defining a waveform representing right atrial pressure 462 may be processed to obtain a pressure measurement at or near a fiducial point (indicated by an asterisk) offset in time from a R wave 456. The amount of offset is selected to provide a measure of right atrial pressure at or near a midpoint of systole. The pressure measurement derived from the right atrial pressure waveform 462 may correspond to the amplitude of the waveform at the peak 464, where the amplitude may correlate to a pressure measurement in millimeters of mercury (mmHG). Alternatively, the pressure measurement may correspond to the area under the right atrial pressure waveform 462 on either side of the peak 464, bound by the dashed horizontal line Likewise, data defining waveforms representing each of right ventricular pressure 466, aortic pressure 470, and left ventricular pressure 474, 478 may be processed to obtain respective pressure measurements at or near a fiducial point (indicated by an asterisk) associated with a ventricular depolarization. Each of these pressure measurements may correspond to the amplitude of the waveform at its peak 468, 472, 476, and 480, or an area under the waveform.

Regarding the processing of signals from a motion sensor 320, the pressure signal module 330 may include a diaphragm motion and heart sounds analysis module 338 for analyzing one or more of motion of the diaphragm and sounds associated with the heart. The diaphragm motion and heart sounds analysis module 338 is adapted to receive signals from the motion sensor 320 and to detect a pressure event of interest. As previously described, the motion sensor 320 may be an accelerometer configured to be positioned on or near a diaphragm to sense motion of the diaphragm. The motion sensor 320 may also be an accelerometer or an acoustic transducer configured to be positioned within the patient to sense sounds associated with cardiac function, and to output electrical signals representative of such sounds. Alternatively, the motion sensor 320 may be an impedance/conductance sensor in the form of a pair of electrodes configured to be positioned in or on the diaphragm.

Referring to FIG. 4A, the diaphragm motion and heart sounds analysis module 338 may be configured to process an electrical signal 408 obtained from a motion sensor 320 in the form of an accelerometer or an impedance/conductance sensor, to detect fluctuations in these electrical signals that correlate to changes in intrathoracic pressure associated with respiration cycles. For example, the diaphragm motion and heart sounds analysis module 338 may be configured to process an accelerometer signal to detect respiration events 410, 412, such as the point of end inspiration 410 or the point of end expiration 412. As described further below, the pressure signal module 330 may output a detection of end inspiration 410 to the therapy module 340, which in turn may adjust stimulation therapy either by withholding the delivery of a stimulation pulse that would otherwise coincide, or at least partially overlap, with end inspiration, or by adjusting a stimulation parameter of the stimulation pulse to be delivered at or near end inspiration.

Figure 4B:
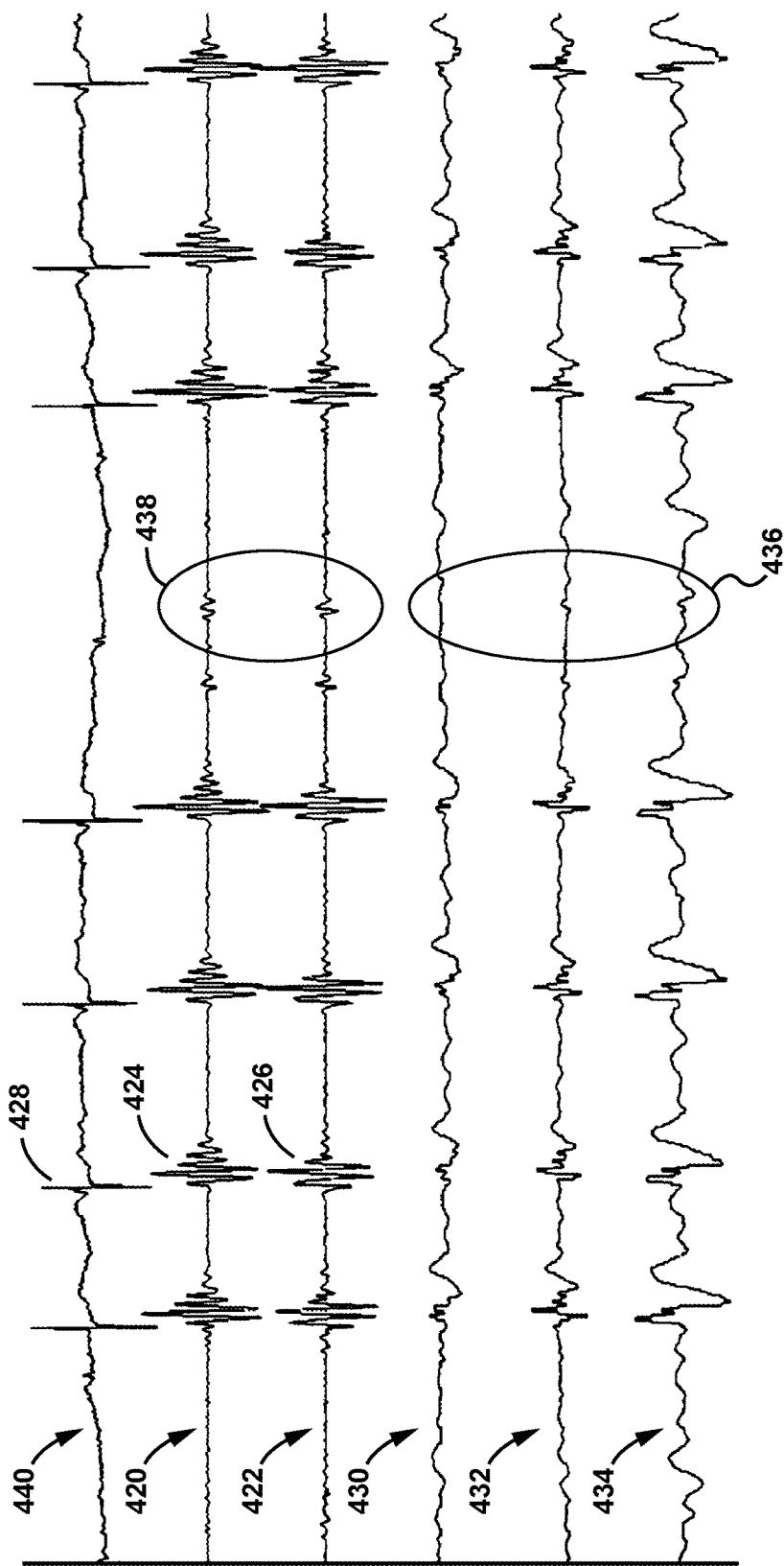
FIG. 4B are waveforms representing—from top to bottom—a cardiac electrical activity signal, a pair of heart sound signals, and movement signals of the diaphragm in each of three different direction.
Figure 4C:
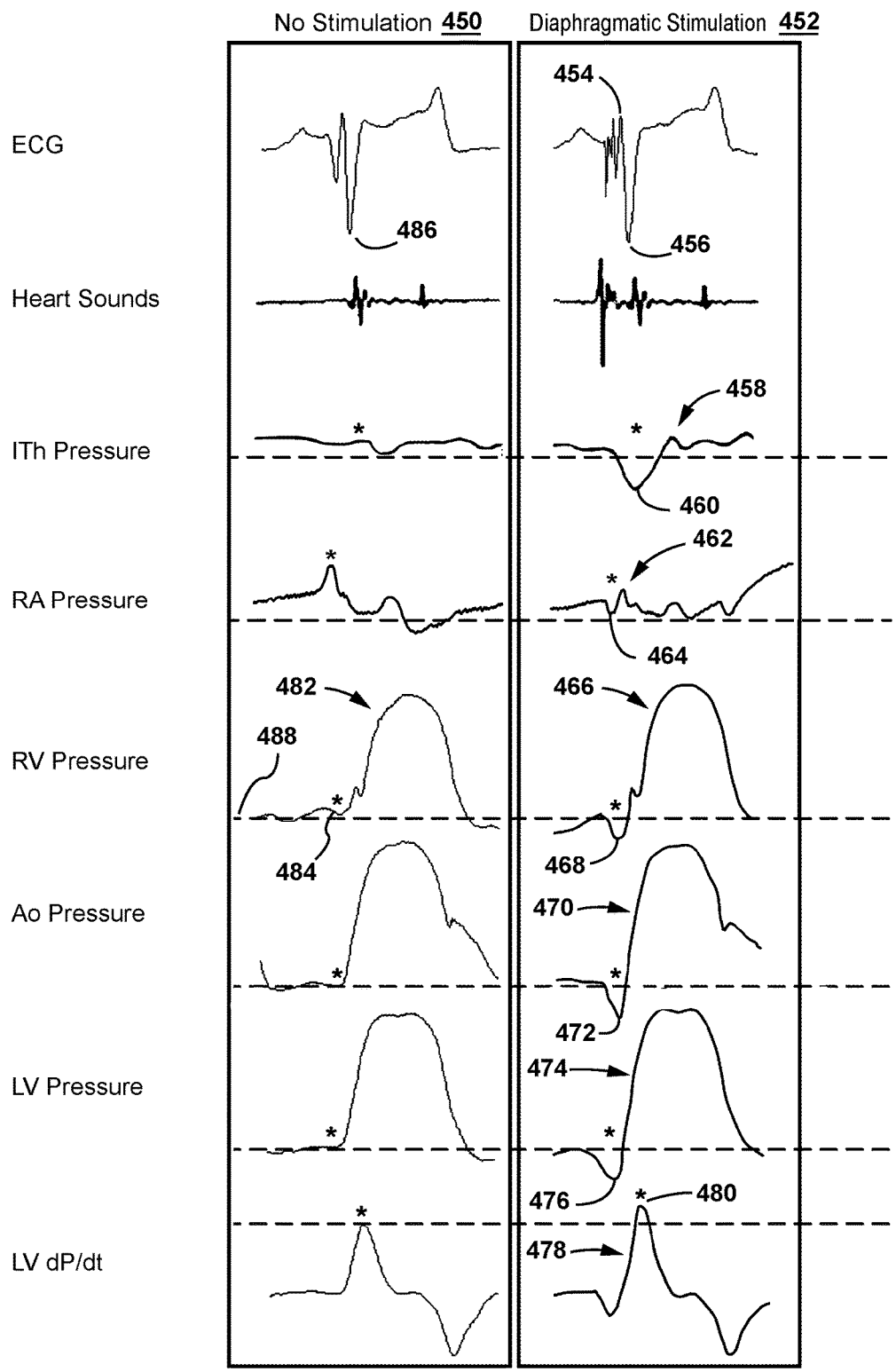
FIG. 4C are illustrations that provide a side-by-side comparison between waveforms of various physiological signals, with the left side representing baseline signals resulting when diaphragmatic stimulation is not delivered, and the right side representing signals resulting from a delivery of diaphragmatic stimulation.

Referring to FIG. 4B, the diaphragm motion and heart sounds analysis module 338 may be configured to process electrical signals obtained from a motion sensor 320 in the form of a three-dimensional accelerometer to derive signals 430, 432, 434, corresponding to acceleration of the diaphragm along each of an x, y, and z axis. The acceleration signals 430, 432, 434 may be further processed by the diaphragm motion and heart sounds analysis module 338 to sense the respiration cycle and respiration rate of the patient, and to detect an event of interest within the respiration cycle. For example, the diaphragm motion and heart sounds analysis module 338 may be configured to identify respiration cycles based on changes in amplitude of the acceleration signals 430, 432, 434 and to detect the end inspiration region 436 of a respiration cycle within any of the motion signals as the region of greatest attenuation in the respective signal.

With continued reference to FIG. 4B, the diaphragm motion and heart sounds analysis module 338 may be configured to process electrical signals 420, 422 obtained from a motion sensor 320 in the form of an accelerometer or acoustic transducer implanted within the patient to obtain signals corresponding to different heart sounds. For example, signals corresponding to heart sound S1 may be obtained based on signals 420, 422 sensed by an accelerometer or by an acoustic transducer. Similar to the motion signals, the heart sound signals may be further processed by the diaphragm motion and heart sounds analysis module 338 to sense the respiration cycle and respiration rate of the patient, and to detect particular events of interest within the respiration cycle. For example, the diaphragm motion and heart sounds analysis module 338 may be configured to identify respiration cycles based on changes in amplitude in the heart sound signals 420, 422 and to detect the end inspiration region 438 of a respiration cycle within either of the heart sound signals as the region of greatest attenuation in the respective signal.

Regarding the therapy module 340, it includes a cardiac-event analysis module 342, a pressure analysis module 344, and a pulse generator 346. The pulse generator 346 is configured to output stimulation therapy to the stimulation delivery mechanism 310. The stimulation therapy may be in the form of electrical stimulation, in which case the therapy may be delivered through electrodes 322, 324.

The stimulation therapy output by the pulse generator 346 is defined by one or more stimulation parameters. For electrical stimulation, the parameters may include: 1) one or more pulse parameters having a value or setting selected to define a stimulation pulse that induces a partial contraction of the diaphragm, and 2) a timing parameter that controls the timing of the delivery of one or more stimulation pulses. The pulse parameters may include, for example, a pulse waveform type, a pulse amplitude, a pulse duration, and a pulse polarity. The timing parameter may include one or more of a delay period that defines a time between a detected cardiac event and a delivery of an electrical stimulation pulse, and a stimulation rate that defines a time interval between a series of stimulation pulses.

A delay period may be relevant in implementations where stimulation therapy in the form of a single stimulation pulse, is delivered, on a heart-beat-by-heart-beat basis, in response to a detection of a cardiac event. Such implementations, which may allow for adjustments in delay period on a beat-by-beat basis, are described in detail in U.S. Patent Application Publication No, 2017/0021166, titled Systems, Devices, and Methods for Improving Hemodynamic Performance Through Asymptomatic Diaphragm Stimulation, the disclosure of which is hereby incorporated by reference.

A stimulation rate may be relevant to implementations where stimulation therapy in the form of a series of stimulation pulses, is delivered at a fixed rate, which rate is periodically adjusted based on changes in the patient's heart rate. In a rate implementation, therapy delivery is not necessarily triggered on a beat-by-beat basis by detection of cardiac events. Instead, a rate is determined and therapy is delivered in accordance with the determined rate until a change in patient heart rate is detected.

One or more of the stimulation parameters, including timing parameters and pulse parameters, may be adjusted by the therapy module 340. With respect to timing parameters, as previously mentioned, the rate of electrical stimulation may be adjusted in response to changes in the heart rate of the patient. Accordingly, the rate of delivery of electrical stimulation pulses may range, for example, between 30 pulses per minute (ppm) and 180 ppm, with a typical rate being around 60 ppm. Likewise, a delay period between a detected cardiac event and a delivery of an electrical stimulation pulse may be adjusted based on a running average of time intervals between detected cardiac events. Regarding pulse parameters, the pulse amplitude may be set to a value between 0.0 volts and 7.5 volts, and the pulse width may be set to a value between 0.0 milliseconds and 1.5 milliseconds. The amplitude may be adjusted, for example, in increments of between 0.1 to 0.5 volts, while the pulse width may be adjusted in increments of between 0.1 to 1.5 milliseconds. The polarity may be changed between a positive polarity and a negative polarity, and the waveform type may be changed from mono-phasic to biphasic, or from a square to a triangular, sinusoidal or sawtooth waveform.

The cardiac-event analysis module 342 is configured to receive cardiac-event information from the cardiac signal module 328 and to process the information to determine the timing parameter. To this end, in one configuration, the cardiac-event analysis module 342 determines a time, relative to a detected cardiac event, at which to deliver a stimulation pulse to the diaphragm. The determined time, referred to as a delay period, may be selected so that the stimulation pulse is delivered just prior to the next expected occurrence of the cardiac event.

The delay period may be based on the time between successive detected cardiac events. For example, the EGM analysis module 332 of the cardiac signal module 328 may be configured to detect ventricular events, e.g., R waves, and to output such detections to the therapy module 340. The cardiac-event analysis module 342 may process the detected ventricular events to determine a statistical measure of time between a number of pairs of successive ventricular events. The cardiac-event analysis module 342 may then determine a delay period based on the statistical measure and an offset relative to the statistical measure, and control the pulse generator 346 to output stimulation pulses based on the determined delay period. The delay period times the delivery of the stimulation pulses to occur either just prior to, or just after, a detection of a particular cardiac event. Details related to the determining of the delay period are provided in U.S. Patent Application Publication No, 2017/0021166, titled Systems, Devices, and Methods for Improving Hemodynamic Performance Through Asymptomatic Diaphragm Stimulation, the disclosure of which is hereby incorporated by reference.

The stimulation rate may also be based on the time between successive detected cardiac events. The EGM analysis module 332 of the cardiac signal module 328 may be configured to detect ventricular events, e.g., R waves, and to output such detections to the therapy module 340. The cardiac-event analysis module 342 may process the detected ventricular events to determine a statistical measure of time between a number of pairs of successive ventricular events. The cardiac-event analysis module 342 may then determine a stimulation rate based on the statistical measure. For example, the statistical measure may be the average time between successive detected cardiac events. Details related to the determining of the stimulation rate are provided below referring to FIG. 7.

The pressure analysis module 344 of the therapy module 340 is configured to receive pressure information, including one or more of a measure of interest, e.g., a pressure measurement, or an event of interest, e.g., end inspiration of a respiration cycle, from the pressure signal module 330. The pressure analysis module 344 is further configured to process the received pressure information to determine if an adjustment of a stimulation parameter is warranted.

In one configuration, the pressure analysis module 344 may receive pressure information corresponding to a measure of interest, and may evaluate the measure of interest against a baseline measure of interest. For example, as previously described referring to FIG. 4C, the received measure of interest may be a measure of an intrathoracic pressure, RA pressure, RV pressure, Ao pressure, or LV pressure at a fiducial point. The pressure analysis module 344 may compare the received measure of interest to the baseline to determine if the comparison outcome is acceptable. If the comparison outcome is not acceptable, the therapy module 340 may adjust one or more stimulation parameters for future stimulation therapy to eventually arrive at a stimulation therapy that results in an acceptable outcome. Details related to algorithms for adjusting stimulation parameters acceptable based on pressure measurements and determining if comparison outcomes are acceptable, are provided below referring to FIG. 6B and FIG. 6D.

In another configuration, the pressure analysis module 344 may receive pressure information corresponding to an occurrence of a pressure event of interest. The pressure event of interest may, for example, relate to respiration cycles of a patient and may be a point of end inspiration within a respiration cycle. In response to the receipt of such pressure information, the pressure analysis module 344 may determine to withhold stimulation therapy or to change one or more stimulation parameters. Details related to algorithms for adjusting stimulation parameters based on occurrences of pressure events are provided below referring to FIG. 6C and FIG. 6E.

The controller 302 includes a memory subsystem 348. The memory subsystem 348 is coupled to the cardiac signal module 328 and the pressure signal module 330, and may receive and store data representative of sensed EGMs, sensed intrathoracic cavity pressure, heart sounds, and sensed cardiovascular pressures, e.g., right ventricular pressures, left ventricular pressure, right atrial pressure, and aortic pressure. The memory subsystem 348 is also coupled to the therapy module 340 and may receive and store data representative of delivered stimulation therapies, including their associated sets of stimulation parameters and times of delivery.

The controller 302 also includes a communication subsystem 350 that enables communication between the controller and other components. These other components may form part of the IMD 300, such an a separately implanted pressure sensor within the intrathoracic cavity, may be separate from the IMD, such as an external programmer used by a physician to program the IMD. The communication subsystem 350 may include a telemetry coil enabling transmission and reception of signals, to or from an external apparatus, via inductive coupling. Alternative embodiments of the communication subsystem 350 could use an antenna for an RF link, or a series of low amplitude high frequency electrical pulses emitted by the sensor that do not illicit muscle or nervous activation, detected by sensing electrodes of the stimulating IMD. The controller 302 also includes a power supply 352 that supplies the voltages and currents necessary for each module of the controller, and a clock supply 354 that supplies the modules with any clock and timing signals.

Regarding the physical structure of the IMD 300, while the foregoing functional description of the IMD describes separate pairs of electrodes 312, 314 and 322, 324, respectively associated with the cardiac event source 306 and the stimulation delivery mechanism 310, a configuration of the IMD may include a single pair of electrodes configured to perform dual functions. That is, the IMD 300 may include a single pair of electrodes configured to both sense cardiac electrical activity and to deliver electrical stimulation. In this configuration, the controller 302 may include an electrode interface that is configured to switch the connection of the electrodes between the cardiac event source 306 and the stimulation delivery mechanism 310 as needed. The electrode interface may also provide other features, capabilities, or aspects, including but not limited to amplification, isolation, and charge-balancing functions, that are required for a proper interface between the electrodes and diaphragm tissue.

Similarly, the respective functions of the separate motion sensors 316, 320 referenced with respect to the cardiac event source 306 and the pressure measurement source 308 may be provided by a single motion sensor shared by the different sources. In this configuration, the controller 302 may include sensor interface that is configured to switch the connection of the single sensor between the cardiac event source 306 and the pressure measurement source 308 if needed. The sensor interface may also provide other features, capabilities, or aspects, including but not limited to amplification, isolation, that are required for a proper interface between the sensor and diaphragm tissue.

Further regarding the physical structure of the IMD 300, in one configuration, referred to as a "leaded configuration," the electrodes are coupled to the controller 302 through a lead. In another configuration, referred to as a "leadless configuration," the electrodes may be located directly on the housing 304. In a leaded configuration, a motion sensor may be included as part of a lead, which lead may be the same lead that includes the electrodes. Alternatively, the motion sensor may be included as part of the housing 304, and may be either within the housing or on the exterior of the housing. In the leadless configuration, the motion sensor is included as part of the housing 304, and again may be either within the housing or on the exterior of the housing. These different configurations are described further below referring to FIGS. 8 and 10.

Optimization and Therapy Adjustment Algorithms

Having thus described the structural components of an IMD 300, and their respective functions, a description of several algorithms implemented by the IMD are described. A first of these algorithms relates to optimizing stimulation therapy for a patient through the delivery of stimulation therapy using different stimulation parameter values or settings, the obtaining of physiological measures resulting from these different stimulations, and the processing of the obtained measures to identify an optimal stimulation therapy. The second of the algorithms relates to stimulation therapy adjustment based on real-time or near real-time measure feedback.

Optimization

Figure 5A:
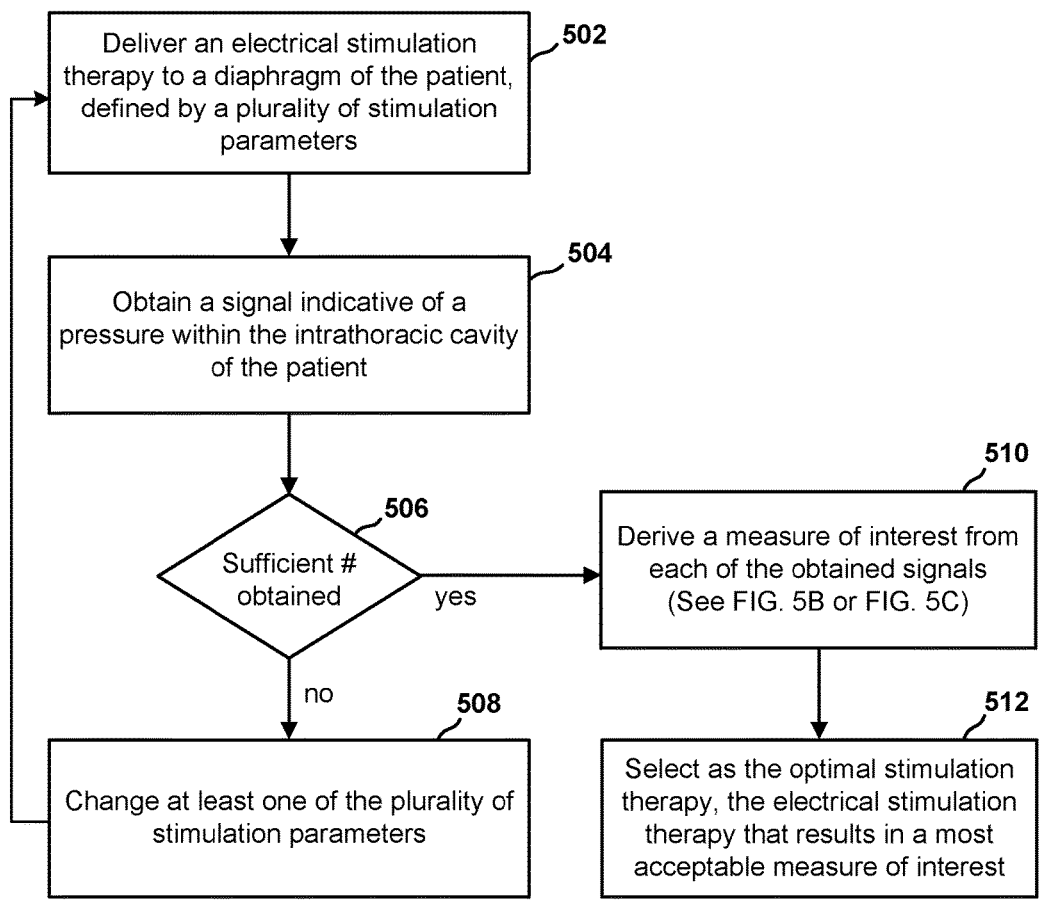
FIG. 5A is a flow chart of a method of optimizing stimulation therapy for a patient based on measures of interest derived from one of pressure signals or heart sound signals.

FIG. 5A is a flow chart of a method of determining an optimal stimulation therapy for a patient having an IMD 300. As used herein, an optimal stimulation therapy is one that results in improved hemodynamic functioning of the patient's heart. Such improved hemodynamic functioning may be characterized, for example, by increased ejection fraction or increased contractility of the heart, changes to venous filling volumes to match the optimal point of contractile efficiency for one or more cardiac chambers, or increased stroke volume for each cardiac beat, decreased autonomic tone and subsequent systemic vascular resistance. The optimal stimulation therapy is defined by a plurality of stimulation parameters, each programmed to a value or setting.

As described below, the method may be performed entirely by the IMD 300. For example, the IMD 300 may be programmed to periodically, e.g., once a day, perform the method to ensure an optimal stimulation therapy is being delivered to the patient. Alternatively, in order to conserve energy expenditure by the IMD 300, the method may be performed by the IMD in conjunction with an external device. In this implementation, the IMD 300 may perform processes including the delivering of stimulation therapy using different stimulation parameters and the collecting and storing of data related to physiological measures. The stored data may be subsequently uploaded to an external device, such as a remote processor. The external device processes the data to obtain the physiological measures, and then processes the obtained measures to identify an optimal stimulation therapy defined by a plurality of stimulation parameters, each programmed to a value or setting. The remote processor may then communicate with the IMD 300 to reprogram the IMD with the optimal stimulation therapy.

In the method of FIG. 5A, signals indicative of pressures within the intrathoracic cavity of a patient are obtained while differently configured stimulation therapies are delivered to a patient. The signals are processed to derive measures of interest that reflect hemodynamic performance of the heart. For example, measures of left ventricular pressure at a particular time of a cardiac cycle corresponding to ventricular depolarization may be derived. In another example, measures of electromechanical activation time (EMAT), which may be defined as the time from the onset of the Q wave in a cardiac electrical signal to the closure of the mitral value within a S1 heart sounds, may be derived. In another example, measures of left ventricular contractility are derived by a maximum value corresponding to systole when blood is ejected from the left ventricle into the aorta corresponding to LV $dP/dt_{max}$. Like derived measures are then compared to each other to determine which variation of the stimulation therapy resulted in the best hemodynamic performance.

In the example of LV pressure at ventricular electrical depolarization corresponding to the end of left ventricular filling (diastole), the best hemodynamic performance would result from the stimulation therapy that provides the minimum LV pressure. With respect to EMAT, the best hemodynamic performance would result from the stimulation therapy that provides the minimum EMAT. With respect to left ventricular contractility, the best hemodynamic performance occurs when either the value or the derivative of left ventricular pressure is at a maximum value during an immediate duration of time following ventricular electrical depolarization.

Continuing with FIG. 5A, at block 502, the IMD 300 delivers an electrical stimulation therapy to a diaphragm of the patient. Modules of the IMD 300 involved in the delivery of electrical stimulation may include the therapy module 340 and the stimulation delivery mechanism 310. As described above referring to FIG. 3, the therapy module 340 generates the electrical stimulation therapy in accordance with one or more pulse parameters, and provides the therapy to the stimulation delivery mechanism 310 in accordance with a timing parameter. The stimulation delivery mechanism 310, in turn, applies the stimulation therapy to the diaphragm.

The electrical stimulation therapy delivered by the IMD 300 is defined by stimulation parameters that include: 1) one or more pulse parameters having a value or setting selected to define a stimulation pulse that induces a partial contraction of the diaphragm, and 2) a timing parameter that controls the timing of the delivery of one or more stimulation pulses. The pulse parameters may include, for example, a pulse waveform type, a pulse amplitude, a pulse duration, and a pulse polarity. The timing parameter may include one or more of a delay period that defines a time between a detected cardiac event and a delivery of an electrical stimulation pulse, and a stimulation rate that defines a time interval between a series of stimulation pulses.

At block 504, the IMD 300 obtains a signal indicative of a pressure within the intrathoracic cavity of the patient. Such a signal may be a pressure signal that provides a direct measure of a pressure within the intrathoracic cavity. For example, direct measures of intrathoracic pressure, right atrial pressure, right ventricular pressure, left ventricular pressure, aortic pressure, and pulmonary artery pressure may be obtained. Alternatively, a signal indicative of a pressure within the intrathoracic cavity may be a motion signal or a sound signal. While these signals may not provide a direct measure of pressure, they are affected by changes in intrathoracic pressure and thus provide indirect, or surrogate measures of pressure within the intrathoracic cavity. Modules of the IMD 300 involved in obtaining a signal indicative of a pressure of the intrathoracic cavity may include the pressure measurement source 308 and the pressure measurement module 336.

Referring to FIG. 3, the pressure measurement source 308 may be one of a pressure sensor 318 or a motion sensor 320 configured to be associated with the intrathoracic cavity, or with a cardiovascular structure within the intrathoracic cavity. The cardiovascular structure may be a right atrium, a right ventricle, a left ventricle, an aorta, and a pulmonary artery. Depending on where it is located, a pressure sensor 318 may provide a signal corresponding to the pressure within the intrathoracic cavity, or to the pressure within a cardiovascular structure within the intrathoracic cavity. Depending on its configuration and location, a motion sensor 320 may provide a signal corresponding to diaphragm motion or heart sounds. For example, a motion sensor 320 in the form an accelerometer and placed in contact with the diaphragm provides signals corresponding to diaphragm motion, such as those represented by waveforms 430, 432, 434 in FIG. 4B. A motion sensor 320 in the form of an acoustic transducer and placed in contact with the diaphragm provides signals corresponding to heart sounds, such as those represented by waveforms 420, 422 in FIG. 4B.

The delivery of electrical stimulation therapy in block 502 and the obtaining of a signal in block 504 may occur over periods of different durations. In one implementation, the IMD 300 may be configured, e.g., programmed, to deliver therapy and obtain a signal for a duration corresponding to a single cardiac cycle. In other implementations, the IMD 300 may be configured to delivery therapy and obtain a signal for a period that encompasses a plurality of cardiac cycles. For example, such period may encompass at least one respiration cycle, which in turn encompasses multiple cardiac cycles. The IMD 300 may also be configured to deliver therapy and obtain a signal over a specified duration, such as between 10-20 seconds.

Continuing with FIG. 5A, at block 506, upon completion of an iteration of delivering stimulation therapy (block 502) and obtaining a signal (block 504), the IMD 300 determines whether a sufficient number of signals has been obtained to complete the optimization process. Modules of the IMD 300 involved in determining whether a sufficient number of signals has been obtained may include the therapy module 340. If a sufficient number of signals has not been obtained, the process proceeds to block 508, where the IMD 300 changes at least one of the plurality of stimulation parameters, and iterates or cycles through another round of delivery of electrical stimulation therapy (block 502) using the changed stimulation parameter, and obtaining a signal (block 504).

Whether a number of obtained signals is sufficient or not may depend on the stimulation parameters that define the electrical stimulation therapy, and which stimulation parameter is being considered or evaluated for adjustment. The IMD 300 may be configured to deliver stimulation and obtain signals for each of a number of different values of a particular parameter.

In the case of a timing parameter, the IMD 300 may scan through different values of a delay period, in increments of a specified duration. For a delay period corresponding to the time between an occurrence of a ventricular event, such as ventricular depolarization onset, and the delivery of electrical stimulation therapy to the diaphragm, the IMD 300 may scan through a delay-period range bound by a minimum period and maximum period, in a time increment. For example, for a minimum delay period of 0 milliseconds, meaning the stimulation therapy is delivered upon detection of the cardiac event, and a maximum delay period of 150 milliseconds, meaning stimulation therapy is delivered 150 milliseconds after detection of the cardiac event, the IMD 300 may scan though the range of 0 to 150 milliseconds in 10 millisecond increment. In another example, for a minimum delay period of −150 milliseconds, meaning the stimulation therapy is delivered 150 milliseconds before the occurrence of an upcoming, anticipated cardiac event, and a maximum delay period of 0 milliseconds, meaning stimulation therapy is delivered upon occurrence of an upcoming, anticipated cardiac event, the IMD may scan though the range of −150 to 0 milliseconds in 10 millisecond increment. In either case, a sufficient number of signals would be obtained after fifteen iterations of delivering and obtaining. In yet another example, the IMD 300 may scan through each of the foregoing ranges. In this case, a sufficient number of signals would be obtained after thirty iterations of delivering and obtaining.

In the case of a pulse parameter, the IMD 300 may scan through different values of a pulse amplitude or alternatively, a pulse width duration, in increments of a specified value. For example, for a pulse amplitude, the IMD 300 may scan through a pulse-amplitude range bound by a minimum value and a maximum value, in a voltage increment. For example, the IMD 300 may scan though the range of 0 to 7.5 volts in 0.1-0.5 volt increments. For a pulse duration, the IMD 300 may scan through a pulse-width duration range bound by a minimum value and a maximum value, in a time increment. For example, the IMD 300 may scan though the range of 0 to 5 milliseconds in 0.1-1.5 millisecond increments.

As previously mentioned, after a stimulation parameter has been changed in block 508, the process returns to block 502 where the IMD 300 delivers an electrical stimulation therapy in accordance with the changed parameter, and to block 504 where the IMD obtains at least one additional signal indicative of a pressure within the intrathoracic cavity of the patient. Throughout the iterative process of changing a stimulation parameter, delivering stimulation therapy, and obtaining a signal, the signal obtained is identical in each iteration. That is, if the signal obtained in the first iteration is an LV pressure signal, then the signal obtained in other iterations is also an LV pressure signal. Likewise, if the signal obtained in the first iteration is a heart sound signal, then the signal obtained in other iterations is also a heart signal. As described below, obtaining the same signal provides for derivation of same measures, which in turn, provides for comparisons among like measures for selection of optimal stimulation therapy.

Returning to block 506, if the IMD 300 determines that a sufficient number of signals has been obtained, the process proceeds to block 510, where a measure of interest is derived from each of the obtained signals. Depending on the type of obtained signal, different processes may be used to derive a measure of interest. Described below is a process for deriving a measure of interest from obtained pressure signals, and another process for deriving a measure of interest from obtained sound signals.

Figure 5B:
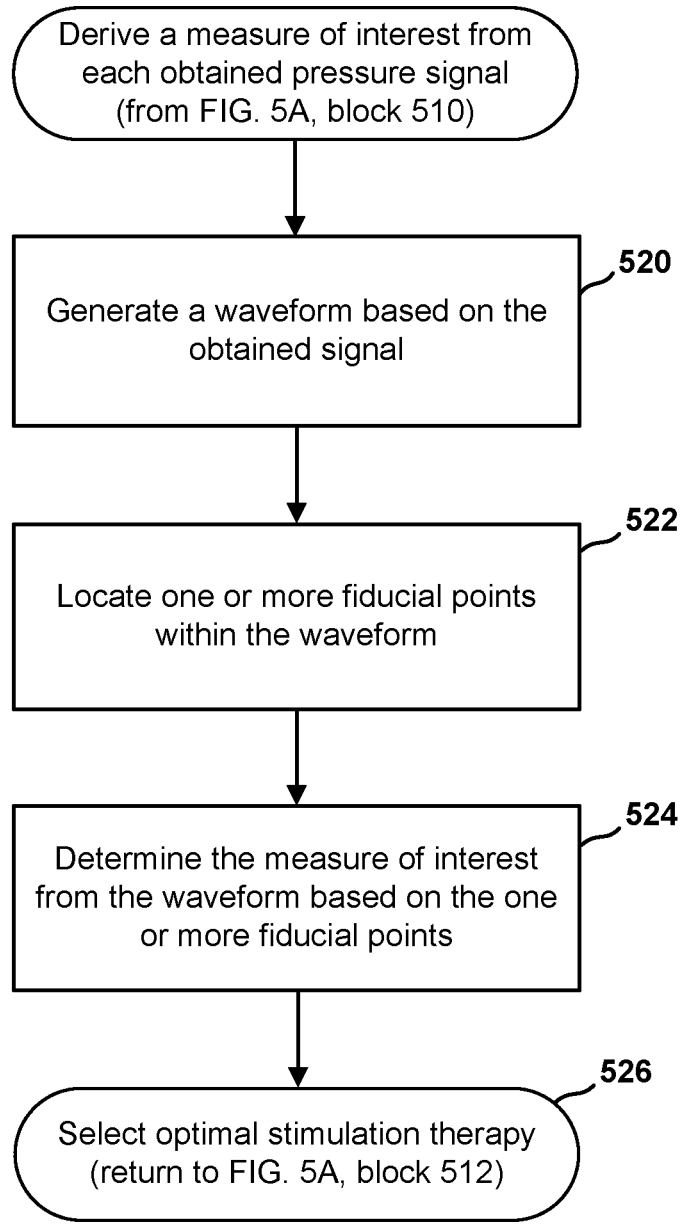
FIG. 5B is a flow chart of a method of deriving a pressure based measure of interest from pressure signals.

FIG. 5B is a detailed flow chart of a method of deriving a measure of interest from each obtained signal, as generally set forth in FIG. 5A, block 510, when the obtained signals are pressure signals. Modules of the IMD 300 involved in deriving a measure of interest may include the pressure signal module 330, the cardiac signal module 328, and the therapy module 340. Alternatively, the measure of interest may be derived by an external device. In the case of the latter, the IMD 300 is configured to store the signals it obtains and to transmit the signals to the external device.

At block 520, the IMD 300 may generate a waveform based on the obtained signal. In this regard, the waveform may be generated by the IMD 300 as a record of digital values with corresponding time stamps, where the digital values represent a measure. For example, the pressure measurement module 336 of the IMD 300 may be configured to convert signals from a pressure sensor 318 into records of pressure measurements with corresponding time stamps.

At block 522, the IMD 300 locates one or more fiducial points within the waveform. The fiducial point or points may be based on a cardiac event. For example, a fiducial point may correspond in time to a detected cardiac event, or may correspond to a time after a detected cardiac event. The detected cardiac event may be an electrical event, such as a ventricular depolarization, included in signals sensed by electrodes 312, 314. The detected cardiac event may be a mechanical event, such as a ventricular contraction, event in signals sensed by an accelerometer or an acoustic transducer.

The fiducial point varies depending on the region of interest in the hemodynamic cycle of the patient that is to be evaluated. If the region of interest is the beginning of systole or the end of diastole, the fiducial point may be the time at or very near an occurrence of a detected ventricular event. For example, such a fiducial point may correspond in time with a Q wave onset. If, however, the region of interest is the beginning of diastole, the fiducial point may be a time after the occurrence of a detected ventricular event. For example, such a fiducial point may be between 30-40% of the current cardiac cycle length of the patient. Accordingly, in a case of a patient with a heart rate of 60 bpm, which corresponds to a 1000 millisecond cycle length, the fiducial point may be 30-40 milliseconds after the detected ventricular event.

Referring to FIG. 4C, fiducial points for various waveforms are indicated by asterisks. Possible cardiac events and hemodynamic regions of interest to which these fiducial points correspond are summarized in Table 1.

TABLE 1

| Waveform | Cardiac Event (fiducial point) | Hemodynamic cycle region | Measure |
|---|---|---|---|
| intrathoracic (ITh) pressure 458 | R wave | end of diastole/ beginning of systole | pressure (mmHg) |
| right atrial (RA) pressure 462 | R wave offset | midpoint of systole | pressure (mmHg) |
| right ventricular (RV) pressure 466 | Q wave onset | end of diastole/ beginning of systole | pressure (mmHg) |
| aortic (Ao) pressure 470 | Q wave onset | end of diastole/ beginning of systole | pressure (mmHg) |
| left ventricular (LV) pressure 474 | Q wave onset | end of diastole/ beginning of systole | pressure (mmHg) |
| LV dP/dt 478 | 100-200 milliseconds following Q wave onset | Maximum value throughout entire cardiac cycle | pressure (mmHg/s) |

At block 524, the IMD 300 determines the measure of interest from the waveform based on one or more fiducial points. In one configuration, the measure of interest corresponds to a pressure measurement determined from the waveform at a single fiducial point within a cardiac cycle.

For example, referring to the RV pressure waveform 466 in FIG. 4C, the measure of interest may be a pressure measurement derived from the amplitude 468 of the waveform at the fiducial point (indicated by the asterisk), which fiducial point may correspond in time with an occurrence of a detected Q wave onset 454. In an implementation of this process, the therapy module 340 of the IMD 300 may obtain cardiac-event information from the cardiac signal module 328 including a time of occurrence of the Q wave onset 454. Based on this time information, the therapy module 340 reviews the pressure waveform information, e.g., the record of pressure measurements with corresponding time stamps, to locate the pressure measurement that matches the time of occurrence of the Q wave onset.

In another configuration, the measure of interest corresponds to a statistical pressure measurement, e.g., an average measurement, determined from a plurality of individual pressure measurements obtained over a period of time. In this case, respective pressure measurements are determined from the pressure waveform at each of a plurality of fiducial points. Each of the plurality of fiducial points correspond to a same point within a different cardiac cycle. For example, referring again to the RV pressure waveform 466 in FIG. 4C, a number of individual pressure measurements derived from the amplitude 468 of the waveform, over a corresponding number of cardiac cycles may be obtained at the same fiducial point in each cardiac cycle. In one configuration, the number of individual measures obtained and used to determine the overall measure of interest is enough to encompass at least one respiration cycle. In this manner, the effects of respiration on the pressures within the intrathoracic cavity are accounted for.

At block 526 the process returns to block 512 of FIG. 5A. At block 512, the IMD 300 selects as the optimal stimulation therapy, the electrical stimulation therapy that results in a most acceptable measure of interest. What constitutes a most acceptable measure of interest may depend on the stimulation parameter that was changed or adjusted in block 506 to obtain the measures of interest.

If the stimulation parameter being changed was a timing parameter, such as a delay period between a detection of a cyclic cardiac cycle event and a delivery of electrical stimulation, or a stimulation rate defining a set rate at which electrical stimulation pulses are delivery, the most acceptable measure of interest may be the measure of interest that deviates from a baseline measure of interest, or baseline value, by a greatest amount. The baseline value may be a measure of interest derived from a pressure signal obtained in the absence of diaphragmatic electrical stimulation therapy.

For example, referring to FIG. 4C, a baseline value of RV pressure may be derived from an RV pressure waveform 482 generated from a pressure signal obtained in the absence of diaphragmatic stimulation. The baseline value corresponds to a RV pressure derived from the peak 484 of the waveform 482 at the fiducial point (indicated by an asterisk) that coincides with a R wave 486. The fiducial point from which the baseline value is derived is the same as the fiducial point from which the obtained measures of RV pressure are derived. Alternatively, the baseline value may be a predetermined nominal value, such as 0, corresponding to the dashed horizontal line 488.

Figure 4D:
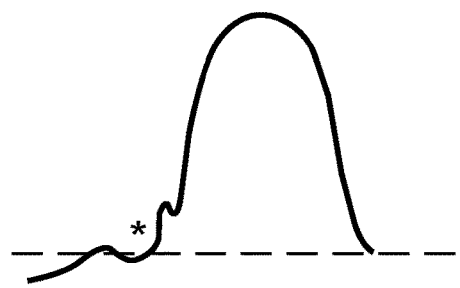
FIG. 4D are a sequence of waveforms representing right ventricular pressures, each waveform resulting from a delivery of a diaphragmatic stimulation having a different timing parameter.
Figure 4D:
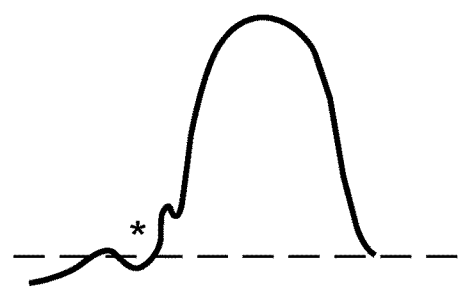
Figure 4D:
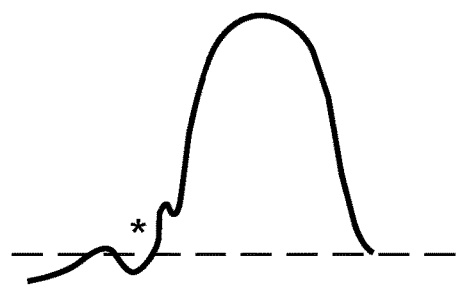
Figure 4D:
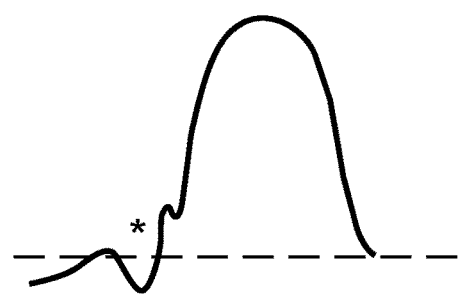
Figure 4D:
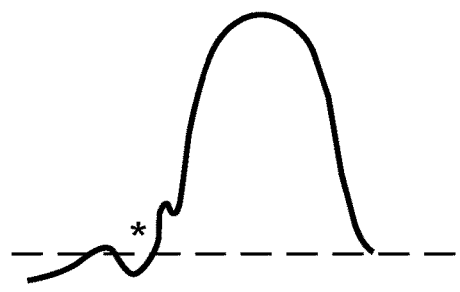
Figure 4D:
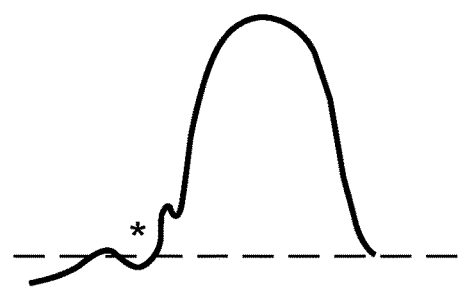

FIG. 4D includes illustrations of various waveforms representing measures of interest corresponding to RV pressures obtained by cycling through a stimulation therapy using a number of different delay periods, in accordance with blocks 502, 504, and 508 of FIG. 5A. The waveforms are illustrated relative to a nominal baseline value represented by the horizontal dashed line. The IMD 300 evaluates the various measures of RV pressure relative to the baseline value. From the various measures in FIG. 4D, the IMD 300 would identify the waveform of delay period 4 as having the most acceptable measure of interest because it deviates the most from the baseline value. Based on this identification, the IMD 300 selects as the optimal stimulation therapy, the electrical stimulation therapy having delay period 4.

Deviation from the baseline value may be further qualified by a direction of deviation. For example, referring to FIG. 4C, regarding RV pressure 466, the pressure measurement that deviates most from baseline value in the negative direction may be the most acceptable measure of interest. Physiologically, this most acceptable measure of interest represents the biggest increase in negative pressure within the intrathoracic cavity at end diastole, which is beneficial because this increases the net volume of blood within the cardiac chambers prior to systolic contraction. Conversely, regarding LV dP/dt 478, the measure that deviates most from baseline value in the positive direction may be the most acceptable measure of interest. Physiologically, this reflects the overall net force applied by the left ventricular wall towards the ejecting blood pool during systole, representative of the strength of the heart.

If the stimulation parameter being changed was a pulse amplitude or a pulse width, the most acceptable measure of interest may correspond to the measure of interest that falls within a range of acceptable measures of interest. Diaphragm stimulation delivered at too high of an energy level may result in symptomatic stimulation that is uncomfortable for the patient. For example, a patient may experience hiccups or pain if subjected to such stimulation. To protect against symptomatic stimulation, the IMD 300 may be programmed with a range of acceptable measures of interest, which range may be determined for a patient through clinical testing.

Figure 4E:
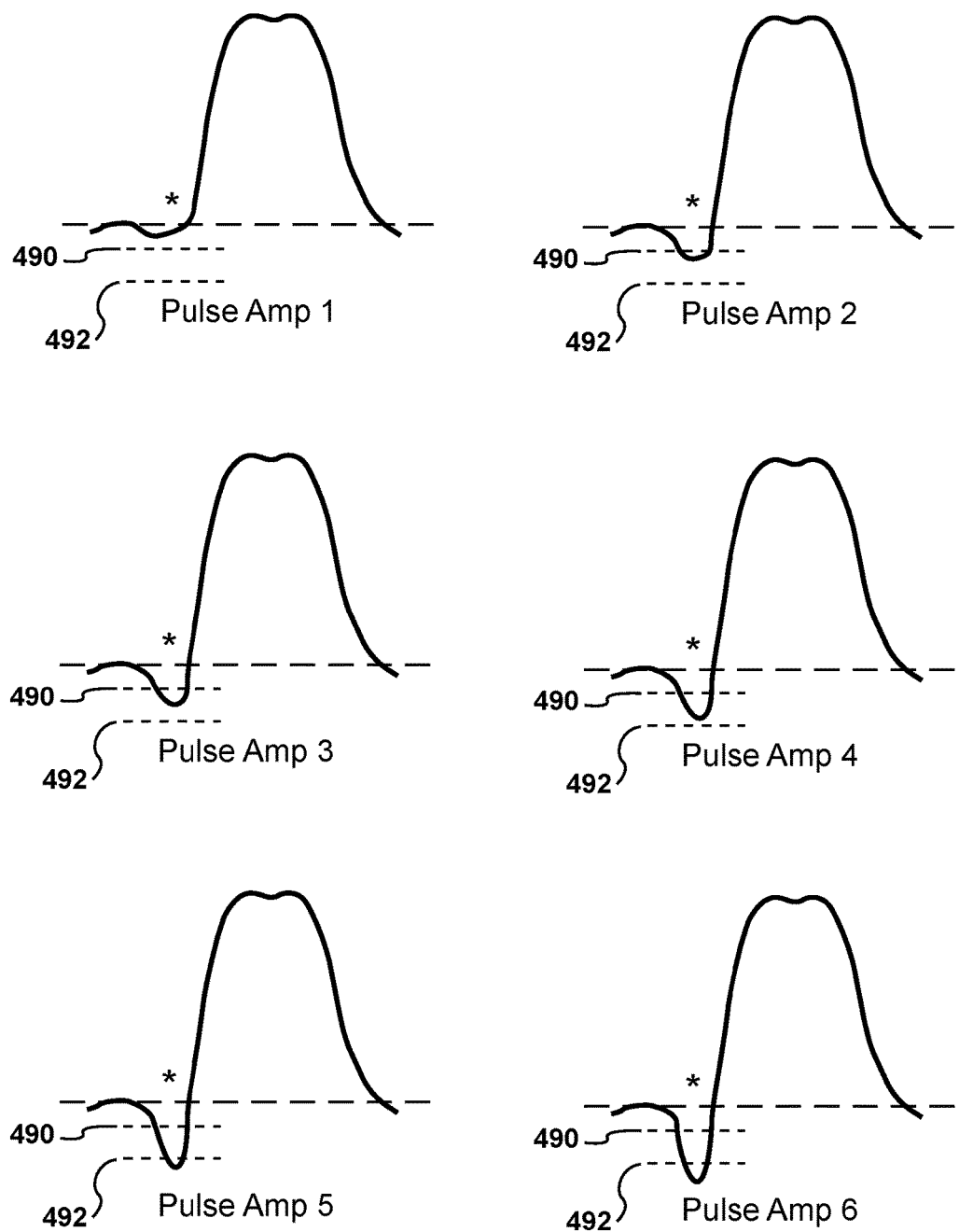
FIG. 4E are a sequence of waveforms representing left ventricular pressures, each waveform resulting from a delivery of a different diaphragmatic stimulation having a different pulse parameter.

FIG. 4E includes illustrations of various waveforms representing measures of interest corresponding to LV pressures obtained by cycling through a stimulation therapy using a number of different pulse amplitudes, in accordance with blocks 502, 504, and 508 of FIG. 5A. The waveforms are illustrated relative to a nominal baseline value represented by the horizontal dashed line, and relative to an acceptable range of measures of interest defined by a minimum pressure value 490 and a maximum pressure value 492.

The IMD 300 evaluates each of the derived measures of interest to determine if it falls within the acceptable range. Given the various measures in FIG. 4E, the IMD would identify each of the waveforms of pulse amplitude 2, pulse amplitude 3, and pulse amplitude 4 as having an acceptable measure of interest. Further evaluating these three waveforms, the IMD 300 may then determine the measure of interest having the lowest energy output, e.g., the lowest pulse amplitude, out of these three to be the most acceptable measure of interest. Based on this identification, the IMD would select as the optimal stimulation therapy, the electrical stimulation therapy having pulse amplitude 2. The selection of the electrical stimulation therapy having the lowest energy output reduces energy consumption of the IMD and thus extends the longevity of the IMD.

Figure 5C:
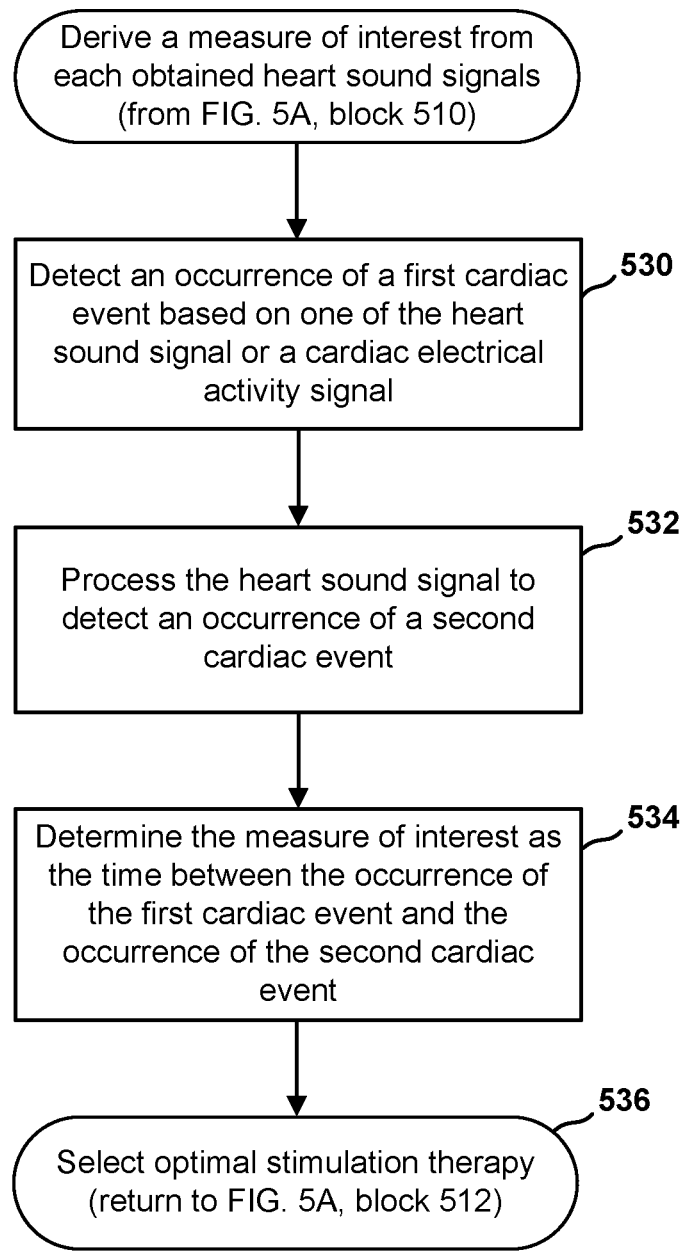
FIG. 5C is a flow chart of a method of deriving a time-based measure of interest from heart sound signals.

FIG. 5C is a detailed flow chart of a method of deriving a measure of interest from each obtained signal, as generally set forth in FIG. 5A, block 510, when the obtained signals are heart sound signals. The measure of interest may be derived by the IMD 300. Modules of the IMD 300 involved in deriving a measure of interest may include the pressure signal module 330, the cardiac signal module 328, and the therapy module 340. Alternatively, the measure of interest may be derived by an external device. In the case of the latter, the IMD 300 is configured to store the signals it obtains and to transmit the signals to the external device.

At block 530, the IMD 300 detects an occurrence of a first cardiac event based on one of a heart sound signal or a cardiac electrical activity signal. To this end, the heart motion/sounds analysis module 334 of the IMD 300 may receive a signal from the motion sensor 316 corresponding to heart sounds. The heart motion/sounds analysis module 334 may be configured to process the signal to identify the first cardiac event. For example, the heart motion/sounds analysis module 334 may filter the signal in a first frequency range, such as 50-80 Hz, locate the peak power in the filtered signal, and identify the occurrence of the peak power as an occurrence of a first cardiac event corresponding to a Q wave.

In another configuration, the EGM analysis module 332 of the IMD 300 may receive a cardiac electrical activity signal from the cardiac event source 306 that is sensed by the electrodes 312, 314. The EGM analysis module 332 may be configured to process the electrical activity signal to identify the first cardiac event. For example, the EGM analysis module 332 may process the signal, locate a peak amplitude in the signal, and identify the occurrence of the peak amplitude as an occurrence of a first cardiac event corresponding to a R wave.

At block 532, the IMD 300 process the heart sound signal to detect an occurrence of a second cardiac event. To this end, the heart motion/sounds analysis module 334 of the IMD 300 may receive a signal from the motion sensor 316 corresponding to heart sounds. The heart motion/sounds analysis module 334 may be configured to process the signal to identify the second cardiac event. For example, the heart motion/sounds analysis module 334 may filter the signal in a second frequency range, such as 110-135 Hz, locate the peak power in the filtered signal, and identify the occurrence of the peak power as an occurrence of a second cardiac event corresponding to a mechanical cardiac event, such as mitral valve closure.

At block 534, the IMD 300 determines the measure of interest as the time between the occurrence of the first cardiac event and the occurrence of the second cardiac event. Modules of the IMD involved in determining the measure of interest may include the cardiac signal module 328 and the therapy module 340. The cardiac signal module 328 provides cardiac-event information to the therapy module 340. This cardiac-event information includes the time of occurrence of the first cardiac event, as detected by either one of the EGM analysis module 332 or the heart motion/sounds analysis module 334, and the time of occurrence of the second cardiac event, as detected by the heart motion/sounds analysis module 334. Based on the respective times of occurrence of the first cardiac event and the second cardiac event, the therapy module 340 determines the measure of interest. In instances where the first cardiac event is a Q wave or an R wave, and the second cardiac event is mitral valve closure, the measure of interest corresponds to an electromechanical activation time (EMAT).

In one configuration, the measure of interest corresponds to a time measurement determined from first and second cardiac events included in a single cardiac cycle. In another configuration, the measure of interest corresponds to a statistical time measurement, e.g., an average measurement, determined from a plurality of individual time measurements obtained over a period of time. In this case, respective time measurements are determined from respective pairs of first and second cardiac events for each of a respective cardiac cycle. In one configuration, the number of individual time measures obtained and used to determine the overall measure of interest is enough to encompass at least one respiration cycle. In this manner, the effects of respiration on the times of occurrence of the first cardiac event and the second cardiac event are accounted for.

At block 536 the process returns to block 512 of FIG. 5A. At block 512, the IMD 300 selects as the optimal stimulation therapy, the electrical stimulation therapy that results in a most acceptable measure of interest. What constitutes a most acceptable measure of interest may depend on the time measure from which the measure of interest is derived. For example, in the case of EMAT, i.e., the time between onset of a Q wave and the closure of the mitral valve, the most acceptable measure of interest corresponds to the shortest EMAT. In the example of left ventricular pressure, the time between onset of a Q wave and time to maximum forces, the most acceptable measure of interest corresponds to the shortest time from the QRS to dP/dt max.

Thus described, referring to FIGS. 5A, 5B, and 5C, is an algorithm for optimizing stimulation therapy for a patient through the delivery of stimulation therapy using different stimulation parameter values or settings, the obtaining of physiological measures resulting from these different stimulations, and the processing of the obtained measures to identify an optimal stimulation therapy. As mentioned previously, the algorithm may be executed entirely by the IMD 300, or by the IMD 300 in conjunction with an external device.

Real-Time or Near Real-Time Therapy Adjustment

Figure 6A:
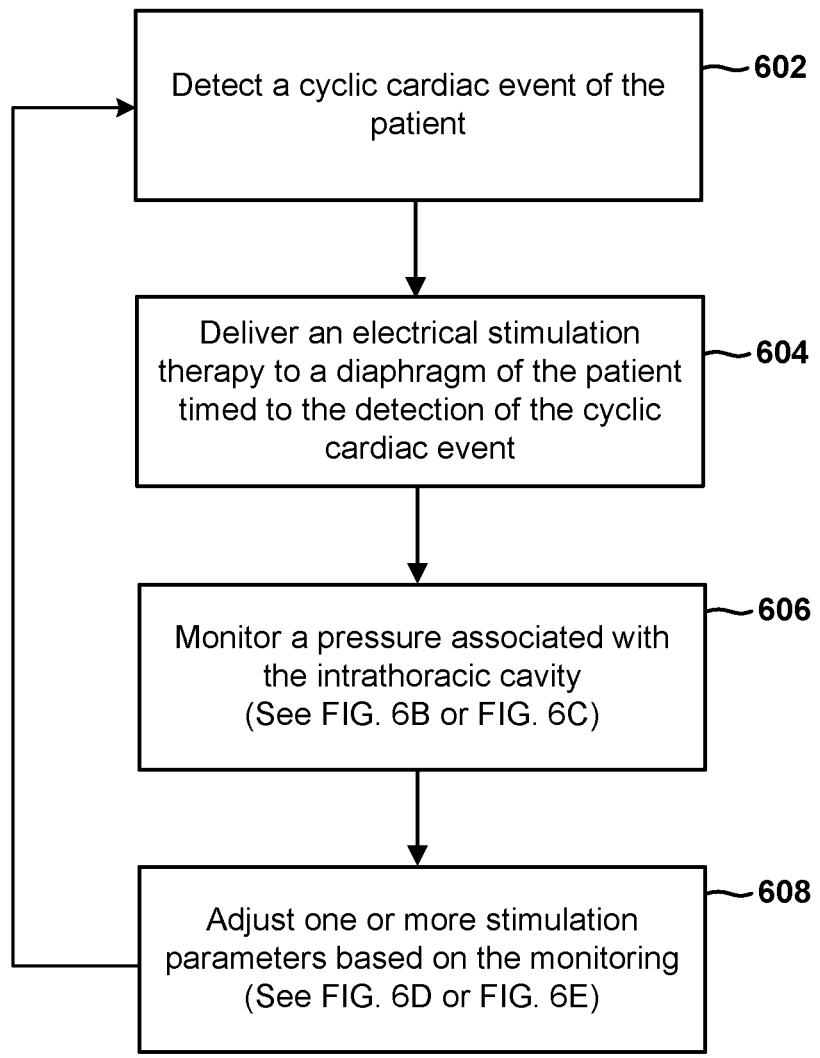
FIG. 6A is a flow chart of a method of affecting a pressure within the intrathoracic cavity through diaphragmatic stimulation.

FIG. 6A is a flow chart of a method of adjusting a diaphragmatic stimulation therapy, in real time or near real time, to affect a pressure within the intrathoracic cavity. The method may be performed by the IMD 300 of FIG. 3. In summary, an IMD delivers a stimulation therapy to a diaphragm timed to an occurrence of a cyclic cardiac event, and monitors a pressure associated the intrathoracic cavity resulting from the stimulation therapy. The stimulation therapy is defined by one or more stimulation parameters. The IMD may adjust one or more of the stimulation parameters for subsequent deliveries of the stimulation therapy based on the monitored pressure, to improve therapy outcome. For example, the timing of stimulation delivery, or the amplitude, pulse width, polarity, or waveform of stimulation pulses, may be adjusted to increase the acceleration of negative thoracic cavity pressure (suction) during left ventricular filling to thereby increase filling volume. The IMD may also withhold the delivery of stimulation therapy or adjust one or more of the stimulation parameters for instances of stimulation therapy timed to occur at or near an occurrence of a pressure event. For example, stimulation therapy may be withheld at or near end inspiration of a respiration cycle to reduce the likelihood of local diaphragmatic muscle fatigue due to either hyper contraction or extended contractile durations as a result of sequential excitatory stimuli.

At block 602, the IMD 300 detects a cyclic cardiac event of the patient. Cyclic cardiac events are events which—under normal cardiac functioning conditions—occur in every cardiac cycle. Such events may be, for example, an electrical cardiac event, e.g., a ventricular depolarization, or a mechanical cardiac event, e.g., ventricular contraction. Modules of the IMD 300 involved in the detection of a cyclic cardiac event may include the cardiac event source 306 and the cardiac signal module 328. As described above referring to FIG. 3, the cardiac event source 306 may include a pair of electrodes 312, 314 that sense electrical activity of the heart, and a motion sensor 316 that sensed movement of the heart. The cardiac signal module 328 includes an EGM analysis module 332 configured to receive signals sensed by the electrodes 312, 314 and to detect cyclic electrical cardiac events, including for example, ventricular depolarizations represented by Q waves, R waves, or QRS complexes. The cardiac signal module 328 also includes a heart motion/sounds analysis module 334 configured to receive signals from the motion sensor 316, e.g., an accelerometer or an acoustic transducer, and to identify cyclic mechanical cardiac events, including for example ventricular contractions represented by S1 heart sounds.

At block 604, the IMD 300 delivers an electrical stimulation therapy to a diaphragm of the patient. Modules of the IMD 300 involved in the delivery of electrical stimulation may include the therapy module 340 and the stimulation delivery mechanism 310. As described above referring to FIG. 3, the therapy module 340 generates the electrical stimulation therapy in accordance with one or more pulse parameters, and provides the therapy to the stimulation delivery mechanism 310 in accordance with a timing parameter. The stimulation delivery mechanism 310, in turn, applies the stimulation therapy to the diaphragm.

Continuing with block 604, the electrical stimulation therapy generated and delivered by the IMD 300 is defined by stimulation parameters that include: 1) one or more pulse parameters having a value or setting selected to define a stimulation pulse that induces a partial contraction of the diaphragm, and 2) a timing parameter that controls the timing of the delivery of one or more stimulation pulses. The pulse parameters may include, for example, a pulse waveform type, a pulse amplitude, a pulse duration, and a pulse polarity. The timing parameter may include one or more of a delay period that defines a time between a detected cardiac event and a delivery of an electrical stimulation pulse, and a stimulation rate that defines a time interval between a series of stimulation pulses.

With respect to the pulse parameters, as previously described, a partial contraction of the diaphragm typically entails a very short (only a few tens of milliseconds) pulse-like, biphasic (singular-caudal followed by singular-cranial) asymptomatic motion of the diaphragm. The IMD 300, including in particular the therapy module 340, is configured to generate stimulation pulses that result in very short, biphasic asymptomatic motion of the diaphragm. To this end, the therapy module 340 may be configured to select a setting of square, sinusoidal, triangular, or sawtooth for the pulse waveform type, and to select a setting of positive or negative for the pulse polarity. The therapy module 340 may be further configured to select a value for the pulse amplitude that is between 0.0 volts and 7.5 volts, and to select a value for the pulse duration that is between 0.0 milliseconds and 5 milliseconds.

Regarding the timing parameter, the therapy module 340 may be configured to determine either of a delay period or a stimulation rate. As previously described, the delay period may be based on the time between successive detected cardiac events. For example, the EGM analysis module 332 of the cardiac signal module 328 may be configured to detect ventricular events, e.g., R waves, and to output such detections to the therapy module 340. The cardiac-event analysis module 342 may process the detected ventricular events to determine a statistical measure of time between a number of pairs of successive ventricular events. The cardiac-event analysis module 342 may then determine a delay period based on the statistical measure and an offset relative to the statistical measure, and control the pulse generator 346 to output stimulation pulses based on the determined delay period. The delay period is selected to time the delivery of the stimulation pulses to occur either just prior to, or just after, a detection of a particular cardiac event. Details related to the determining of the delay period are provided in U.S. Patent Application Publication No, 2017/0021166, titled Systems, Devices, and Methods for Improving Hemodynamic Performance Through Asymptomatic Diaphragm Stimulation, the disclosure of which is hereby incorporated by reference.

The stimulation rate may also be based on the time between successive detected cardiac events. The EGM analysis module 332 of the cardiac signal module 328 may be configured to detect ventricular events, e.g., R waves, and to output such detections to the therapy module 340. The cardiac-event analysis module 342 may process the detected ventricular events to determine a statistical measure of time between a number of pairs of successive ventricular events. The cardiac-event analysis module 342 may then determine a stimulation rate based on the statistical measure. For example, the statistical measure may be the average time between successive detected cardiac events.

Initial selection of pulse parameter settings and values and the timing parameter by the therapy module 340 may be performed by a physician through an external device, e.g., a programmer. In this case, the external device provides selection commands to the therapy module 340 through a wireless communication link, and the therapy module selects the pulse parameters and timing parameter in accordance with the commands. Alternatively, selection of pulse parameter settings and values and the timing parameter by the therapy module 340 may be automated, as described above referring to FIG. 5A.

At block 606, the IMD 300 monitors a pressure associated with the intrathoracic cavity to determine whether stimulation parameters should be changed in an attempt to improve patient outcome. The pressure associated with the intrathoracic cavity may be one or more of an intrathoracic pressure or a cardiovascular pressure. The cardiovascular pressure may be, for example, one of a right atrial pressure, a right ventricular pressure, a left ventricular pressure, and an aortic pressure. A pressure associated with the intrathoracic cavity may be monitored based on one or more pressure measurements (see FIG. 6B, described below for details), or occurrences of one or more pressure events (see FIG. 6C, also described below for details).

At block 608, the IMD 300 adjusts one or more stimulation parameters based on the outcome of the monitoring. If the monitoring outcome indicates that stimulation parameters should be changed, the therapy module 340 may select a parameter to be adjusted and may make the adjustment. Methods of parameter selection and adjustment are described below referring to FIG. 6D and FIG. 6E.

Continuing with FIG. 6A, after one or more of the stimulation parameters are adjusted, the process returns to block 602 where a next cyclic cardiac event is detected. The method of FIG. 6A may be repeated until no further adjustments in stimulation parameters are warranted, in which case the stimulation therapy settings, including both the timing parameters and the pulse parameters of the IMD 300 may be considered to be optimized for the patient. The process of FIG. 6A, may be executed during implant of an IMD to obtain initial stimulation parameter settings for the patient. Thereafter, the process may be continuously or periodically repeated automatically by the IMD 300 in order to make changes to stimulation parameters values and settings that may improve patient therapy. The method of FIG. 6A may also be continuously repeated to monitor for pressure events related to respiration for purposes of temporarily adjusting stimulation therapy at designated respiration events.

Figure 6B:
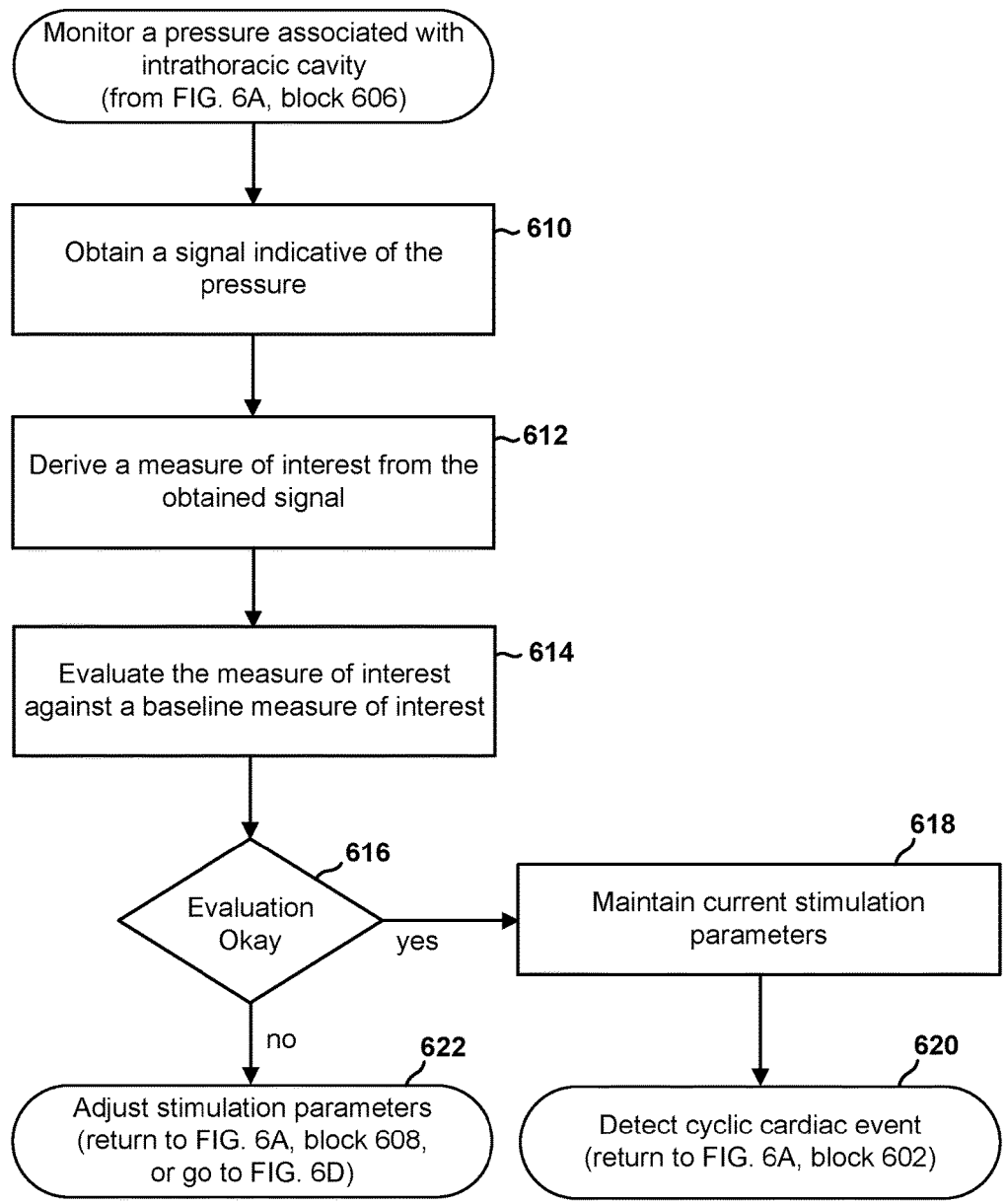
FIG. 6B is a flow chart of a method of monitoring pressure within the intrathoracic cavity based on pressure measurements.

FIG. 6B is a detailed flow chart of a method of monitoring pressure associated with the intrathoracic cavity as generally set forth in FIG. 6A, block 606. The method of monitoring disclosed in FIG. 6B is based on one or more pressure measurements. At block 610, the IMD 300 obtains a signal indicative of a pressure associated with the intrathoracic cavity. The pressure associated with the intrathoracic cavity may be intrathoracic pressure, right atrial pressure, right ventricular pressure, left ventricular pressure, aortic pressure, and pulmonary artery pressure. Modules of the IMD 300 involved in obtaining a signal indicative of a pressure of the intrathoracic cavity may include the pressure measurement source 308 and the pressure measurement module 336. As described above referring to FIG. 3, the pressure measurement source 308 may be configured to sense either of a pressure through a pressure sensor 318, diaphragm motion through a motion sensor 320, or heart sounds through a motion sensor 320, and provide a corresponding signal to the pressure measurement module 336.

At block 612, the IMD 300 derives a measure of interest from the obtained signal. Modules of the IMD 300 that may be configured to derive a measure of interest include the pressure measurement module 336. The measure of interest may be an individual pressure measurement at or near a fiducial point associated with a cardiac cycle. For example, the measure of interest may be a pressure measurement at or near one of: 1) the beginning of diastole, 2) the end of diastole, or 3) the beginning of systole. To derive these measures, the pressure measurement module 336 may receive cardiac cycle information from the cardiac signal module 328, process the cardiac cycle information to identify the one or more fiducial points, and process the pressure signal received from the pressure measurement source 308 to derive a pressure measurement at or near the time of each of the one or more fiducial points. The measure of interest may also be a statistical measure that is based on a number of individual pressure measurements at or near a fiducial point associated with a cardiac cycle. The statistical measure may be an average pressure measurement, including for example, a running average measurement obtained over a number of cardiac cycles.

In another example, the measure of interest may be a pressure measurement at or near the time of a delivery of the electrical stimulation therapy. To derive this measure, the pressure measurement module 336 may receive stimulation therapy information from the therapy module 340 and process the pressure signal received from the pressure measurement source 308 to derive a pressure measurement at or near the time of a delivery of the electrical stimulation therapy. In this case also, the measure of interest may be a statistical measure that is based on a number of individual pressure measurements at or near the time of a delivery of the electrical stimulation therapy. The statistical measure may be an average pressure measurement, including for example, a running average measurement obtained over a number of stimulation cycles.

At block 614 the IMD 300 evaluates the measure of interest against a baseline measure of interest, or baseline value. Modules of the IMD 300 that may be configured to evaluate the measure of interest include the therapy module 340. As described above referring to FIGS. 5A, 5B, and 5C, the baseline measure of interest may be based on previously obtained pressure measurements or may correspond to a predetermined nominal value. Regarding baseline measures of interest that are based on previously obtained pressure measurements, such baseline measures of interest may be an individual pressure measurement at or near a fiducial point associated with a previous cardiac cycle or a statistical measure, e.g., running average, of a number of individual pressure measurements obtained at the fiducial point over a corresponding number of previous cardiac cycles. The fiducial point of the cardiac cycle at which pressure measurements are obtained for purposes of deriving the baseline measure of interest is the same as the fiducial point of the cardiac cycle at which pressure measurements are obtained for deriving the measure of interest. For example, the fiducial point may be a R wave, in which case the baseline measure of interest is based on pressure measurements at or near the R wave of each of one or more cardiac cycles and the measure of interest is also based on pressure measurements at or near the R wave of each of one or more cardiac cycles.

Evaluating the measure of interest against the baseline measure of interest may involve comparing the respective measures of interest to determine if the present measure of interest represents a change in pressure that is hemodynamically beneficial. It has been observed, for example, that obtaining a greatest negative intrathoracic pressure at some fiducial points within a cardiac cycle, without exceeding a maximum threshold negative pressure, improves hemodynamic function. Specifically, achieving a maximum allowable negative intrathoracic pressure at the beginning of systole (the particular fiducial point) increases negative pressure during diastole thereby improving cardiac filling. Likewise, achieving greater filling at the beginning of diastole (the particular fiducial point) may be desirable because it increases the net amount of blood which can be ejected from the heart, and/or causes the heart to operate at a more efficient point of muscular contraction. Also, achieving greater filling at the end of diastole (the particular fiducial point) may be desirable because it increases the amount of passive tension applied by the left ventricle on the contained pool which augments the forces applied by the left ventricle during systole.

Accordingly, continuing with block 614, in one configuration the therapy module 340, including the pressure analysis module 344, may be configured to compare a present measure of interest against a baseline measure of interest to determine if the present measure of interest is: 1) more negative than the baseline, or in other words, represents an increase in negative pressure, or 2) less negative than the baseline, or in other words, represents a decrease in negative pressure.

At block 616, the therapy module 340 determines if the evaluation outcome of block 614 is acceptable or unacceptable. To this end, if the present measure of interest is more negative than the baseline measure of interest the therapy module 340 may determine that the evaluation outcome is acceptable. In this instance, the process proceeds to block 618, wherein the therapy module 340 determines to maintain the current stimulation parameters. At block 620, the process returns to block 602 of FIG. 6A, where a next cyclic cardiac event is detected, and then block 604 wherein stimulation therapy is delivered in accordance with the current stimulation parameters, timed relative to the next detected cyclic cardiac event. Returning to block 616, if present measure of interest is less negative than the baseline measure of interest the therapy module 340 may determine that the evaluation outcome is unacceptable. In this instance, the process proceeds to block 622, where one or more stimulation parameters are adjusted in accordance with block 608 of FIG. 6A, or FIG. 6D as described immediately below.

Figure 6C:
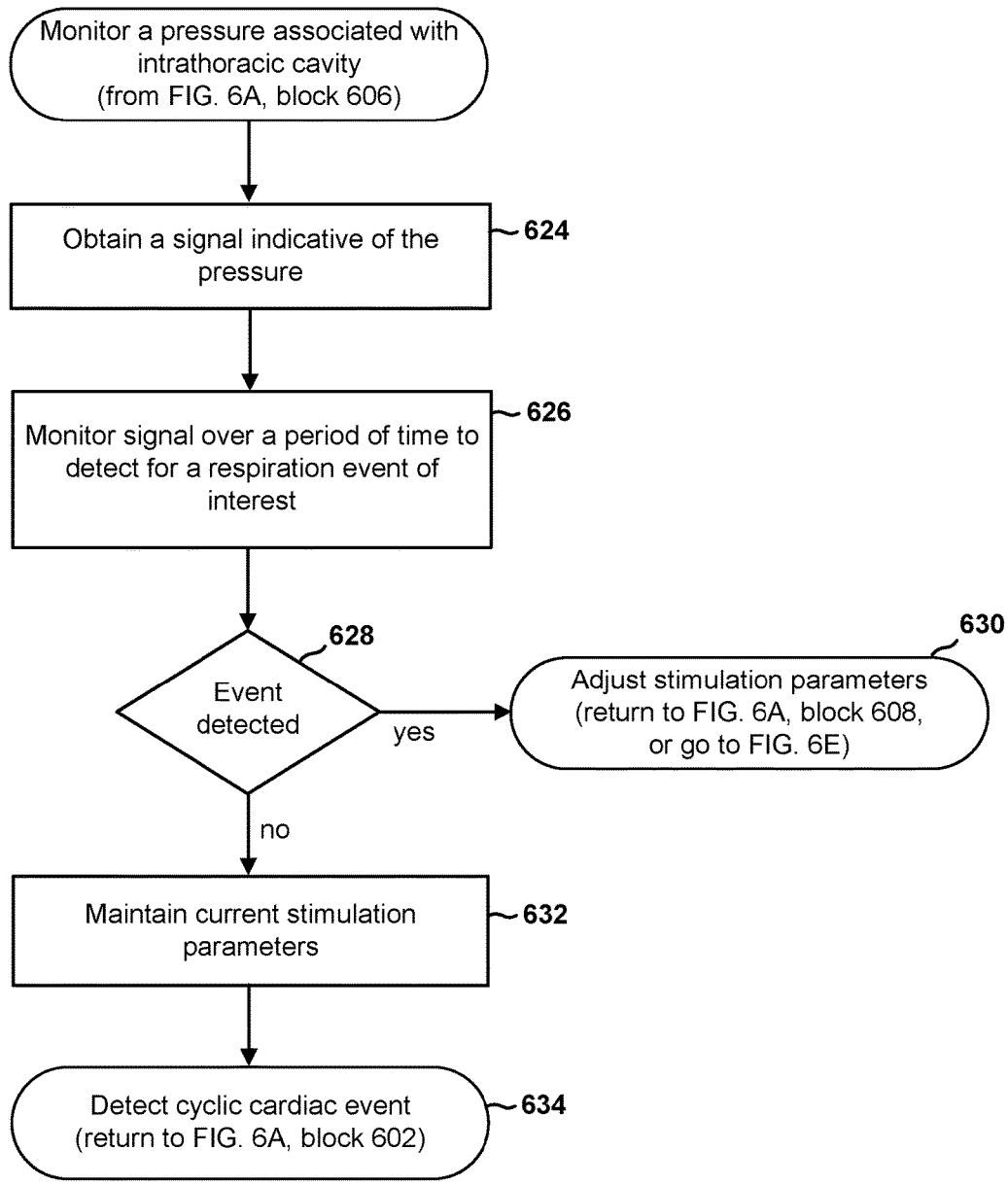
FIG. 6C is a flow chart of a method of monitoring pressure within the intrathoracic cavity based on a detection of a pressure event related to respiration.
Figure 6D:
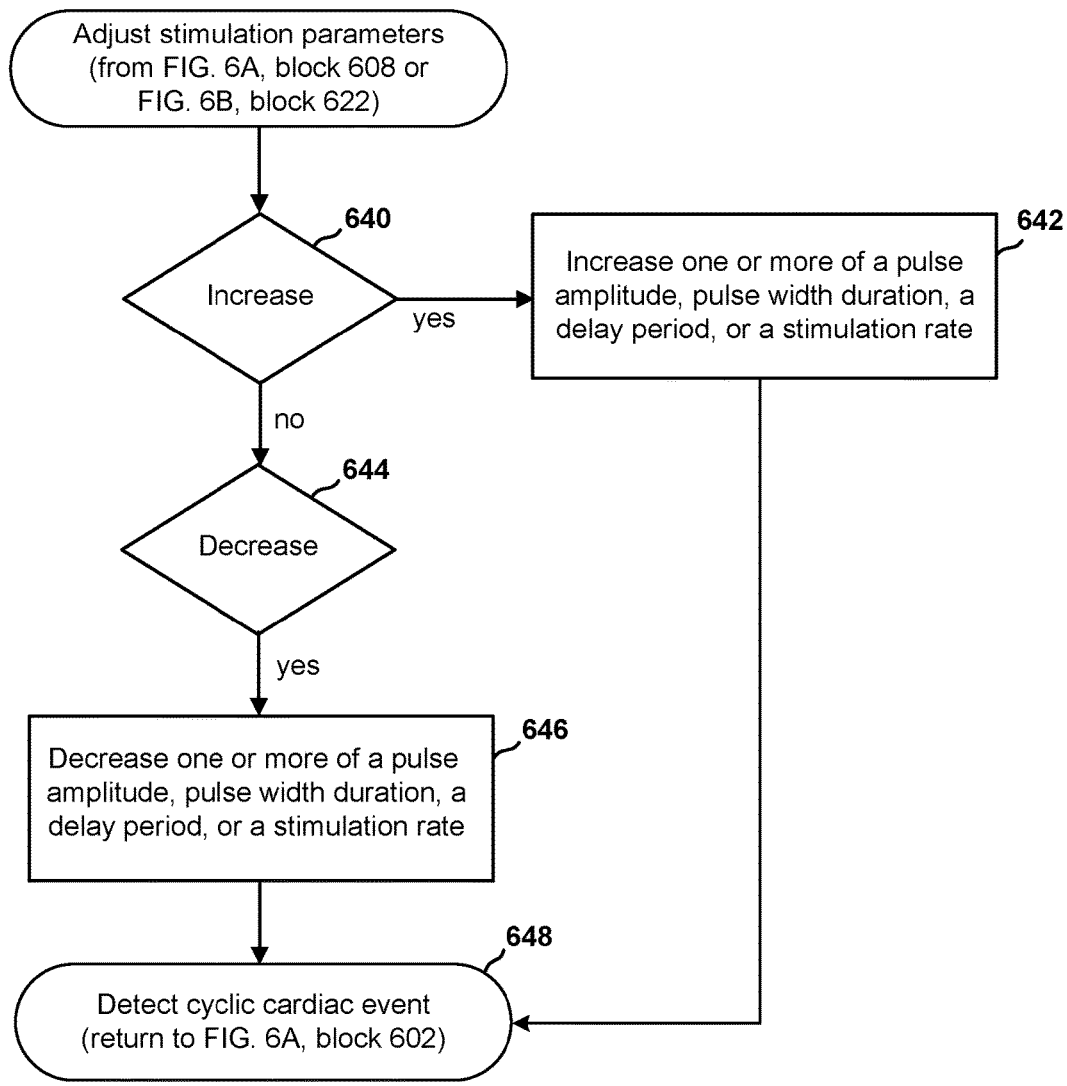
FIG. 6D is a flow chart of a method of adjusting stimulation parameters based on monitoring results obtained using the method of FIG. 6B.

FIG. 6D is a flow chart of a method of adjusting stimulation parameters when the pressure evaluation outcome from the method of FIG. 6B is not acceptable. Modules of the IMD 300 that may be configured to evaluate the measure of interest include the therapy module 340. Different stimulation parameters may be adjusted in one or more ways, e.g., by increasing or decreasing parameter values, to eventually obtain a pressure evaluation outcome that is acceptable. To this end, the therapy module 340 may be configured to attempt either of a parameter increase or a parameter decrease to improve the pressure evaluation outcome. The choice of which to attempt first, parameter increase or parameter decrease, may be programmed into the therapy module, or may be randomly selected by the therapy module.

For example, at block 640, the therapy module 340 may first decide to increase a stimulation parameter, in which case the process proceeds to block 642 where one or more of the stimulation parameters may be changed as summarized in Table 2:

TABLE 2

| Stimulation Parameter | Range | Adjustment |
|---|---|---|
| Delay period | −150 to +150 milliseconds relative to detected cardiac event, or next anticipated cardiac event | increase by 10 milliseconds |
| Pulse amplitude | 0-7.5 volts | increase by 0.1-0.5 volts |
| Pulse width | 0-5 milliseconds | increase by 0.1-1.5 milliseconds |
| Pulse waveform | triangle sawtooth: reverse sawtooth sinusoidal | change from one waveform to another |
| Polarity | electrode 1 → electrode 2 electrode 2 → electrode 1 electrode 1 → can can → electrode 1 electrode 2 → can can → electrode 2 | change from one polarity to another |

Continuing with FIG. 6D, at block 644, the therapy module 340 may instead decide to decrease a stimulation parameter, in which case the process proceeds to block 646 where one or more of the stimulation parameters may be changed as summarized in Table 3:

TABLE 3

| Stimulation Parameter | Range | Adjustment |
|---|---|---|
| Delay period | −150 to +150 milliseconds relative to detected cardiac event, or next anticipated cardiac event | decrease by 10 milliseconds |
| Pulse amplitude | 0-7.5 volts | decrease by 0.1-0.5 volts |
| Pulse width | 0-5 milliseconds | decrease by 0.1-1.5 milliseconds |
| Pulse waveform | triangle sawtooth: reverse sawtooth sinusoidal | change from one waveform to another |
| Polarity | electrode 1 → electrode 2 electrode 2 → electrode 1 electrode 1 → can can → electrode 1 electrode 2 → Can can → electrode 2 | change from one polarity to another |

Continuing with FIG. 6D, once the stimulation parameters are adjusted at either of block 642 or block 646, at block 648 the process returns to FIG. 6A, block 604, where stimulation therapy is delivered time to the occurrence of the next cyclic cardiac event.

FIG. 6C is a detailed flow chart of another method of monitoring pressure associated with the intrathoracic cavity as generally set forth in FIG. 6A, block 606. The method of monitoring disclosed in FIG. 6C is based on one or more cyclic pressure events, such as end inspiration or end expiration of respiration. At block 624, the IMD 300 obtains a signal indicative of a pressure associated with the intrathoracic cavity. Modules of the IMD 300 involved in obtaining a signal indicative of a pressure of the intrathoracic cavity may include the pressure measurement source 308 and the diaphragm motion and heart sounds analysis module 338. As described above referring to FIG. 3, the pressure measurement source 308 may be configured to sense either of a pressure through a pressure sensor 318, diaphragm motion through a motion sensor 320, or heart sounds through a motion sensor 320, and provide a corresponding signal to the diaphragm motion and heart sounds analysis module 338.

At block 626, the IMD 300 monitors the obtained signal over a period of time to detect for one or more events of interest within the respiration cycles. Modules of the IMD 300 involved in monitoring the obtained signal may include the diaphragm motion and heart sounds analysis module 338. In one configuration, the diaphragm motion and heart sounds analysis module 338 may be configured to analyze a signal obtained from a motion sensor 320 placed on the diaphragm to identify fiducial points corresponding to one or more maximum intrathoracic pressures and one or more minimum intrathoracic pressures resulting from diaphragm contractions and expansions.

For example, referring to FIG. 4A, the diaphragm motion and heart sounds analysis module 338 may process an electrical signal 408 to detect respiration cycles 416 including a minimum pressure point 412 generally corresponding to end expiration, and a maximum pressure point 410 generally corresponding to end inspiration. Based these identified pressure points 410, 412, the diaphragm motion and heart sounds analysis module 338 identifies respiration cycles, and detects events of interest within the respiration cycles. These events of interest may be regions of a respiration cycle corresponding to transitions between inspiration stages and expiration stages. The events of interest may be may also be points of end inspiration and end expiration within a respiration cycle.

Alternatively, referring to FIG. 4B, the diaphragm motion and heart sounds analysis module 338 may process a heart sounds signal 420 received from a motion sensor 320 in the form of an acoustic transducer, or motion signals 430, 432, 434 received from a motion sensor in the form of a three-dimensional accelerometer, to detect events of interest within the respiration cycles. For example, the diaphragm motion and heart sounds analysis module 338 may detect end inspiration 436, 438.

At block 628, the therapy module 340 determines whether an event of interest is presently detected. If an event of interest is not presently detected, the process proceeds to block 632, wherein the therapy module determines to maintain the current stimulation parameters. At block 634, the process returns to block 602 of FIG. 6A, where a next cyclic cardiac event is detected, and then block 604 where stimulation therapy is delivered in accordance with the current stimulation parameters, timed relative to the next detected cyclic cardiac event.

Returning to block 628, if an event of interest is presently detected, the process proceeds to block 630, where one or more stimulation parameters are adjusted in accordance with block 608 of FIG. 6A, or FIG. 6E as described immediately below. Stimulation parameter adjustment is temporary so to be in effect only for stimulation therapy that is timed to be delivered at or near the time of occurrence of the event of interest, after which any changed stimulation parameter would return to its pre-adjustment setting.

Figure 6E:
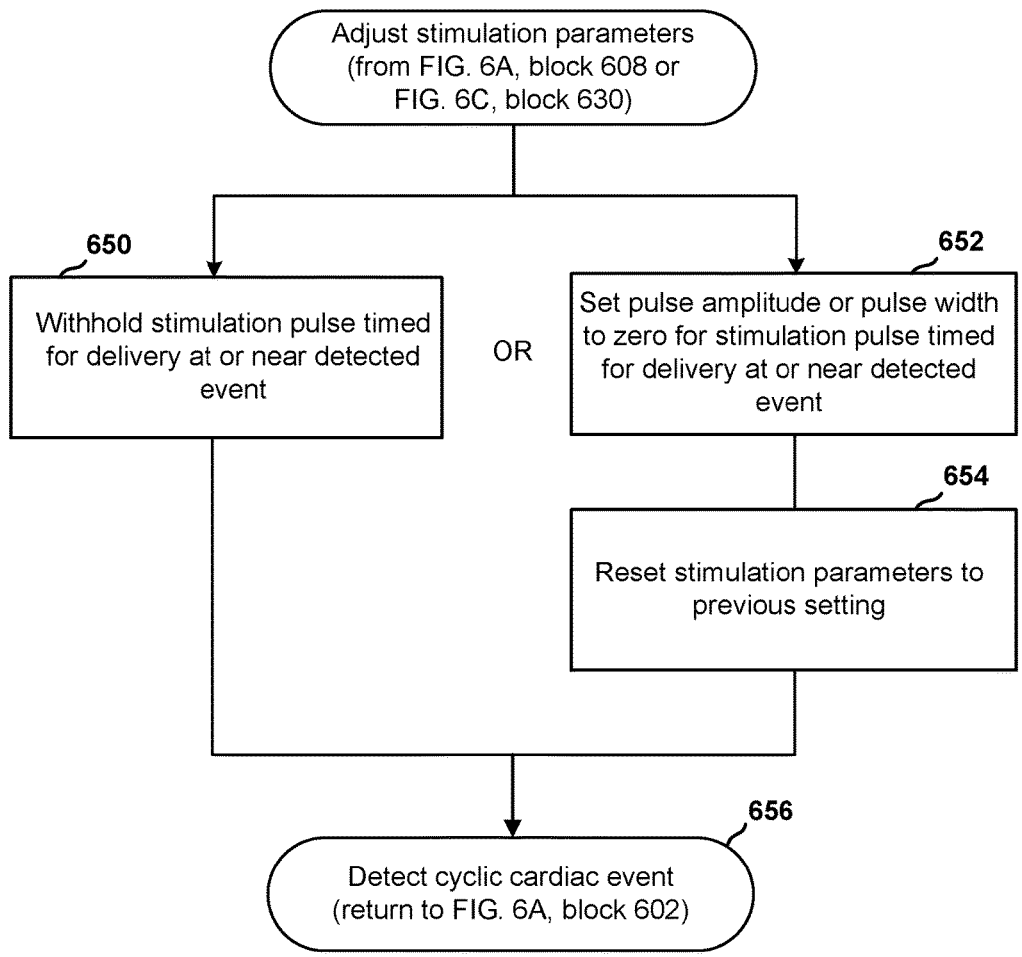
FIG. 6E is a flow chart of a method of adjusting stimulation parameters based on monitoring results obtained using the method of FIG. 6C.

FIG. 6E is a flow chart of a method of adjusting stimulation parameters when the detection outcome from the method of FIG. 6C indicates that a respiration event of interest has been detected. At block 650, the therapy module 340 may adjust stimulation parameters for the upcoming delivery of stimulation therapy by simply withholding, e.g., not outputting, the stimulation pulse that is timed for delivery at or near the detected event.

Alternatively, at block 652, the therapy module 340 may temporarily adjust stimulation parameters for the stimulation pulse timed for delivery at or near the detected event by setting one or more stimulation parameters to zero. For example, pulse amplitude may be set to 0 volts, or the pulse width may be set to 0 milliseconds.

At block 654, once a stimulation pulse is delivered in accordance with the temporary stimulation parameters set in block 652, the therapy module 340 resets the stimulation parameters to their prior setting. At block 656 the process returns to FIG. 6A, block 604, where stimulation therapy is delivered timed to the occurrence of the next cyclic cardiac event.

Referring to FIG. 4A, which illustrates—from top to bottom—waveforms representing a cardiac electrical activity signal 402, a cardiac pressure signal 414, and intrathoracic cavity pressure signal 408 during delivery of diaphragmatic stimulation, a benefit of the method of FIG. 6E is shown. The ON markers corresponds to instances of where stimulation was delivered to a diaphragm. The OFF marker corresponds to an instance where stimulation was withheld due to the presence of end inspiration. From the cardiac pressure signal 414 it is noted that ON instances result in partial, non-respiratory contraction of the diaphragm and nearly instantaneous changes to left ventricular hemodynamic waveform morphologies during filling (immediately preceding systolic increases, which increases are noted by sharp upward inflection in pressure waveform in the ON marker). The OFF instance result in a low variability in intrathoracic pressure including minimal acute negative inflections and subsequent positive reflections with a corresponding gradual change to left ventricular filling (immediately preceding systolic increases, which increases are noted by sharp upward inflection in pressure waveform in the OFF marker) and pressure due to passive pressure gradients and muted ventricular relaxation during filling Left ventricular pressure waveforms 414 during intrinsic function are marked by a steady gradual increase as left ventricular filling results from both passive left ventricular relaxation and left atrial contraction. During therapy however, diaphragmatic movement accelerates left ventricular filling and pressure increases resulting in a drop in left ventricular pressure immediately preceding systolic contraction as the left ventricle is "overfilled" and begins to equilibrate between the diastolic and systolic phases.

Figure 7:
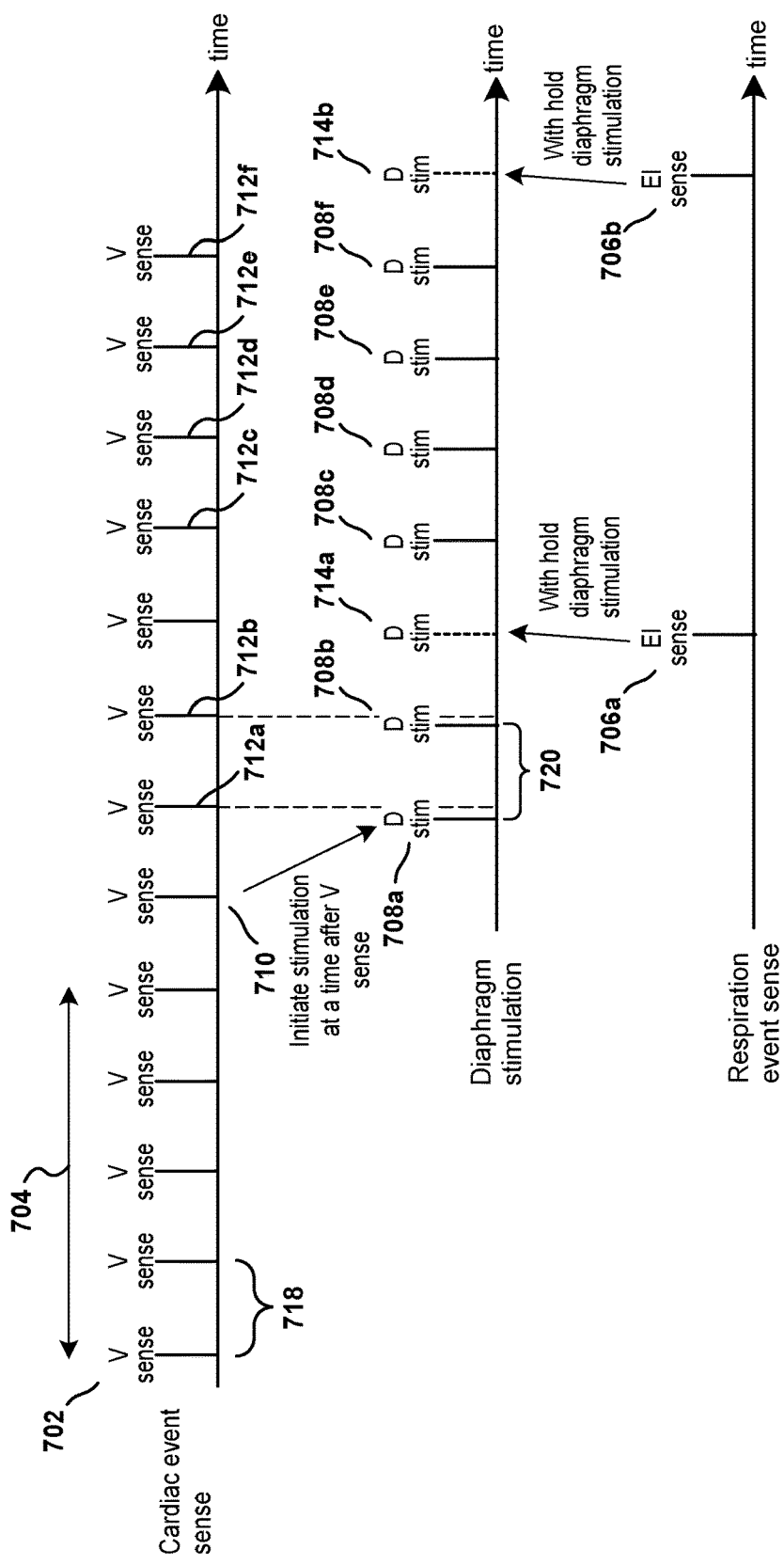
FIG. 7 is a timing diagram illustrating a series of detected cardiac events, a number of detected pressure events related to respiration detected in accordance with the method of FIG. 6C, and a series of diaphragmatic stimulations delivered in accordance with the method of FIG. 6E.

Further regarding respiration controlled diaphragm stimulation, FIG. 7 is a timing diagram illustrating a series of detected cardiac events 702, a number of pressure events 706 related to respiration detected in accordance with the method of FIG. 6C, and a series of diaphragm stimulations 708, 714, 716 delivered or withheld in accordance with the method of FIG. 6E. The diaphragm stimulations 708 of FIG. 7 are set to be delivered to the diaphragm at a stimulation rate determined based on detected cardiac events. To this end, and with additional reference to FIG. 3, the EGM analysis module 332 of the cardiac signal module 328 may receive electrical signals corresponding to the electrical activity of the heart from the electrodes 312, 314, and process these signals to detect electrical cardiac events 702, such as ventricular depolarizations. Alternatively, the heart motion/sounds analysis module 334 may receive signals from the motion sensor 316 and process these signals to detect mechanical cardiac events 702, such as ventricular contractions.

In either case, the cardiac signal module 328 outputs these cardiac event detections to the therapy module 340 as cardiac-event information. The therapy module 340 processes the cardiac-event information to obtain the diaphragmatic stimulation rate. For example, the cardiac-event analysis module 342 may process a number 704 of the detected cardiac events to obtain a current heart rate defined by a cardiac cycle length 718, and set the diaphragmatic stimulation rate equal to the current heart rate. The cardiac-event analysis module 342 may maintain a running average of the current heart rate by continuously processing cardiac-event information corresponding to detected cardiac events 702, and recalculating the heart rate based on a most recent number, e.g., five or ten, of detected cardiac events, and resetting the diaphragmatic stimulation rate accordingly.

Once the diaphragmatic stimulation rate is determined, the therapy module 340 may initiate delivery of a series of diaphragmatic stimulation pulses at the current rate. Initiation of the delivery of the series of stimulation pulses may be timed relative to a detected, cyclic cardiac event. For example, for the series of diaphragmatic stimulation pulses 708a-708f (D stim) shown in FIG. 7, the first pulse 708a is delivered at a time after detection of a cyclic ventricular cardiac event 710 (V sense). Thereafter, subsequent pulses 708b-708f are delivered at intervals 720 corresponding to the stimulation rate. The time at which the first pulse 708a is delivered is selected such that the first pulse is delivered at a time that at least partially precedes an upcoming cyclic cardiac event 712a. Subsequent pulses 708b-708f delivered at the stimulation rate are also delivered at a time that at least partially precedes an upcoming cardiac event 712b-712f. This timing relationship between stimulation pulse delivery and upcoming cyclic cardiac events would continue for as long as the current heart rate remains steady. Upon a change in heart rate, the diaphragmatic stimulation rate would be changed to the then current heart rate and stimulation delivery would be reinitiated.

As described above referring to FIG. 6C, the IMD 300 monitors respiration of the patient to detect for a respiration event of interest. To this end, the pressure measurement source 308 of the IMD 300 may sense either of mechanical activity of the heart or mechanical activity of the diaphragm through a motion sensor 320 that is associated with the diaphragm. Referring to FIG. 3, the diaphragm motion and heart sounds analysis module 338 may obtain an electrical signal from the motion sensor 320, process the electrical signal to detect at least one of a heart sound signal of the heart, and an acceleration signal of the diaphragm. The diaphragm motion and heart sounds analysis module 338 identifies transitions between inspiration stages and expiration stages of respiration cycles based on changes in the heart sound signals or the acceleration signal. Based on these changes the diaphragm motion and heart sounds analysis module 338 may identify an occurrence of an event of interest 706, such as end inspiration (EI) of a respiration cycle, and output an indication of such occurrence to the therapy module 340. Overtime, the diaphragm motion and heart sounds analysis module 338 may become tuned to the patient's respiration patterns such that the module may anticipate a particular respiration event before it occurs.

The IMD 300 determines whether the respiration cycle is at or near a particular respiration event, e.g., end inspiration. To this end, the therapy module 340 monitors for the receipt of an indication of a respiration event from the pressure signal module 330. In the absence of such an indication, the therapy module 340 delivers stimulation pulses 708a-708f to the diaphragm in accordance with the determined stimulation rate. That is, the therapy module 340 delivers a series of stimulation pulses at the stimulation rate until a respiration event of interest is detected.

If the therapy module 340 receives from the pressure signal module 330 an indication that a respiration event of interest 760 has been detected, the therapy module 340 may adjust stimulation therapy by withholding delivery of the stimulation pulse that would otherwise be delivered at or near an end of an inspiration stage. Referring to FIG. 7, two stimulation pulses 714a, 714b are withheld from delivery due to a corresponding detection of end inspiration 706a, 706b. Alternatively, as described above referring to FIG. 6E, instead of withholding delivery of the stimulation pulse that would otherwise be delivered at or near an end of an inspiration stage, the therapy module 340 may deliver the stimulation pulse but with one or more stimulation parameters adjusted to affectively deliver a stimulation pulse that does not produce a contraction of the diaphragm. For example, the pulse amplitude may be set to 0 volts, or the pulse width may be set to 0 milliseconds.

Device Configurations and Lead Designs

Figure 8:
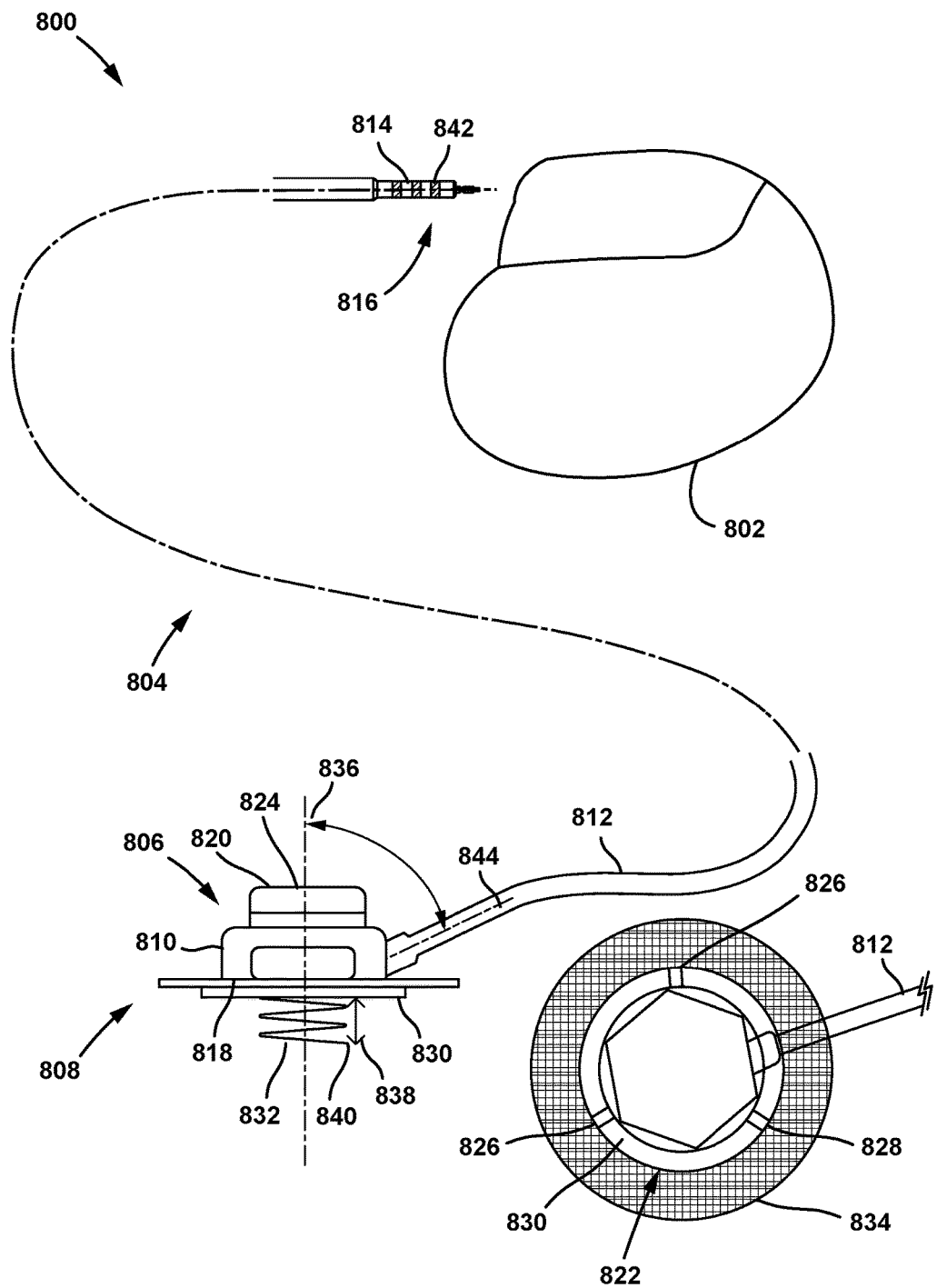
FIG. 8 is an illustration of a configuration of the implantable medical device of FIG. 3, including sense and stimulation components integrated with a lead, where the lead is coupled to a controller.

As previously mentioned, the IMD 300 of FIG. 3 may be implemented in either of a leaded configuration or a leadless configuration. Referring to FIG. 8, a leaded configuration of the IMD 800 includes a housing 802 connected to a lead 804. The housing 802 may correspond to the housing 304 of FIG. 3 and includes the controller 302 and the components contained therein. The lead 804 is configured for implant on a surface of a biological membrane forming part of a hermetically sealed biological cavity. For example, the biological membrane may be a diaphragm and the hermetically sealed biological cavity may be the thoracic cavity, as described above referring to FIG. 1.

The lead 804 includes a sensor assembly 806 at a distal end 808 of the lead. The sensor assembly 806 includes a housing 810, which may be cylindrical in shape, that is electrically coupled to a lead body 812 that extends from the distal end 808 of the lead to a connector 814 at the proximal end 816 of the lead. The housing 810 includes a first end surface 818 and a second end surface 820 that is opposite the first end surface. The sensor assembly 806 further includes a sensor structure 822 that is associated with the first end surface 818 of the housing 810. Conductive wires from the lead body 812 pass through the housing 810 to connect with sensors. A grip structure 824 extends from the second end surface 820 of the housing 810, and is configured to be received by a grip mechanism of an implant tool to be described below. The grip structure 824 may be formed of a hard rubber and to have a geometric shape, e.g., hexagon, the engages with the grip mechanism.

The sensor structure 822 includes one or more sensors 826, 828. The sensors may be, for example, electrodes 826 for sensing cardiac electrical activity, or a motion sensor 828, e.g. an acoustic transducer for sensing heart sounds or an accelerometer for sensing mechanical motion of the heart and/or the diaphragm. In the case of electrodes 826, the electrodes may be flat surface electrodes or ring electrodes. In one configuration, the sensor structure 822 includes a ring 830 having a circumference and one or more electrodes 826 spaced apart around the circumference of the ring, and possibility one or more motion sensors 828.

In another configuration, the entirety of the ring 830 may be a single electrode and another electrode may be located within the ring. In another configuration, the sensor structure 822 may include a number of preformed J-shaped, claws formed of shaped memory wire and located within a housing of the sensor structure, and configured therewith to extend through holes within the housing. While within the housing, the claws are maintained in a straight configuration. A mechanism extending along the length of the lead body 812 may be activated, e.g., pushed, pulled, or rotated, to cause the claws to exit the housing. As the claws exit the housing, they begin to assume their J shape and at least partially extend into the biological membrane.

The sensor assembly 806 further includes one or more fixation structures associated with the housing 810 for securing the sensor assembly to a biological membrane. In one embodiment, the fixation structure may be a projecting structure 832 that extends away from the housing 810 in a direction along a central axis 836 of the cylindrical housing. For example, as shown in FIG. 8, the projecting structure 832 may be in the form of a helix located in the center of the ring 830 that forms part of the sensor structure 822. The projecting structure 832 may be formed of an electrically conductive material and may function both as a fixation device for securing the sensor assembly 806 to a biological membrane, e.g., a diaphragm, and as an additional electrode for the sensor assembly. Alternatively, the projecting structure 832 may function solely as a fixation device.

In another embodiment, the fixation structure may be an extension member 834 that extends beyond the outer circumference of the housing 810. To this end, the extension member 834 has a maximum dimension, e.g., diameter, that is greater than a maximum dimension, e.g., diameter, of the housing 810. The extension member 834 may be in the form of a ring that surrounds the sensor assembly 806. As described further below, the extension member 834 may be configured in various ways to attach to the surface of the biological membrane to secure the sensor assembly 806 in place.

In yet another embodiment, the fixation structure may include, as shown in FIG. 8, both a projecting structure 832 and an extension member 834. In this embodiment, the extension member 834 surrounds the projecting structure 832 and is configured to form a seal between itself and the biological membrane, which seal surrounds the projecting structure. As described further below, this surrounding seal is beneficial in that it maintains the hermetic integrity of the intrathoracic cavity should the projecting structure 832 puncture through the diaphragm.

Each fixation structure 832, 834 is configured to secure the sensor assembly 806 to the surface of the diaphragm in a way that places the one or more sensors 826, 828 of the sensor structure 822 in functional contact with the diaphragm, while preserving the hermetic integrity of the biological cavity after implant of the lead. Functional contact means that the electrodes 826 are in direct or near direct contact with the diaphragm so as to sense cardiac electrical activity, while the motion sensor 828 is in direct or near direct contact with the diaphragm so as to sense one or more of movement of the diaphragm, movement of the heart, and heart sounds.

Considering further a fixation structure in the form of a projecting structure 832, such structure may be characterized by a protruding length 838 defined as the length between the surface of the sensor structure 822 and the distal tip 840 of the projecting structure. The protruding length 838 of the projecting structure 832 may be less than the thickness of the biological membrane to which the sensor assembly 806 is to be attached. For example, in a lead designed for implant on the surface of a diaphragm, the protruding length 838 may be, for example, between 0.25 centimeters and 0.5 centimeters. As such, the projecting structure 832 will not puncture through the diaphragm and hermetic integrity of the intrathoracic cavity is preserved. In cases where the protruding length 838 of the projecting structure 832 is less than the thickness of the biological membrane, the projecting structure may be formed of a wire having a substantially constant diameter, configured in the shape of a helix, as shown in FIG. 8. The helix 832 is twisted into the diaphragm to a depth sufficient to secure the helix into diaphragm tissue.

Figure 9:
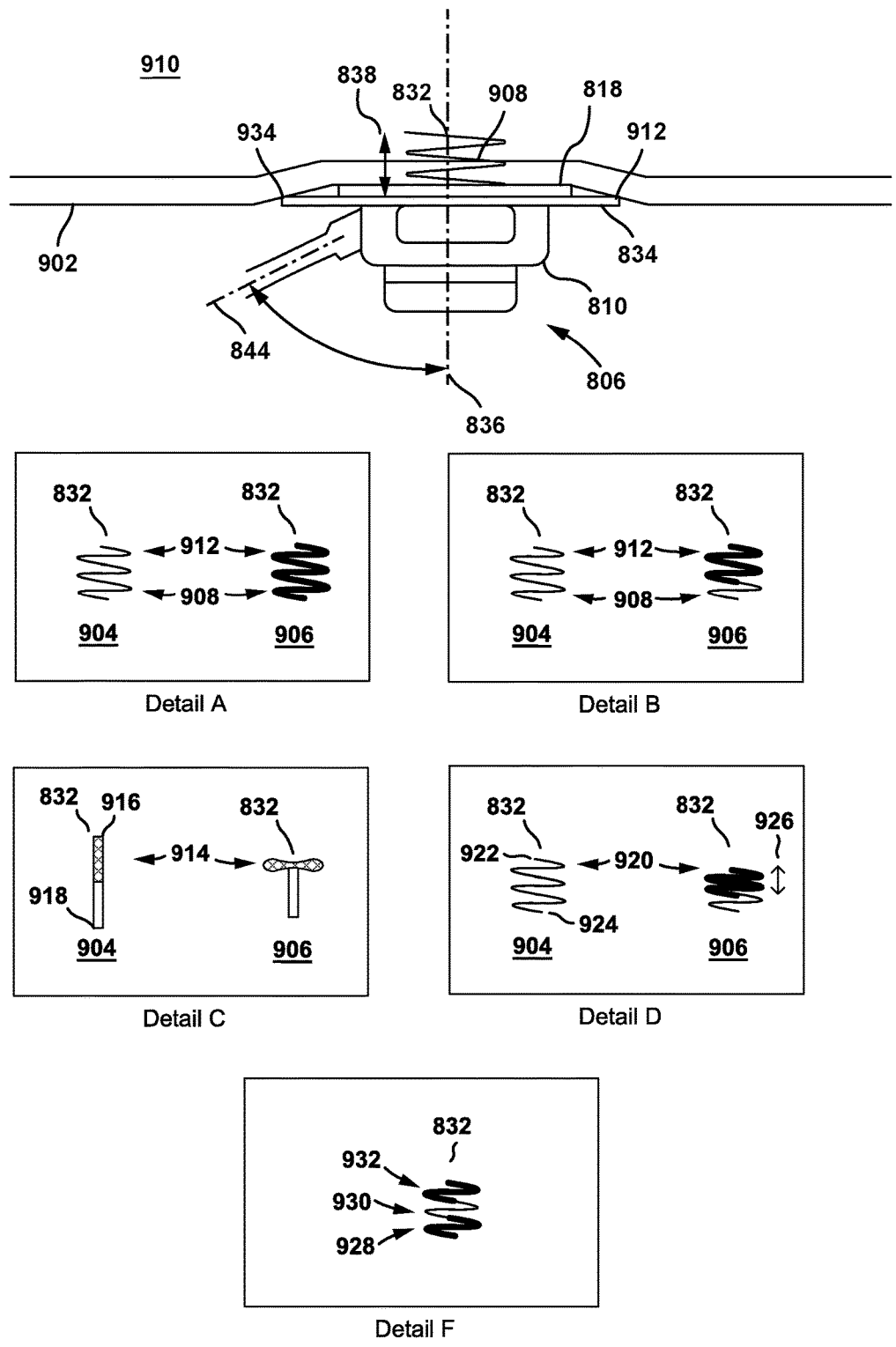
FIG. 9 is a side view illustration of a sensor assembly of the lead of FIG. 8 secured to a biological membrane, e.g., diaphragm, forming part of a hermetically sealed biological cavity, e.g., thoracic cavity.

Referring to FIG. 9, in other lead configurations, the protruding length 838 of the projecting structure 832 may be greater than the thickness of the biological membrane 902 to which the sensor assembly 806 is to be attached. For example, in a lead designed for implant on the inferior surface of a diaphragm 902, the protruding length 838 may be, for example, between 0.5 centimeters and 1.2 centimeters. As such, the projecting structure 832 will likely extend through the diaphragm 902, possibly disturbing the hermetic integrity of the intrathoracic cavity 910. This may have a detrimental effect on the patient's ability to breath because the respiration cycle depends on changes in pressure in the intrathoracic cavity 910.

To preserve the hermetic integrity of the intrathoracic cavity 910, the projecting structure 832 may be designed to form a seal at the location where the structure extends through the diaphragm 902. Hermetic integrity of the intrathoracic cavity 910 may also be preserved by an extension member 834 designed to form a seal that surrounds the location where the projecting structure 832 extends through the diaphragm 902.

In one design that preserves the hermetic integrity of the intrathoracic cavity, the projecting structure 832 is configured to actively transition between a first state, during which the wire forming all or a portion of the projecting structure has a first diameter, and a second state, during which the wire forming all or portion of the projecting structure has a second diameter greater than the first diameter. In one configuration of this active design, as shown in detail A of FIG. 9, the entire projecting structure 832 is configured to transition between the reduced-diameter state 904 and the expanded-diameter state 906. In another configuration, as shown in detail B of FIG. 9, only a portion of the projecting structure 832 is configured to transition between the reduced-diameter state 904 and the expanded-diameter state 906. For example, the projecting structure 832 may have a proximal section 908 and a distal section 912, where only the distal section is configured to transition between the reduced-diameter state 904 and the expanded-diameter state 906.

While each of the projecting structures 832 shown in detail A and detail B of FIG. 9 is shaped as helix, other shapes are possible. For example, the projecting structures 832 may be in the shape of a linear rod. Regardless of its shape, the projecting structure 832 may be in the first, reduced-diameter state 904 during implant to allow for easy extension of the projecting structure 832 through the membrane. After the projecting structure 832 extends through the membrane, all or a portion of the structure transitions to the second, expanded-diameter state 906. The expanded diameter region of the projecting structure that rests in the membrane 902 creates a tight fit with inner tissue of the membrane and forms a seal between itself and the membrane, thereby preserving the hermetic integrity of the intrathoracic cavity.

The projecting structure 832 may be configured to transition from the reduced-diameter state 904 and the expanded-diameter state 906 in any of several ways. For example, the entire projecting structure 832, or just the distal section 912, may be formed of a material that expands when exposed to body temperature for a period of time. In another configuration, a mechanical mechanism, e.g., mandrel, may be extend through the projecting structure 832 to apply an outward force to expand the entirety of the projecting structure or just the distal section 912. This expansion mechanism is primarily applicable to linearly shaped projecting structures 832.

Referring to detail C of FIG. 9, in another active design of a projecting structure 832 that preserves the hermetic integrity of the intrathoracic cavity, a distal section 914 of the projecting structure may be constructed of a metallic mesh configured to transition between a reduced-diameter state 904 and an expanded-diameter state 906. During implant the distal section 914 is compressed along its radial direction to assume the reduced-diameter state 904. This state of the distal section 914 allows for easy extension of the projecting structure 832 through the membrane 902. After the distal section 914 extends through the membrane 902, a mechanical force is applied at the distal end 916 of the distal section 914 towards the proximal end 918 of the projecting structure 832. The mechanical force causes the distal end 916 of the distal section 914 to displace towards the proximal end 918. This displacement, in turn, shortens the longitudinal length of the distal section 914, while expanding the radial diameter of the mesh that forms the distal section, thereby causing the distal section to assume the second, expanded-diameter state 906. A tension pull wire or other force transferring beam may be fixated to the distal end 916 of the distal section 914, which, when tension is applied by the operator, results in proximal forces and resulting radial expansion. A surface of the radially expanded distal section 914 rests tightly against the membrane 902 to form a seal between itself and the membrane, thereby preserving the hermetic integrity of the intrathoracic cavity.

In another active design of a projecting structure 832 that preserves the hermetic integrity of the intrathoracic cavity, a distal section 920 of the projecting structure may be configured to transition between a reduced-diameter state 904 and an expanded-diameter state 906 through one of deformation of the distal tip or rotation of the projecting structure. Referring to detail D of FIG. 9, the distal section 920 may be in the first, reduced-diameter state 904 during implant to allow for easy extension of the projecting structure 832 through the membrane. After the distal section 920 extends through the membrane, the distal section transitions to the second, expanded-diameter state 906. To this end, a pull wire extending through the interior of the projecting structure 832 and attached to the distal tip 922 of the distal section 920 may be used to apply a mechanical force to the tip toward the proximal end 924 of the projecting structure. The force causes the distal section 920 to flatten, i.e., the length 926 of distal section 920 shortens, while causing the width, i.e., diameter of the wire forming the distal section, to expand. In another design, the projecting structure 832 may be configured similar to a mesh stent. Initially the projecting structure 832 in the form of a mesh stent is in a compacted state. Upon rotation of the helical projecting structure 832 a certain number of rotations, the distal section 920 of the mesh stent expands from its compacted state to an increased diameter state, which in turn causes the distal section to shorten in length.

In another design that preserves the hermetic integrity of the intrathoracic cavity, the projecting structure 832 is configured to passively provide a seal between itself and the diaphragm membrane 902, without having to transition between a reduced-diameter state and an expanded diameter state, as described in the above designs. For example, in the configuration shown in detail F of FIG. 9, the projecting structure 832 includes a proximal section 928, a middle section 930, and a distal section 932. The middle section 930 has a smaller diameter than each of the proximal section 928 and the distal section 932. The lengths of the respective sections are sized so that upon implant of the projecting structure 832 through the diaphragm 902, the middle section 930 is located in the diaphragmatic muscle. This creates a physical circumferential groove or channel that seats the muscle along the length of the projecting structure 832 after the distal section 932 is inserted through the diaphragmatic skeletal muscle 902. The elastic nature of the diaphragmatic skeletal muscle 902 creates a mechanical coupling seal around the smaller diameter middle section 930, by expanding to seat along the length of the projecting structure 832 between the larger diameter proximal section 928 and the larger diameter distal section 932.

As previously mentioned, the hermetic integrity of the intrathoracic cavity 910 may be preserved by a fixation structure in the form of an extension member 834 designed to form a seal that surrounds the location where the projecting structure 832 extends through the diaphragm 902. Referring to FIG. 9, the extension member 834 is a generally planar structure that increases the overall size of the contact surface area of the sensor assembly 806 around the area where the projecting structure 832 extends through the diaphragm 902. The contact surface area corresponds to the surface area of the sensor assembly 806 that will contact the biological membrane 902. Upon implant of the sensor assembly 806, and over time, the biological membrane 902 may react to the presence of the sensor assembly and form an adhesive bond with the sensor assembly. The larger contact area provides for a larger adhesive bond radially outward from the where the projecting structure 832 extends through the diaphragm 902, which in turn results in a stronger hermetic seal around any hole through the diaphragm.

The extension member 834 may include other features that help secure the sensor assembly 806 in place and/or help expedite the formation of a seal with the surface of the biological membrane 902. For example, the extension member 834 may include an adhesive that both secures the sensor assembly 806 in place and forms a hermetic seal with the surface of the biological membrane around the area where the projecting structure 832 extends through the diaphragm 902. The extension member 834 may also include one or more suture holes that provide a means for securing the sensor assembly 806 in place.

In another configuration, the extension member 834 may be formed of a material configured to secure the sensor assembly 806 in place and to expedite the formation of a seal with the surface of the biological membrane 902 around the area where the projecting structure 832 extends through the diaphragm. For example, the extension member 834 may be a mesh material formed of polyester textile fiber, such as Dacron, or other fabric. Upon contact between the mesh structure 834 and the diaphragm 902, the mesh structure absorbs biological fluids on the surface of the diaphragm, clings to the diaphragm, and forms a seal 934 between itself and the diaphragm 902. This seal 934 surrounds the area where the projecting structure 832 extends through the diaphragm 902, and thus maintains the hermetic integrity of the intrathoracic cavity 910. The mesh structure 834 also functions to secure the sensor assembly 806 to the diaphragm.

The extension member 834 may be formed of a material that is softer than the material of the sensor structure 822 and the housing 810. For example, the extension member 834 may be formed of a material having a durometer of 60, while the housing 810 may be formed of a material having a durometer of 20.

Returning to FIG. 8, the connector 814 of the lead includes a number of contacts 842 corresponding to the number of electrodes 826 and sensors 828 associated with the sensor assembly 806. The lead body 812 includes conductors that electrically connect the contacts 842 at the proximal end 816 with the sensors 826, 828 of the sensor assembly 806. In one embodiment, the conductors are in the form of braided wires as opposed to coaxial wires. This reduces the structural integrity requirement of the cylindrical housing 810 or grip structure 824 used for screwing in the helix.

In order to decrease the potential symptomatic effects of stimulating the diaphragm in such a way that results in a contraction of the diaphragm, and to increase device longevity, the electrode sensors of the lead may be designed to provide an increased electrode surface area. For example, the entirety of the ring 830 may be an electrode as opposed to having a number of smaller electrodes spaced around the ring. Also, in the case of a helix that functions as an electrode, a material with a high conductivity may be selected as the helix material. Or a higher conductive material coating may be applied to the helix (verses current stainless steel-platinum.) Also, an indifferent electrode, such as the housing 802 of the IMD, may be incorporated into the system to change the resistance pathway.

The sensor assembly 806 is characterized by a central axis 836 extending through the housing 810. The lead body 812 is characterized by a longitudinal axis 846 that extends between the distal end 808 of the lead body and the proximal end 816 of the lead body. The longitudinal axis 846 of the lead body and the central axis 836 of the sensor assembly are not aligned. For example, the longitudinal axis 844 and the central axis 836 may be offset from each other by between 45-90 degrees. As such, after implant of the lead 804, the lead body 812 will rest in place substantially parallel with the surface of the biological membrane.

Figure 10:
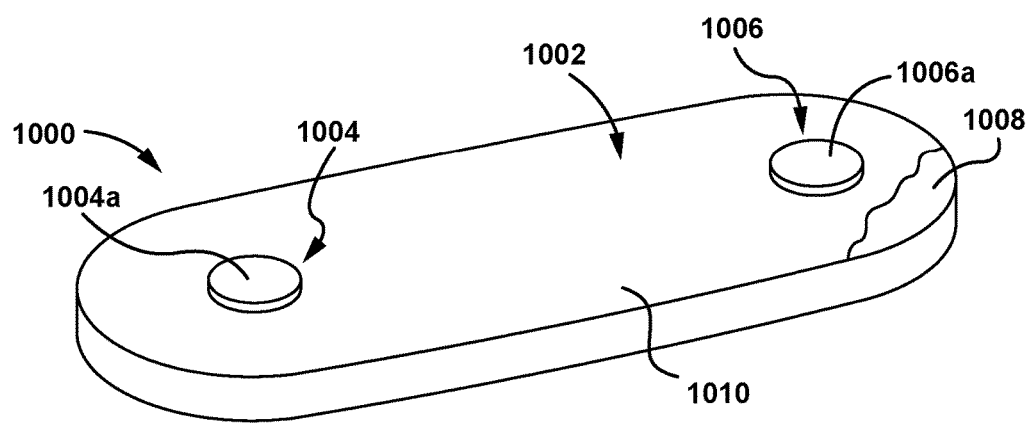
FIG. 10 is an illustration of a configuration of an implantable medical device of FIG. 3, including sense and stimulation components integrated with a controller.

Referring to FIG. 10, a leadless configuration of an IMD 1000 includes a housing 1002 with at least two electrodes 1004, 1006 closely associated with a surface of the housing. While the IMD 1000 illustrated in FIG. 10 is formed is the shape of an elongated disk, the IMD may have other form factors, including for example, a tube. The leadless IMD 1000 may have a length of about 1.25-inches, a width of about 0.5-inches, and a thickness of about 0.125-inches. The two electrodes 1004, 1006 are spaced apart by about 1-inch and are located on a surface 1008 of the housing. A non-electrically-conductive, biocompatible mesh 1010 may be affixed to the surface 1008 to facilitate anatomical bonding of the IMD 1000 to the surface region of the diaphragm.

Implant Tool

Figure 11A:
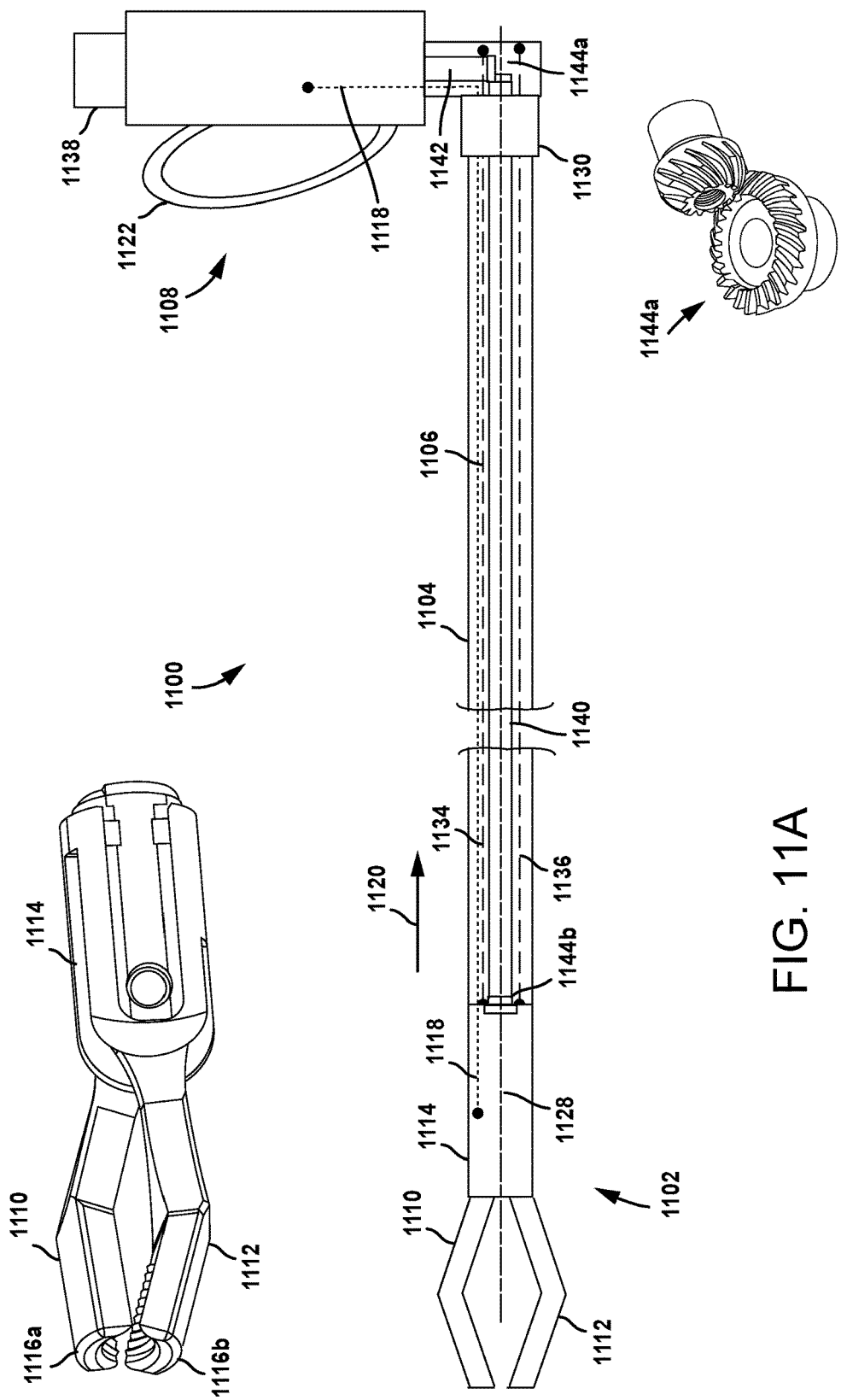
FIGS. 11A and 11B are schematic illustrations of a lead delivery tool configured to implant the lead of FIG. 8.
Figure 11B:
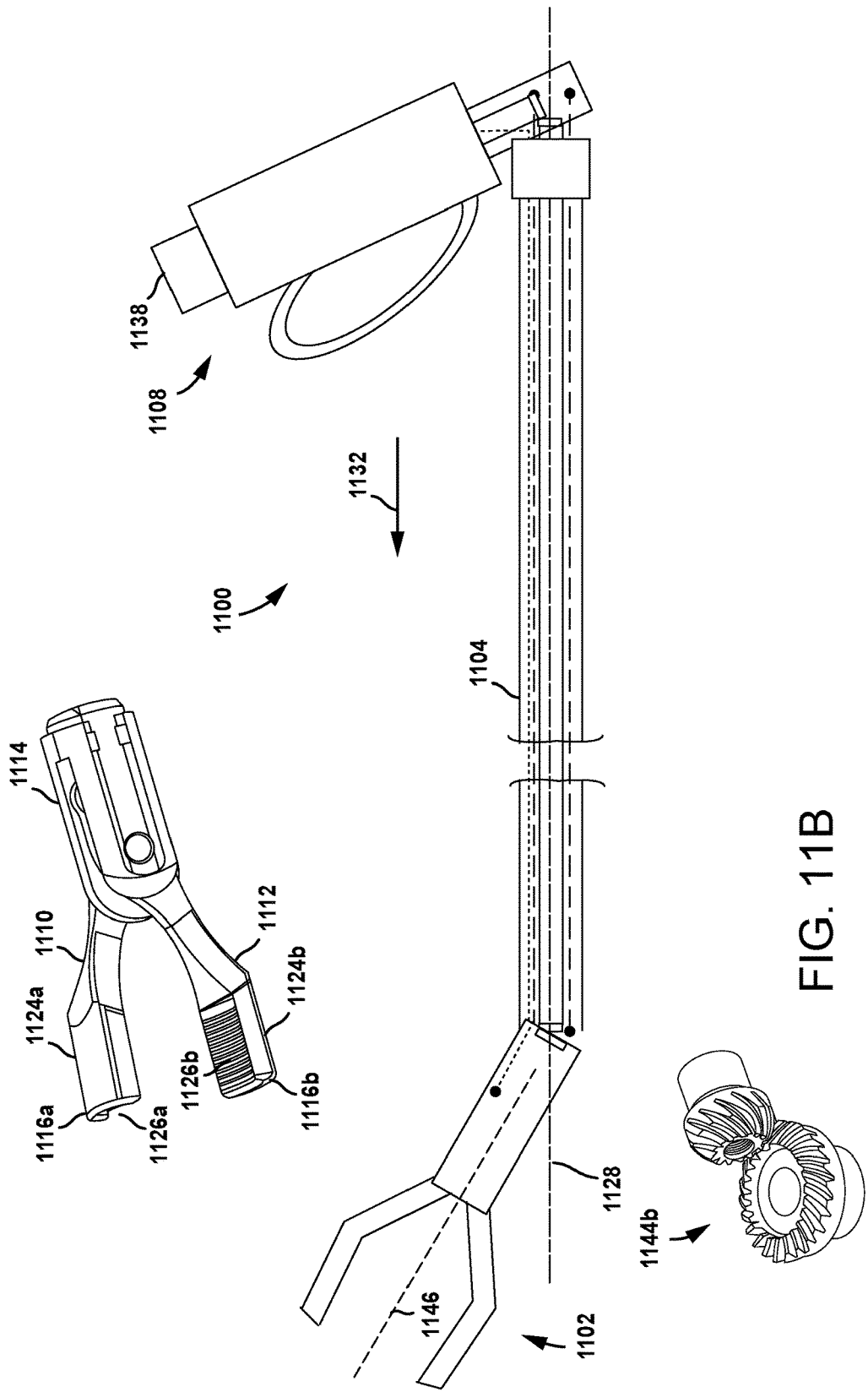

FIGS. 11A and 11B are schematic illustrations of a delivery tool 1100 configured to implant the lead of FIGS. 8 and 9. The delivery tool 1100 includes a grip mechanism 1102, a shaft 1104, a rod 1106 that fits within the shaft, and a handle 1108. The delivery tool 1100 is a modified version of a base tool available from Tuebingen Scientific (http://www.tuebingen-scientific.com/Standard/home/). Details of the base tool are described in U.S. Pat. Nos. 8,267,958 and 7,674,255, the disclosures of which are incorporated by reference.

Modifications to the base tool relate to a newly designed mechanism at the distal end of the tool, referred to herein as a grip mechanism, which is used to secure and release a lead during an implant procedure. As shown in FIGS. 11A and 11B, the grip mechanism 1102 includes a first arm 1110 and a second arm 1112, each of which are coupled to a base 1114. The arms 1110, 1112 are formed of an acutely biocompatible material with sufficient stiffness to secure the electrode during the implant procedure including but not limited to stainless steel, polytetrathylene, polyoxymethylene, nylon or combinations thereof. The arms 1110, 1112 are coupled to the base in a scissors like arrangement for movement relative to each other such that the grip mechanism 1102 may transition between a closed configuration (as shown in FIG. 11A) during which the tips 1116a, 1116b of the arms are close to each other, and an open arrangement (as shown in FIG. 11B) during which the tips of the arms are spaced apart. The grip mechanism 1102 is designed such that space between the tips 1116a, 1116b while in the open arrangement is large enough to receive a grip structure of the lead.

A grip tension cable 1118 is attached at a first end to the base 1114 of the grip mechanism 1102 and at a second end to the handle 1108. The distal end of the grip tension cable 1118 is attached to an open/close mechanism within the base 1114 such that when tension is applied to the cable in the direction of the handle 1108 (the proximal direction 1120), the first arm 1110 and the second arm 1112 are displaced from each other to form the open configuration of the grip mechanism 1102 (as shown in FIG. 11B.) Upon release of tension to the grip cable, the first arm 1110 and the second arm 1112 move toward each other to form the closed configuration of the grip mechanism 1102 (as shown in FIG. 11A). Tension may be applied to the grip tension cable 1118 by squeezing a lever 1122 of the handle 1108.

As shown in FIG. 11B, each of the arms 1110, 1112 of the grip mechanism 1102 include an arcuate distal portion 1124a, 1124b. The radius of curvature of the arcuate distal portions 1124a, 1124b may be selected to approximate a radius of curvature of a grip structure of the lead to be implanted to maximize the surface area contact between the grip mechanism of the tool and the grip structure of the lead. For example, as shown in FIGS. 12A and 12B, the radii of curvature of the arcuate distal portions 1124a, 1124b generally match the radius of curvature of the housing 810 portion of a lead to be implanted. The inside surfaces 1126a, 1126b of the arcuate distal portions 1124a, 1124b may be textured, for example with grooves or ridges, to increase friction between the grip mechanism and the lead being gripped. The inside surfaces 1126a, 1126b may also be formed of a material that is softer than the rest of the material forming the arms 1110, 1112.

In other designs the radii of curvature of the arcuate distal portions 1124a, 1124b does not necessarily approximate the grip structure of the lead. For example, referring to FIG. 8, a lead 804 may have a hexagon shaped grip structure 824. While the surface area contact between the grip mechanism 1102 of the tool and the grip structure 824 of the lead may be reduced in this design to the areas of contact between the points of the hexagon shaped grip structure the arcuate distal portions, the force exerted against the grip structure by the arms 1110, 1112 of the grip mechanism is sufficient to secure the lead within the grip mechanism. Furthermore, the grip structure 824 of the lead may be formed of a rubber material that compresses under the force of the grip mechanism 1102 to provide for a more secure grip between the lead and the grip mechanism.

Another modification of the base delivery tool relates to the amount of force applied by the grip mechanism 1102 when the mechanism is in the closed or locked position while grasping the sensor assembly end of a lead. To avoid damage to the sensor assembly, the grip tension cable 1118 is comprised of an elastically deforming material (rubber, nylon, elastic) in a braided configuration having a number of independent strands selected to increase the tension strength, while limiting the amount of the tension to the internal mechanisms of the tool. Limiting the amount of tension to the internal mechanisms, in turn, limits the subsequent amount of force transferred to the gripping arms 1110, 1112 towards the sensor assembly end of a lead.

In another modification of the tool, one or more electrodes are placed at the distal end of the tool with a conductive wire within a lumen of the tool. The conductive wire extends to a connector at the proximal end of the tool. The one or more electrodes enables impedance measures and diaphragmatic stimulation testing prior to lead implant. Such measurements and stimulation testing allow for a determination by the implanter of a preferred location of the diaphragm at which to place the lead electrodes. In an alternative embodiment, more than one electrode is used, spaced in an opposing manner across the distal section of the tool in order to maximize the contact spacing between the electrodes when placed on a flat diaphragm.

Another embodiment integrates a strain mediator of the axial pressure within the tension rod of the implant tool, such as a foam or spring compression disk. This mediates the forces applied to the distal end of the tool relative to the user handle at the proximal end reducing the effects of either rapid or excessive forces. A visual meter of compression percentage or forces may be integrated to provide the operator feedback on applied pressure to reduce the likelihood of excessive forces during the procedure, in order to preserve the hermetic seal of the diaphragm.

A general description of other components of the delivery tool and the operation thereof follows. The description is provided in order to enable a lead implant method to be described later. For a detailed description of the delivery tool, reference should be made to U.S. Pat. Nos. 8,267,958 and 7,674,255.

Continuing with FIGS. 11A and 11B, the shaft 1104 and rod 1106 align along a longitudinal axis 1128 of the delivery tool 1100. The grip mechanism 1102 together with the shaft 1104 may be rotated about the longitudinal axis 1128 by rotating a knob 1130 at the proximal end of the shaft 1104. The grip mechanism 1102 may be deflected relative to the longitudinal axis 1128 by pivoting the handle 1108 relative to the longitudinal axis. A pair of counter-balanced deflection cables 1134, 1136 extending from the handle 1108 to the grip mechanism 1102 facilitate this deflection. In FIG. 11B, the handle 1108 is pivoted in the distal direction 1132, which causes the grip mechanism 1102 to deflect from the longitudinal axis 1128. Once deflected to this position, the grip mechanism 1102 may be deflected back into alignment with the longitudinal axis 1128 by pivoting the handle 1108 in the proximal direction 1120. The grip mechanism 1102 may be defected between 0 and 120 degrees from the longitudinal axis 1128.

A torque transfer system extends between a torque transfer knob 1138 on the handle and the base 1114 of the grip mechanism 1102. The torque transfer system includes a first torque transfer rod 1140 that extends through the shaft 1104. The first torque transfer rod couples to the grip mechanism 1102 at one end and a second torque transfer rod 1142 in the handle 1108 at a second end. The coupling between the components is through gear mechanisms 1144*a*, 1144*b*. The grip mechanism 1102 may be rotated by itself and independent of rotation of the shaft 1104 by rotating the torque transfer knob 1138. For clarity, and referring to FIG. 11B, through rotation of the torque transfer knob 1138 the grip mechanism 1102 rotates about the axis 1146 of the grip mechanism while the shaft 1104 remains stationary.

Implant Method

A method of implanting a lead on a surface of a biological membrane forming part of a hermetically sealed biological cavity, includes accessing a surface of the biological membrane; securing a sensor assembly of the lead to a distal end of a lead delivery tool; placing the distal end of the lead delivery tool near the surface of the biological membrane; deflecting the sensor assembly so that sensor components of the sensor assembly are generally parallel to the surface of the biological membrane; rotating the sensor assembly to secure a fixation structure of the sensor assembly into the diaphragm; and release the sensor assembly from the distal end of the lead delivery tool.

Figure 13:
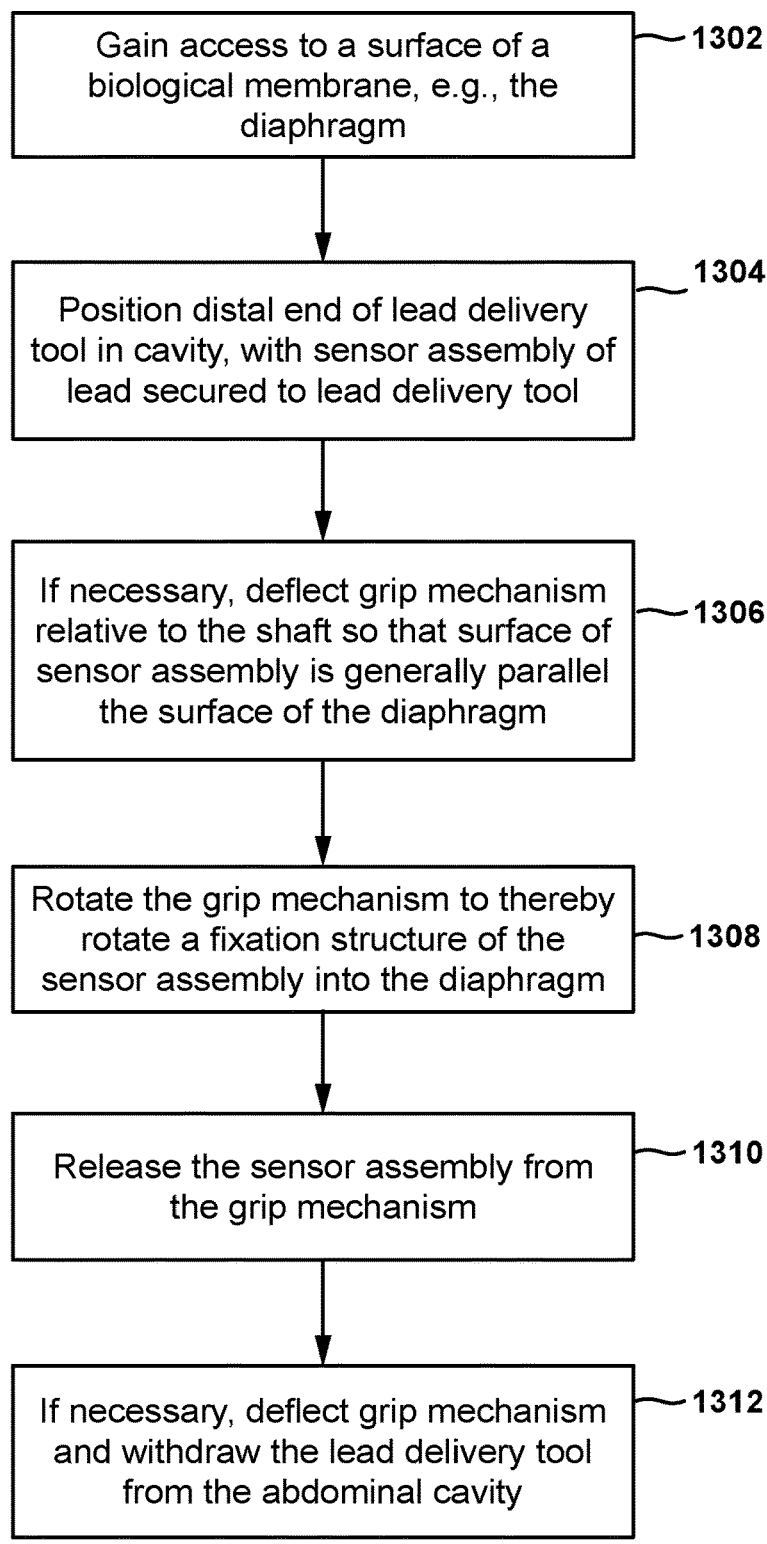
FIG. 13 is a flow chart of a method of implanting the lead of FIG. 8 using the delivery tool of FIGS. 11A and 11B.

FIG. 13 is a flow chart of a method of implanting a lead, such as the lead shown in FIG. 8, on a surface of a biological membrane forming part of a hermetically sealed biological cavity. In the described method, the biological membrane is a diaphragm and the biological cavity is the thoracic cavity. Furthermore, in the described method the lead is placed at a selected surface region of the diaphragm on the inferior side of the diaphragm at a location referred to as an inferior implant location. The implant method may be performed using a delivery tool as shown in FIGS. 11A and 11B.

At block 1302, the abdominal cavity is entered to gain access to the inferior side of the diaphragm. This may be done through conventional laparoscopy. A delivery sheath may be placed in the cavity to maintain an open path between the exterior of the patient and the interior of the cavity.

Figure 12:
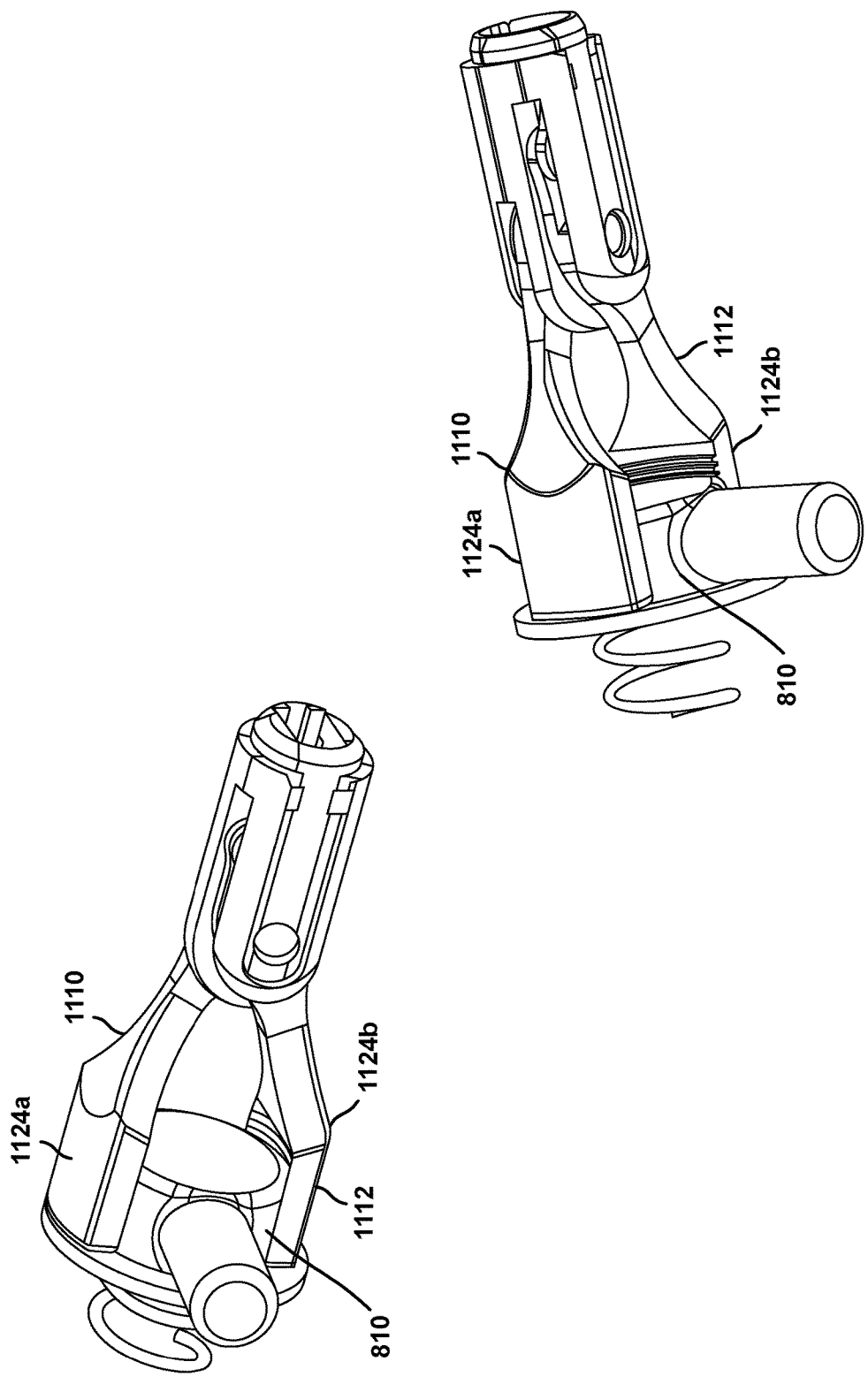
FIG. 12 are illustrations of a grip mechanism of the lead delivery tool of FIGS. 11A and 11B holding a distal end of a lead.

At block 1304, the distal end of lead delivery tool 1100 is positioned in the cavity through the delivery sheath. Prior to such placement, the distal end of the lead to be implanted is secured by a grip mechanism at the distal end of the lead delivery tool. For example, as shown in FIG. 12, the lead may include a sensor assembly having a housing 810 at its distal end that is configured to be placed between the first arm 1110 and the second arm 1112 of the grip mechanism 1102. As described above referring to FIGS. 11A and 11B, the grip mechanism 1102 may transition between an open configuration and closed configuration to secure the lead by squeezing the lever 1122 on the handle 1108.

While placing the distal end of the delivery tool 1100 in the cavity, the lead body 812 is maintained in a parallel relationship relative to the shaft 1104 of the delivery tool.

At block 1306, the grip mechanism 1102 may be deflected relative to the longitudinal axis 1128 of the shaft 1104 so that sensor structure 822 of lead 804 is generally parallel to the surface of the diaphragm 902. As described above referring to FIG. 11B, the grip mechanism 1102 may be deflected by pivoting the handle 1108 in the distal direction 1132.

At block 1308, once the that sensor structure 822 of lead 804 is generally parallel the surface of the diaphragm 902, the entirety of the delivery tool may be moved toward the diaphragm to place the sensor assembly 806 in contact with the diaphragm. If the sensor assembly 806 has a projecting structure 832, e.g., helix, the delivery tool may be moved until the tip of the helix touches the diaphragm. The grip mechanism 1102 is then rotated to thereby rotate sensor assembly 806 and the helix 832 into the diaphragm. As described above referring to FIG. 11B, the grip mechanism 1102 may be rotated through rotation of the torque transfer knob 1138.

At block 1310, after the grip mechanism is sufficiently rotated to secure the sensor assembly 806 to the diaphragm 902, the sensor assembly is released from the grip mechanism 1102. As described above referring to FIGS. 11A and 11B, the grip mechanism 1102 may transition between an open configuration and closed configuration to secure the lead by squeezing the lever 1122 on the handle 1108.

At block 1312, the delivery tool 1100 is removed from the abdominal cavity. Prior to doing so, if the grip mechanism 1102 was previously deflected to not align with the longitudinal axis 1128 of the shaft 1104 (as shown in FIG. 11B), the grip mechanism is deflected to align with the longitudinal axis of the shaft (as shown in FIG. 11A). As described above, the grip mechanism 1102 may be deflected by pivoting the handle 1108 in the distal direction 1132.

In a variation of the preceding method, during implant of the lead, one or more sensing electrodes at the distal end of the implant tool are placed into contact with the surface of the diaphragm. Connectors leading to the electrodes are externalized outside of the patient and connected to a separate sensing amplifier for analyzing signal characteristics and quality. One or measures of cardiac activity including R wave amplitude and R wave signal quality from the electrode location(s) are acquired through the electrodes to determine a preferred location on the diaphragm for permanent surgical implant location(s) for affixation. Once an ideal location is determined by the operator, the sensor assembly portion of the lead, including its electrodes, are affixed onto the surface of the diaphragm at the determined location by releasing the sensor assembly portion of the lead from the implant tool.

In another variation of the preceding method, an electrically conductive portion, e.g., the shaft 1104, of the implant tool is used as a mapping tool to identify the preferred location on the diaphragm to place the lead sensor assembly. The implant tool may be modified to contains a marking ink or other bio compatible, visual enabling substance near the distal end of the grasping mechanism. During the implant procedure, but prior to gripping the lead sensor assembly with the implant tool, a mapping procedure is performed using the tool to determine and mark the preferred location for placement of the lead sensor assembly. During the mapping procedure, the electrically conductive portions of the implant tool are used to sense and stimulate the diaphragm, thereby enabling electrode repositioning as needed to optimize diaphragmatic sensing of cardiac activity. One or more locations along the surface of the diaphragm are tested using measures of cardiac signal strength and signal quality, and optimal locations determined by the user. The visual enabling substance is then released from the implant tool to mark the diaphragmatic locations at which to place the electrodes of the lead sensor assembly. The implant tool is withdrawn, the lead that is to be permanently implanted is secured by the gripping mechanism of the implant tool, and the implant tool is used to place and secure the electrodes of the lead on the locations identified by the visual markers.

In another method of implanting a lead, a sensor assembly of the lead is secured to a biological membrane forming part of a hermetically sealed biological cavity. The sensor assembly is secured by a projecting structure that punctures a hole through the biological membrane. The lead is configured to preserve the hermetic integrity of the biological cavity. For example, the lead may be configured to form a seal between a structure of the lead and the biological membrane, wherein the seal completely surrounds the hole. The lead projecting structure of the lead may also be configured to plug the hole after implant.

In another method of affecting intrathoracic pressure, a contraction rate of a heart is detected. A pacing rate at which to deliver stimulation pulses to a diaphragm of the patient is determined based on the detected contraction rate. Stimulation pulses are delivered to the diaphragm at the determined pacing rate, wherein initiation of delivery of the stimulation pulses is timed relative to a detected contraction of the heart.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other magnetic storage devices. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A method of determining an optimal stimulation therapy for a patient, the method comprising:
    delivering an electrical stimulation therapy to a diaphragm of the patient, the electrical stimulation therapy being defined by a plurality of stimulation parameters;
    obtaining a signal indicative of a pressure within an intrathoracic cavity of the patient;
    changing at least one of the plurality of stimulation parameters, and then repeating the delivering and the obtaining, to obtain at least one additional signal
    deriving a measure of interest from each of the obtained signals; and
    selecting as the optimal stimulation therapy, the electrical stimulation therapy that results in a most acceptable measure of interest,
    wherein the obtained signal corresponds to a pressure signal and deriving a measure of interest comprises:
        generating a waveform based on the obtained signal;
        locating one or more fiducial points within the waveform; and
        determining the measure of interest from the waveform based on the one or more fiducial points, wherein:
the one or more fiducial points is a single point within a cardiac cycle, and
the measure of interest corresponds to a pressure measurement determined from the waveform at the single point.

2. The method of claim 1, wherein the signal indicative of a pressure within the intrathoracic cavity is obtained from one of a pressure sensor or a motion sensor associated with one of: a) an intrathoracic cavity, and b) a cardiovascular structure within the intrathoracic cavity.

3. The method of claim 2, wherein the cardiovascular structure comprises one of a right atrium, a right ventricle, a left ventricle, an aorta, and a pulmonary artery.

4. The method of claim 1, wherein the delivering and the obtaining occur over a period that encompasses one of: a single cardiac cycle, a plurality of cardiac cycles, at least one respiration cycle, and a specified duration.

5. A method of determining an optimal stimulation therapy for a patient, the method comprising:
delivering an electrical stimulation therapy to a diaphragm of the patient, the electrical stimulation therapy being defined by a plurality of stimulation parameters;
obtaining a signal indicative of a pressure within an intrathoracic cavity of the patient;
changing at least one of the plurality of stimulation parameters, and then repeating the delivering and the obtaining, to obtain at least one additional signal
deriving a measure of interest from each of the obtained signals; and
selecting as the optimal stimulation therapy, the electrical stimulation therapy that results in a most acceptable measure of interest,
wherein the obtained signal corresponds to a pressure signal and deriving a measure of interest comprises:
generating a waveform based on the obtained signal;
locating one or more fiducial points within the waveform; and
determining the measure of interest from the waveform based on the one or more fiducial points,
wherein:
the one or more fiducial points comprises a plurality of fiducial points, each of the plurality of fiducial points corresponding to a same point within a different cardiac cycle, and
the measure of interest corresponds to a statistical pressure measurement determined from a plurality of measurements, each of the plurality of measurements corresponding to a pressure measurement determined from the waveform at a respective one of the plurality of fiducial points.

6. The method of claim 5, wherein the statistical pressure measurement is an average.

7. The method of claim 5, wherein the plurality of fiducial points encompasses at least one respiration cycle.

8. A method of determining an optimal stimulation therapy for a patient, the method comprising:
delivering an electrical stimulation therapy to a diaphragm of the patient, the electrical stimulation therapy being defined by a plurality of stimulation parameters;
obtaining a signal indicative of a pressure within an intrathoracic cavity of the patient;
changing at least one of the plurality of stimulation parameters, and then repeating the delivering and the obtaining, to obtain at least one additional signal
deriving a measure of interest from each of the obtained signals; and
selecting as the optimal stimulation therapy, the electrical stimulation therapy that results in a most acceptable measure of interest,
wherein the obtained signal corresponds to a pressure signal and deriving a measure of interest comprises:
generating a waveform based on the obtained signal;
locating one or more fiducial points within the waveform, wherein the one or more fiducial points is located at or near a cardiac event, or a period after a cardiac event; and
determining the measure of interest from the waveform based on the one or more fiducial points.

9. The method of claim 8, wherein the cardiac event corresponds to a sensed ventricular event.

10. The method of claim 9, wherein the sensed ventricular event is one of an electrical ventricular event sensed by one or more electrodes, and a mechanical ventricular event sensed by one of accelerometer or an acoustic transducer.

11. A method of determining an optimal stimulation therapy for a patient, the method comprising:
delivering an electrical stimulation therapy to a diaphragm of the patient, the electrical stimulation therapy being defined by a plurality of stimulation parameters;
obtaining a signal indicative of a pressure within an intrathoracic cavity of the patient;
changing at least one of the plurality of stimulation parameters, and then repeating the delivering and the obtaining, to obtain at least one additional signal
deriving a measure of interest from each of the obtained signals; and
selecting as the optimal stimulation therapy, the electrical stimulation therapy that results in a most acceptable measure of interest,
wherein the obtained signal corresponds to a pressure signal and deriving a measure of interest comprises:
generating a waveform based on the obtained signal;
locating one or more fiducial points within the waveform; and
determining the measure of interest from the waveform based on the one or more fiducial points,
wherein:
the at least one of the plurality of stimulation parameters being changed is a timing parameter corresponding to a delay period between a detection of a cyclic cardiac event and a delivery of the electrical stimulation therapy, or a stimulation rate defining a rate at which electrical stimulation pulses are delivered, and
the most acceptable measure of interest corresponds to the measure of interest having a greatest deviation from a baseline value.

12. The method of claim 11, wherein the cyclic cardiac event comprises one of: a) an electrical cardiac event, and b) a mechanical cardiac event.

13. The method of claim 11, wherein the baseline value corresponds to one of: a) a measure of interest derived from a signal obtained in an absence of electrical stimulation therapy, and b) a predetermined nominal value.

14. The method of claim 11, wherein changing the timing parameter comprises one of: a) increasing the delay period, b) decreasing the delay period, c) increasing the stimulation rate, and d) decreasing the stimulation rate.

15. A method of determining an optimal stimulation therapy for a patient, the method comprising:
delivering an electrical stimulation therapy to a diaphragm of the patient, the electrical stimulation therapy being defined by a plurality of stimulation parameters;

obtaining a signal indicative of a pressure within an intrathoracic cavity of the patient;
changing at least one of the plurality of stimulation parameters, and then repeating the delivering and the obtaining, to obtain at least one additional signal
deriving a measure of interest from each of the obtained signals; and
selecting as the optimal stimulation therapy, the electrical stimulation therapy that results in a most acceptable measure of interest,
wherein the obtained signal corresponds to a pressure signal and deriving a measure of interest comprises:
generating a waveform based on the obtained signal;
locating one or more fiducial points within the waveform; and
determining the measure of interest from the waveform based on the one or more fiducial points,
wherein:
the at least one of the plurality of stimulation parameters being changed is one of a pulse amplitude or a pulse width duration that determines an energy output of the electrical stimulation therapy, and
the most acceptable measure of interest corresponds to the measure of interest that falls within a threshold range of acceptable measures of interest.

16. The method of claim 15, wherein, in a case where a plurality of derived measures of interest fall within the threshold range, selecting as the optimal stimulation therapy further comprises selecting the electrical stimulation therapy that outputs a minimum amount of energy.

17. The method of claim 15, wherein changing the pulse amplitude comprises one of increasing the pulse amplitude and decreasing the pulse amplitude, and changing the pulse width duration comprises one of increasing the pulse width duration and decreasing the pulse width duration.

18. A method of determining an optimal stimulation therapy for a patient, the method comprising:
delivering an electrical stimulation therapy to a diaphragm of the patient, the electrical stimulation therapy being defined by a plurality of stimulation parameters;
obtaining a signal indicative of a pressure within an intrathoracic cavity of the patient;
changing at least one of the plurality of stimulation parameters, and then repeating the delivering and the obtaining, to obtain at least one additional signal
deriving a measure of interest from each of the obtained signals; and
selecting as the optimal stimulation therapy, the electrical stimulation therapy that results in a most acceptable measure of interest,
wherein the obtained signal corresponds to a heart sound signal, and deriving a measure of interest comprises:
detecting an occurrence of a first cardiac event based on one of the heart sound signal or a cardiac electrical activity signal;
processing the heart sound signal to detect an occurrence of a second cardiac event; and
determining the measure of interest as a time between the occurrence of the first cardiac event and the occurrence of the second cardiac event.

19. The method of claim 18, wherein detecting the first cardiac event comprises filtering the heart sound signal in a first range of frequencies to identify a Q wave as the first cardiac event.

20. The method of claim 18, wherein detecting the first cardiac event comprises processing the cardiac electrical activity signal to identify a R wave as the first cardiac event.

21. The method of claim 18, wherein processing the heart sound signal to detect an occurrence of a second cardiac event comprises filtering the heart sound signal in a second range of frequencies to identify a maximum peak as the second cardiac event.

22. The method of claim 21, wherein the second cardiac event corresponds to a closure of a mitral value of the patient's heart.

23. The method of claim 18, wherein the most acceptable measure of interest corresponds to a shortest determined time.

24. The method of claim 18, wherein:
the at least one of the plurality of stimulation parameters being changed is one of a pulse amplitude or a pulse width duration that determines an energy output of the electrical stimulation therapy, or a timing parameter corresponding to a delay period between a detection of a cyclic cardiac event and a delivery of the electrical stimulation therapy, or a stimulation rate defining a rate at which electrical stimulation pulses are delivered.

25. The method of claim 24, wherein changing the timing parameter comprises one of: a) increasing the delay period, b) decreasing the delay period, c) increasing the stimulation rate, and d) decreasing the stimulation rate.

26. The method of claim 24, wherein changing the pulse amplitude comprises one of increasing the pulse amplitude and decreasing the pulse amplitude, changing the pulse width duration comprises one of increasing the pulse width duration and decreasing the pulse width duration.

27. An apparatus for determining an optimal stimulation therapy for delivery to a diaphragm of a patient, the apparatus comprising:
one or more electrodes configured for placement on or near the diaphragm;
a pressure measurement source configured to provide a signal indicative of a pressure within an intrathoracic cavity of the patient; and
a controller configured to:
deliver an electrical stimulation therapy to the diaphragm through the one or more electrodes, the electrical stimulation therapy being defined by a plurality of stimulation parameters;
obtain the signal indicative of a pressure within an intrathoracic cavity of the patient;
obtain at least one additional signal indicative of a pressure within an intrathoracic cavity of the patient by changing one of the plurality of stimulation parameters, and delivering an electrical stimulation therapy to the diaphragm of the patient, the electrical stimulation therapy being defined in part by the changed one of the plurality of stimulation parameters,
derive a measure of interest from each of the obtained signals; and
select as the optimal stimulation therapy, the electrical stimulation therapy that results in a most acceptable measure of interest,
wherein the obtained signal corresponds to a pressure signal, and the controller derives a measure of interest by being further configured to:
generate a waveform based on the obtained signal;
locate one or more fiducial points within the waveform; and
determine the measure of interest from the waveform based on the one or more fiducial points, and wherein:
the at least one of the plurality of stimulation parameters changed by the controller is a timing parameter corresponding to a delay period between a detection of a cyclic cardiac event and a delivery of the electrical stimulation therapy, or a stimulation rate defining a rate at which electrical stimulation pulses are delivered, and the most acceptable measure of interest corresponds to the measure of interest having a greatest deviation from a baseline value.

28. The apparatus of claim 27, wherein the pressure measurement source comprises one of a pressure sensor or a motion sensor configured to be associated with one of: a) an intrathoracic cavity, and b) a cardiovascular structure within the intrathoracic cavity.

29. The apparatus of claim 27, wherein the controller is configured to obtain a plurality of additional signals indicative of a pressure within an intrathoracic cavity over a period that encompasses one of: a single cardiac cycle, a plurality of cardiac cycles, at least on respiration cycle, and a specified duration.

30. The apparatus of claim 27, wherein the baseline value corresponds to one of: a) a measure of interest derived from a signal obtained in an absence of electrical stimulation therapy, and b) a predetermined nominal value.

31. The apparatus of claim 27, wherein the controller is included in an implantable medical device, which device comprises the one or more electrodes and the pressure measurement source.

32. An apparatus for determining an optimal stimulation therapy for delivery to a diaphragm of a patient, the apparatus comprising:
one or more electrodes configured for placement on or near the diaphragm;
a pressure measurement source configured to provide a signal indicative of a pressure within an intrathoracic cavity of the patient; and
a controller configured to:
deliver an electrical stimulation therapy to the diaphragm through the one or more electrodes, the electrical stimulation therapy being defined by a plurality of stimulation parameters;
obtain the signal indicative of a pressure within an intrathoracic cavity of the patient;
obtain at least one additional signal indicative of a pressure within an intrathoracic cavity of the patient by changing one of the plurality of stimulation parameters, and delivering an electrical stimulation therapy to the diaphragm of the patient, the electrical stimulation therapy being defined in part by the changed one of the plurality of stimulation parameters,
derive a measure of interest from each of the obtained signals; and
select as the optimal stimulation therapy, the electrical stimulation therapy that results in a most acceptable measure of interest,
wherein the obtained signal corresponds to a pressure signal, and the controller derives a measure of interest by being further configured to:
generate a waveform based on the obtained signal;
locate one or more fiducial points within the waveform; and
determine the measure of interest from the waveform based on the one or more fiducial points, and wherein:
the at least one of the plurality of stimulation parameters changed by the controller is one of a pulse amplitude or a pulse width duration that determines an energy output of the electrical stimulation therapy, and
the most acceptable measure of interest corresponds to the measure of interest that falls within a threshold range of acceptable measures of interest.

33. The apparatus of claim 32, wherein, in a case where a plurality of derived measures of interest fall within the threshold range, the controller is configured to select as the optimal stimulation therapy, the electrical stimulation therapy that outputs a minimum amount of energy.

34. An apparatus for determining an optimal stimulation therapy for delivery to a diaphragm of a patient, the apparatus comprising:
one or more electrodes configured for placement on or near the diaphragm;
a pressure measurement source configured to provide a signal indicative of a pressure within an intrathoracic cavity of the patient; and
a controller configured to:
deliver an electrical stimulation therapy to the diaphragm through the one or more electrodes, the electrical stimulation therapy being defined by a plurality of stimulation parameters;
obtain the signal indicative of a pressure within an intrathoracic cavity of the patient;
obtain at least one additional signal indicative of a pressure within an intrathoracic cavity of the patient by changing one of the plurality of stimulation parameters, and delivering an electrical stimulation therapy to the diaphragm of the patient, the electrical stimulation therapy being defined in part by the changed one of the plurality of stimulation parameters,
derive a measure of interest from each of the obtained signals; and
select as the optimal stimulation therapy, the electrical stimulation therapy that results in a most acceptable measure of interest,
wherein the obtained signal corresponds to a heart sound signal, and the controller derives a measure of interest by being further configured to:
detect an occurrence of a first cardiac event based on one of the heart sound signal or a cardiac electrical activity signal obtained from a cardiac event source;
process the heart sound signal to detect an occurrence of a second cardiac event; and
determine the measure of interest as a time between the occurrence of the first cardiac event and the occurrence of the second cardiac event.

35. The apparatus of claim 34, wherein the controller detects the first cardiac event by filtering the heart sound signal in a first range of frequencies to identify a Q wave as the first cardiac event.

36. The apparatus of claim 34, wherein the controller detects the first cardiac event by processing the cardiac electrical activity signal to identify a R wave as the first cardiac event.

37. The apparatus of claim 34, wherein the controller processes the heart sound signal to detect an occurrence of a second cardiac event by filtering the heart sound signal in a second range of frequencies to identify a maximum peak as the second cardiac event.

38. The apparatus of claim 34, wherein the most acceptable measure of interest corresponds to a shortest determined time.

39. An apparatus for determining an optimal stimulation therapy for delivery to a diaphragm of a patient, the apparatus comprising:
    one or more electrodes configured for placement on or near the diaphragm;
    a pressure measurement source configured to provide a signal indicative of a pressure within an intrathoracic cavity of the patient; and
    a controller configured to:
        deliver an electrical stimulation therapy to the diaphragm through the one or more electrodes, the electrical stimulation therapy being defined by a plurality of stimulation parameters;
        obtain the signal indicative of a pressure within an intrathoracic cavity of the patient;
        obtain at least one additional signal indicative of a pressure within an intrathoracic cavity of the patient by changing one of the plurality of stimulation parameters, and delivering an electrical stimulation therapy to the diaphragm of the patient, the electrical stimulation therapy being defined in part by the changed one of the plurality of stimulation parameters,
        derive a measure of interest from each of the obtained signals; and
        select as the optimal stimulation therapy, the electrical stimulation therapy that results in a most acceptable measure of interest,
    wherein the controller comprises:
        one or more implantable modules configured to delivery an electrical stimulation therapy to the diaphragm through the one or more electrodes, obtain and store the signal indicative of a pressure within an intrathoracic cavity of the patient, and obtain and store at least one additional signal indicative of a pressure within an intrathoracic cavity of the patient; and
        one or more external modules configured to receive the stored signals from the implantable modules, derive a measure of interest from each of the obtained signals, and select as the optimal stimulation therapy, the electrical stimulation therapy that results in a most acceptable measure of interest.

* * * * *